United States Patent [19]

Noguchi et al.

[11] Patent Number: 4,922,308
[45] Date of Patent: May 1, 1990

[54] METHOD OF AND APPARATUS FOR DETECTING FOREIGN SUBSTANCE

[75] Inventors: Minori Noguchi; Mitsuyoshi Koizumi; Hiroaki Shishido; Sachio Uto; Yoshimasa Ohshima, all of Yokohama, Japan

[73] Assignee: Hitachi, Ltd., Tokyo, Japan

[21] Appl. No.: 67,136

[22] Filed: Jun. 29, 1987

[30] Foreign Application Priority Data

| Jun. 27, 1986 [JP] | Japan | 61-149516 |
| Jun. 27, 1986 [JP] | Japan | 61-149517 |
| Jun. 27, 1986 [JP] | Japan | 61-149519 |
| Jun. 27, 1986 [JP] | Japan | 61-149520 |

[51] Int. Cl.⁵ .................................. G01N 21/88
[52] U.S. Cl. ................................ 356/237; 356/73; 356/239; 382/8
[58] Field of Search ............... 356/72, 73, 237, 401, 356/432, 445, 239; 382/8

[56] References Cited

U.S. PATENT DOCUMENTS

| 3,972,616 | 8/1976 | Minami et al. | 356/237 |
| 4,419,013 | 12/1983 | Heimer | 356/401 |
| 4,595,289 | 6/1986 | Feldman et al. | 356/237 |
| 4,610,541 | 9/1986 | Tanimoto et al. | 356/237 |
| 4,669,885 | 6/1987 | Ina | 356/73 |

Primary Examiner—Vincent P. McGraw
Assistant Examiner—S. A. Turner
Attorney, Agent, or Firm—Antonelli, Terry & Wands

[57] ABSTRACT

A method of and an apparatus for detecting a fine foreign substance in which the surface of a specimen is illuminated with linearly-polarized laser beam to detect light scattered from the surface and having passed through a polarization filter, the back side of the specimen is illuminated with light from a light source such as a mercury lamp to obtain the light and darkness information or phase information on the specimen surface by transmitted light from the specimen, and fine massive and filmy foreign substances on the specimen surface are detected on the basis of information given by the scattered light and transmitted light.

12 Claims, 74 Drawing Sheets

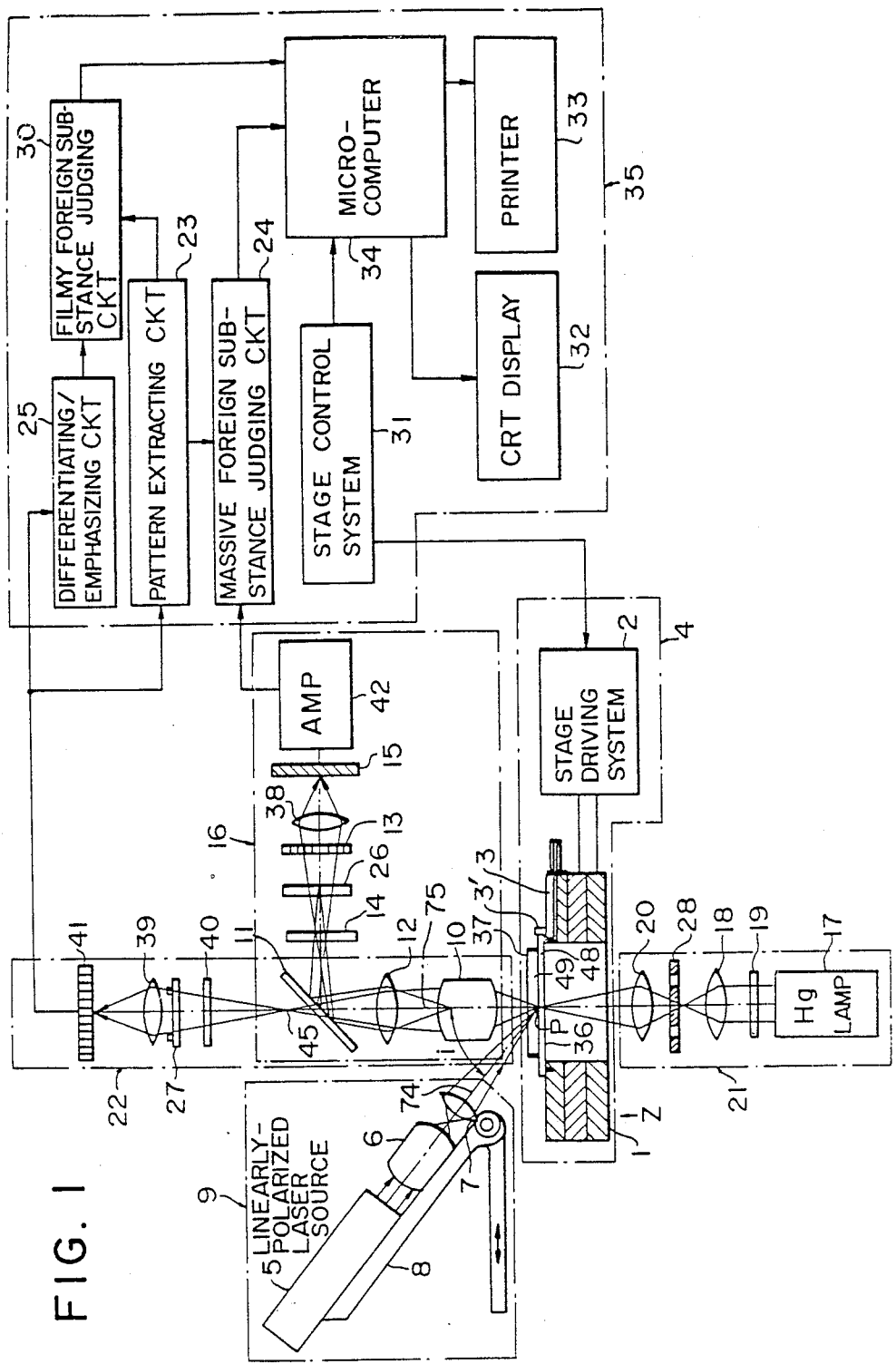

FIG. 14
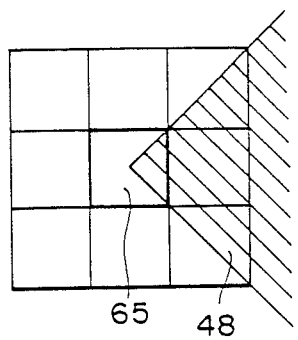
FIG. 15a 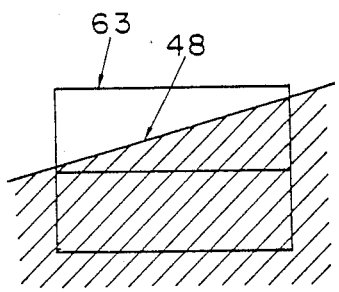 FIG. 15b 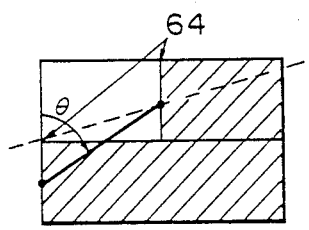
FIG. 17
| P11 V11 | P12 V12 | P13 V13 |
|---|---|---|
| P21 V21 | P22 V22 | P23 V23 |
| P31 V31 | P32 V32 | P33 V33 |

105: PHOTO MASK    107: PATTERN
106: FOREIGN SUBSTANCE  148: PATTERN DIRECTION

116: SPATIAL FILTER

175: LIGHT CUT-OFF PORTION
176: LIGHT TRANSMITTING PORTION

METHOD OF AND APPARATUS FOR DETECTING FOREIGN SUBSTANCE

BACKGROUND OF THE INVENTION

The present invention relates to a method of and an apparatus for detecting contaminating particles (a foreign substance) on a reticle (or photo-mask), before a circuit pattern on the reticle is projected on a wafer (or substrate) to form the circuit pattern thereon.

Conventional apparatuses for detecting a foreign substance on a reticle or photo-mask are disclosed in JP-A-59-65,428 and JP-A-54-101,390.

JA-P-59-65,428 discloses a foreign substance detecting apparatus which includes a laser device for emitting a linearly-polarized laser beam, means for causing the laser beam to impinge upon a reticle at a specified incident angle, and a focusing optical system made of a polarizer and a lens. In this apparatus, only reflected light from a foreign substance on the reticle is taken out by utilizing a fact that when the reticle is irradiated with the linearly-polarized light, the reflected light from the substrate and circuit pattern of the reticle is different in state of polarization from the reflected light from the foreign substance, and thus the foreign substance can be detected.

JP-A-54-101,390 discloses a foreign substance detecting apparatus which includes a laser device for emitting a laser beam, means for irradiating a specimen obliquely with the laser beam, a Fourier transform optical system formed of a lens, a spatial filter disposed in a Fourier transform plane, and a focusing optical system. In this apparatus, based on a fact that the greater part of a circuit pattern in a field of view is usually made up of pattern portions extended in one or a few directions, the diffracted light from the pattern portions is eliminated by the spatial filter disposed in the Fourier transform plane, to emphasize and take out only the reflected light from a foreign substance on the specimen.

Further, matters concerned with the foreign substance detecting apparatuses are described in, for example, a Japanese publication entitled "OYO-KOGAKU (Applied Optics)" by H. Kubota, pages 129 to 136 published by Iwanami Shoten, Publishers.

Recently, the integration density of an LSI (namely, large scale integration circuit) has been enhanced and the wiring pattern of the LSI has been made very fine. Thus, a fine foreign substance has become a serious problem. Further, a filmy foreign substance is formed of the remainder of a resist film in fabricating a reticle, the residue of chromium or chromium oxide for forming a pattern, or the condensate of impurities dissolved in a cleaning solution for a reticle. The above filmy foreign substance also has become a serious problem.

It is impossible for the techniques disclosed in JP-A-54-101,390 to discriminate a fine massive (or lump) foreign substance and a filmy foreign substance from a circuit pattern, since the reflective light from these foreign substances is very weak. The fine massive foreign substance can be emphasized by the techniques disclosed in JP-A-59-65,428, but the number of eliminable circuit patterns is limited. That is, it is impossible to eliminate all the circuit patterns by the same spatial filter.

SUMMARY OF THE INVENTION

It is an object of the present invention to provide a method of and an apparatus for detecting a foreign substance, in which in order to solve the above problems of the prior art, a fine massive foreign substance and a filmy foreign substance on a reticle or photo-mask having a desired circuit pattern are discrimated from the circuit pattern by emphasizing these foreign substances, and thus the foreign substances can be detected.

In order to attain the above object, according to an aspect of the present invention, a specimen is irradiated with a linearly-polarized laser beam, and through a focusing optical system comprising a polarization filter disposed so as to cut-off or intercept a light present on the polarization plane of the linearly-polarized laser beam and a spatial filter disposed so as to completely cut-off a light present on the rest of the above mentioned polarization plane area, the diffracted light from the pattern is cut-off or intercepted to emphasize the reflected light from a fine massive foreign substance. Further, according to the present invention, a phase contrast microscope is used for light passing through a specimen in such a manner that transmitted light from a filmy foreign substance is made stronger than background light due to the pattern or others.

In more detail, based on the observation that diffracted light rays from edges of a circuit pattern on a specimen have parallel planes of polarization in an area of a Fourier transform plane for the reflected light from the specimen, a polarization filter is disposed at the above area so as to intercept the diffracted light from the pattern edges. In this case, the reflected light rays from a fine massive foreign substance have planes of polarization of various directions, and thus can pass through the polarization filter. Further, the light incident on the remaining area of the Fourier transform plane is intercepted by the spatial filter capable of intercepting light completely. Thus, only the scattered light from the foreign substance appears on the rear side of these filters, and is emphasized by the focusing optical system, to be detected. Further, a filmy foreign substance is formed in such a manner that a substance different in refractive index from a specimen (for example, a reticle substrate made of $SiO_2$) is deposited on the reticle substrate, that is, a metal or ferroelectric substance is deposited on the reticle substrate in the form of a film. Accordingly, the phase of the light having passed through the filmy foreign substance lags only a little behind the phase of the light having passed through that portion of the reticle substrate which does not have a foreign substance. Accordingly, when the amplitude of the light having passed through the substrate portion with no foreign substance is made small at a Fourier transform plane in a phase contrast microscope and the phase of transmitted light from the reticle is delayed by a phase angle of $\pi/4$, only the filmy foreign substance can be emphasized and detected.

According to another aspect of the present invention, a fine massive foreign substance is detected in such a manner that information on edges of a circuit pattern is extracted from a detection signal based upon the transmitted light from a specimen by a pattern extracting circuit, and a signal portion based upon the scattered light from the foreign substance is taken out of a detection signal based upon the reflected light from the specimen by a foreign substance judging circuit. Further, based on the observation that when a specimen is illuminated with a linearly-polarized laser beam, diffracted light rays from a circuit pattern on the specimen have parallel planes of polarization in an area of a Fourier transform plane described in JP-A-59-65,428 for the specimen, a polarization filter is disposed for the above area, a spatial filter for intercepting light completely is disposed for the remaining area of the Fourier transform plane, and a linearly-polarized laser beam and a focusing optical system are used in the same manner as described in the above application. Thus, the diffracted light from the circuit pattern is intercepted, and the scattered light from the foreign substance is emphasized.

Meanwhile, a filmy foreign substance is detected from the detection signal based upon the transmitted light from a specimen by a filmy foreign substance detecting circuit, for example, a differentiating circuit for emphasizing edge portions of the filmy foreign substance. Further, based on the observation that the filmy foreign substance is formed when a substance different in refractive index from a specimen (for example, a reticle substrate made of $SiO_2$) is deposited on the reticle substrate, a phase contrast microscope is used for light passing through a reticle in such a manner that transmitted light from the filmy foreign substance is made stronger than background light due to a circuit pattern or others.

In more detail, the detection signal based upon light which is scattered from a specimen when the specimen is irradiated obliquely with a light beam contains a signal component based upon the scattered light from a fine massive foreign substance and another signal component based upon the scattered light from edge portions of a circuit pattern. The pattern extracting circuit extracts information with respect to pattern edges from the detection signal based upon the transmitted light from the specimen, and the foreign substance judging circuit eliminates the signal component based upon the scattered light from the pattern edges, from the detection signal based upon the scattered light from the specimen, to extract only the signal component based upon the scattered light from the fine massive foreign substance, thereby detecting the foreign substance without being affected by the scattered light from the pattern edges.

The filmy foreign substance detecting circuit performs a differentiating operation for the detection signal based upon the transmitted light from a specimen, to emphasize signal portions based upon edges of a filmy foreign substance, thereby detecting the filmy foreign substance. Thus, filmy foreign substances including a semi-transparent one which does not exhibit a pronounced contrast with the specimen, can be surely detected.

A further investigation of the analysis described in a Japanese article entitled "LSI wafer pattern kara no hanshako no kaiseki (Analysis of the Light Reflected from the Micro Patterns on the LSI Wafers)" (Trans. of the Society of Instrument and Control Engineers, Vol. 21, No. 8, pages 86 to 92) has shown that diffracted light rays from pattern edges have parallel planes of polarization in an area of a Fourier transform plane for a specimen. When a polarization filter is disposed in the above area so as to intercept linearly polarized light, the diffracted light from the pattern edges is intercepted by the polarization filter. Meanwhile, scattered light rays from a fine massive foreign substance have planes of polarization of various directions, and hence can pass through the polarization filter. Further, a spatial filter for intercepting light completely is disposed for the remaining area of the Fourier transform plane, and thus only the scattered light from the fine massive foreign substance can reach the rear side of these filters. The scattered light from the foreign substance is then emphasized and focused by a focusing optical system, to detect the foreign substance.

A filmy foreign substance is formed in such a manner that a metal or ferroelectric substance is deposited on a specimen in the form of a film. Accordingly, the phase of the light having passed through the filmy foreign substance lags only a little behind the phase of the light having passed through a specimen portion with no foreign substance. When the amplitude of the light having passed through the specimen portion with no foreign substance is made small at a Fourier transform plane in a phase contrast microscope, and the phase of transmitted light from the specimen is delayed by a phase angle of $\pi/4$, only the transmitted light from the filmy foreign substance is clearly observed, that is, only the filmy foreign substance is emphasized, and thus the filmy foreign substance can be readily detected.

BRIEF DESCRIPTION OF THE DRAWINGS

FIG. 1 is a block diagram showing an embodiment of a foreign substance detecting apparatus according to the present invention.

FIGS. 14, 15a, 15b, 16a and 16b are plan views showing picture elements of a detector and the image of a pattern edge portion.

FIG. 17 is a plan view showing picture elements of a detector.

DESCRIPTION OF THE PREFERRED EMBODIMENT

Figure 2A:
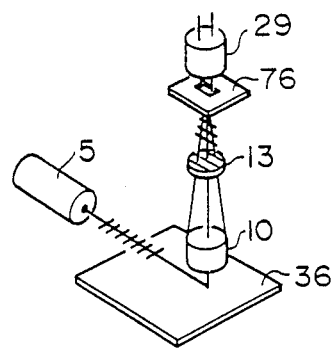
FIGS. 2a and 2b are perspective views for explaining how to detect a foreign substance.

Now, explanation will be made of an embodiment of a foreign substance detecting apparatus according to the present invention, with reference to FIGS. 1 to 22.

FIG. 1 shows the whole construction of the present embodiment. Referring to FIG. 1, the present embodiment is made up of a specimen holding unit 4, an oblique illumination unit 9, a scattered light detection unit 16, a transmitted-light producing illumination unit 21, a transmitted light detection unit 22, and a control unit 35. The specimen holding unit 4 includes an X-Y-Z stage 1, a driving system 2 for driving the X-Y-Z stage 1, and holding means 3 for fixing a photomask (or a reticle) 36 which is provided with a pellicle film 37 (for preventing a foreign substance from being deposited on the reticle 36) if necessary, to the stage 1 by the suction method in a state that the photo-mask (or the reticle) 36 is accurately located in relation to and pressed against a positioning pin 3'. The oblique illumination unit 9 includes a laser device 5 for emitting a linearly-polarized laser beam, a beam expander 6, a focusing lens 7, and setting means 8 for adjusting the direction and position of the laser beam manually so that the laser beam impinges on the photomask 36 at a predetermined position thereof and has a predetermined incident angle. The scattered light detection unit 16 includes an objective lens 10, a half mirror 11, relay lenses 12 and 38, an analyzer 13, an interference filter 14, a spatial filter 26, a one-dimensional solid state pick-up device 15, and a signal amplifier 42. The transmitted-light producing illumination unit 21 includes a mercury lamp 17, a ring diaphragm 28, a condenser lens 18, an interference filter 19 and a focusing lens 20. The transmitted light detection unit 22 includes the objective lens 10, relay lenses 12 and 39, a phase plate 27, an interference filter 40, and a one-dimensional solid state pick-up device 41. The control unit 35 includes a pattern portion extracting circuit (or a specified pattern extracting circuit which will be explained later) 23, a massive foreign substance judging circuit 24, a differentiating circuit 25 for differentiating a detection signal due to transmitted light, a filmy foreign substance judging circuit 30, a stage control system 31, a CRT (cathode ray tube) display 32, a printer 33 and a microcomputer 34.

Now, explanation will be made of the relation among constituent elements at each unit.

In the specimen holding unit 4, the photo-mask 36 is fixed to the X-Y-Z stage 1 by the holding means 3, and the stage 1 can be moved in the Z-direction, to inspect not only the surface of the photo-mask 36 but also the pellicle film 37 provided over the photo-mask. As described in the above-referred JP-A-59-65,428 and others, the pellicle film 37 is a thin transparent film and prevents a foreign substance from getting near the photo-mask 36.

The X-stage carries out a periodical motion in the X-direction in such a manner that one-half period includes an accelerating time of about 0.1 sec, a constant velocity time of 0.1 sec and a decelerating time of 0.1 sec, a maximum velocity is about 1 m/sec, and the periodic motion has an amplitude of 200 mm. In order to inspect an area of 100 mm×100 mm on the photo-mask 36, a central portion of the amplitude having a length of 100 mm corresponds to the constant-velocity time, and end portions on both sides of the central portion each having a length of 50 mm correspond to the accelerating or decelerating time.

The Y-stage moves in a Y-direction by a length of 0.15 mm in synchronism with the beginning of each accelerating time and each decelerating time of the X-stage. In a case where the Y-stage is displaced 670 times for one inspection, a time of about 130 seconds is necessary for moving the Y-stage by 100 mm. That is, it takes about 130 seconds to inspect an area of 100 mm×100 mm.

In the oblique illumination unit 9, the linearly-polarized beam emitted from the laser device 5 impinges on the photo-mask 36 through the beam expander 6 and the focusing lens 7. At this time, an incident angle i is set by the setting means 8. Scattered light from the photo-mask 36 travels in the scattered light detection unit 16. That is, the scattered light passes through the objective lens 10 and the relay lens 12, and is then reflected from the half mirror 11. The reflected light from the half mirror 11 passes through the interference filter 14 (for intercepting light from the transmitted-light producing illumination unit 21), the spatial filter 26 and the analyzer 13, and is then focused on the one-dimensional solid state pick-up device 15 by the relay lens 38. A detection signal from the pick-up device 15 is amplified by the amplifier 42, and then applied to the massive foreign substance judging circuit 24 of the control unit 35. Incidentally, the relay lens 12 is set so that light from the center of the exit pupil of the objective lens 10 is focused on the spatial filter 26.

Figure 2B:
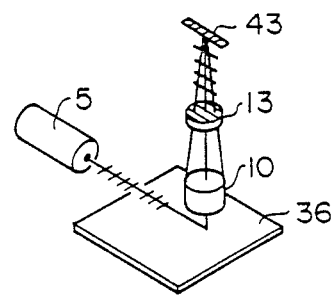

FIGS. 2a and 2b show how to detect the scattered light from the photo-mask 36 having been subjected to the oblique illumination. FIG. 2a shows a case where a single photodetector 29 is used, and FIG. 2b shows a case where a one-dimensional solid state pick-up array 43 is used. Each light receiving element of the pick-up array 43 is formed of a silicon photodiode or a GaAsP photodiode. The photodiode of the PIN junction type is excellent in response and sensitivity, and hence is suitable for use in the pick-up array of the present embodiment.

Figure 3C:
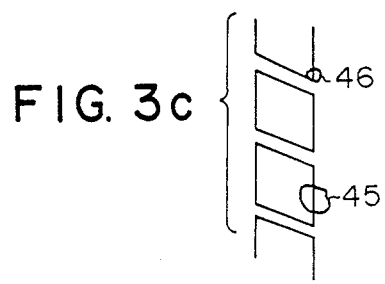
FIGS. 3a to 3e are plan views showing examples of positional relation between picture elements of a photodetector and foreign substances.
Figure 3A:
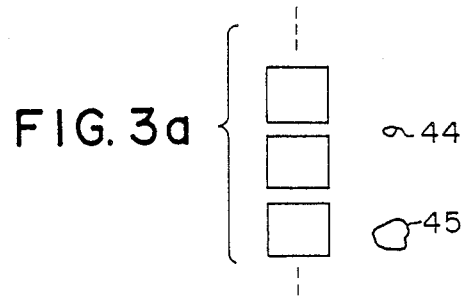
Figure 3D:
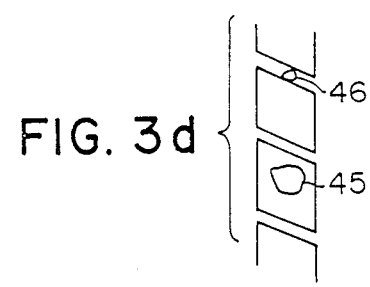
Figure 3B:
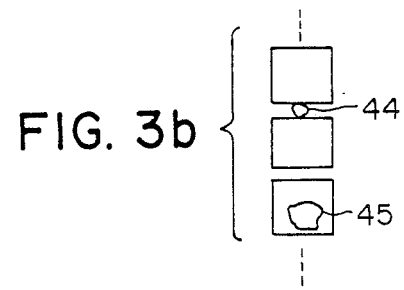
Figure 3E:
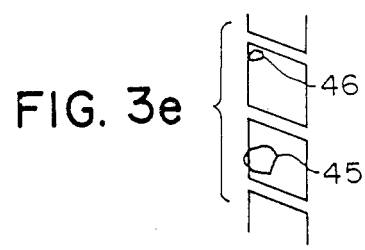

FIGS. 3a to 3b show examples of the positional relation between the light receiving elements (that is, picture elements) of the solid state pick-up array 43 and the images of foreign substances. As shown in FIGS. 3a to 3e, an insensitive region exists between adjacent picture elements of the array 43. In a case where the array 43 is made up of rectangular picture elements as shown in FIGS. 3a and 3b, when images 44 and 45 of foreign substances are moved on the insensitive regions in a direction perpendicular to one side of a picture element, the image 45 larger than the width of the insensitive region can be detected but the image 44 smaller than the width of the insensitive region cannot be detected as shown in FIG. 3b. In a case where the array 43 is made up of parallelogrammic picture elements as shown in FIGS. 3c to 3e, the above problem does not arise. In this case, however, an image 46 of foreign substance is detected by a plurality of picture elements as shown in FIGS. 3c and 3e, and thus the foreign substance is counted twice. In order to avoid such double count, various methods can be used which are disclosed in JP-A-56-132,549, JP-A-56-118,187, JP-A-57-66,345, JP-A-56-126,747 and JP-A-56-118,647.

Figure 4A:
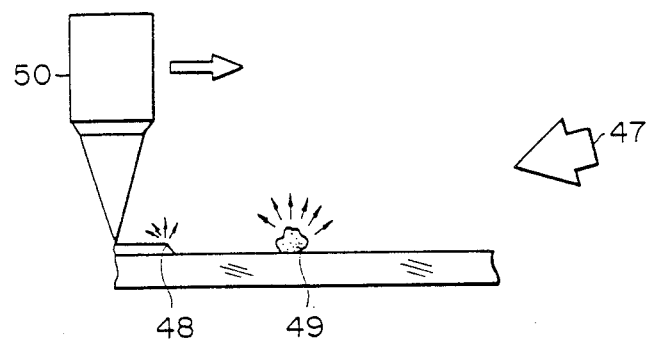
FIGS. 4a and 4b show the shape of foreign substances and the waveform of a detection signal resulting from the foreign substances, respectively.
Figure 4B:
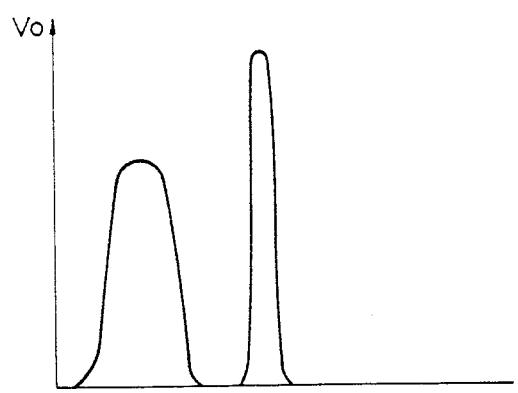
Figure 5A:
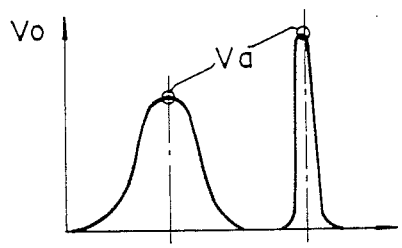
FIGS. 5a to 5d are waveform charts showing the outputs of foreign substance detecting circuits.
Figure 5B:
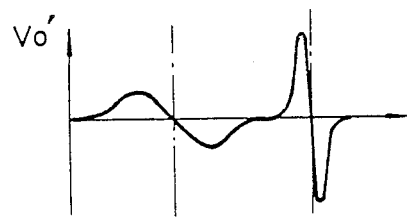
Figure 5C:
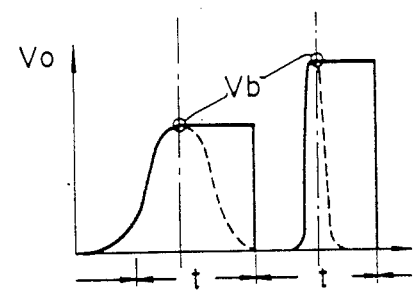
Figure 5D:
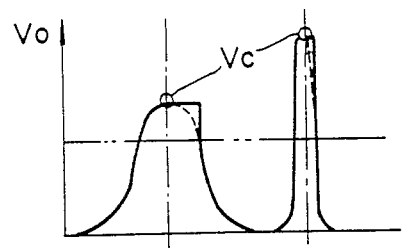

FIG. 4a shows a case where a pattern edge 48 and a massive foreign substance 49 each subjected to oblique illumination 47 are scanned with a scattered light detector 50, and FIG. 4b shows the waveform of the output $V_o$ of the detector 50. In the scattered light detection, peak values $V_a$ of the output $V_o$ such as shown in FIG. 5a are used. The peak value $V_a$ can be detected in such a manner that the value of the output $V_o$ at a point where the differentiated value $V_o'$ of the output $V_o$ changes from positive to negative, is used as the peak value. Alternatively, as shown in FIG. 5c the output $V_o$ is applied to a peak hold circuit which is reset when a predetermined time t has elasped, and the output $V_b$ of the peak hold circuit at a reset time is used as the peak value $V_a$. Further, the peak value $V_a$ may be detected in the following manner. Referring to FIG. 5d, the output $V_o$ is applied to a peak hold circuit which is reset when the output $V_o$ becomes lower than a predetermined threshold level, and the output $V_c$ of the peak hold circuit at a reset time is used as the peak value $V_a$. Referring back to FIGS. 2a and 2b, in the oblique illumination, the S-polarized light from the laser device 5 impinges on the photo-mask 36 at an incident angle i which is set so that a pellicle frame on the photo-mask 36 does not interfere with the S-polarized light as described in JP-A-59-82,727. Scattered light from the photo-mask passes through the objective lens 10 and a P-analyzer 13, and is then focused on the detector 29 or 43 by a relay lens (not shown). In the present embodiment of FIG. 1, it is not always required to use the S-polarized light, the analyzer 13 and the spatial filter 26. However, by using the above members, a massive foreign substance can be surely detected.

Figure 6:
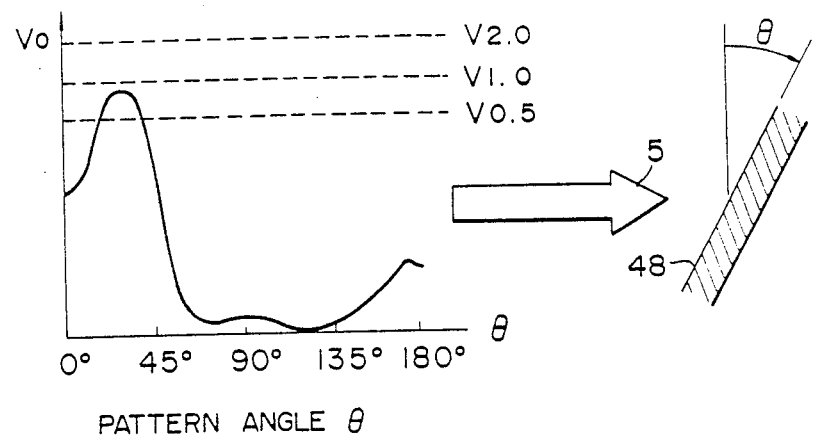
FIG. 6 is a graph showing a relation between a pattern angle $\theta$ and the output of a detector which receives scattered light from a pattern.

FIG. 6 shows a relation between a pattern angle and the detected quantity of light scattered from a pattern edge. Referring to FIG. 6, when a photo-mask is viewed from above, an angle $\theta$ between a direction perpendicular to the traveling direction of the laser beam from the laser device 5 in the oblique illumination unit and a pattern edge 48 is used as the pattern angle. Further, the outputs $V_{2.0}$, $V_{1.0}$ and $V_{0.5}$ of a detector for standard foreign substances having diameters of 2 $\mu$m, 1 $\mu$m and 0.5 $\mu$m are also described in the graph of FIG. 6. As can be seen from FIG. 6, when it is required to detect the standard foreign substance having a diameter of 0.5 $\mu$m, it is impossible to discriminate the above foreign substance from a pattern having a pattern angle of 10° to 30° (hereinafter referred to as "specified pattern") by using only the quantity of scattered light. A foreign substance detecting method capable of solving the above problem will be explained below.

Figure 7:
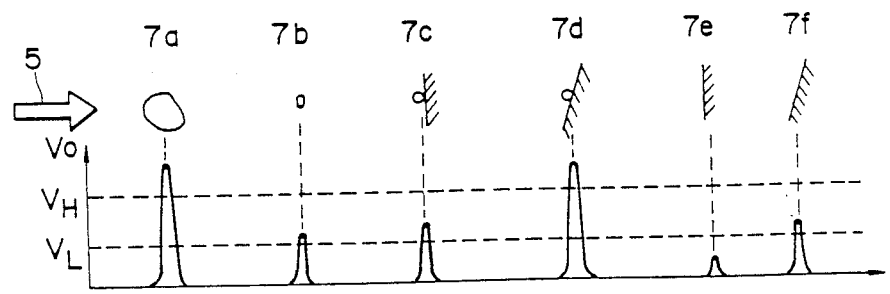
FIG. 7 is a waveform chart showing the outputs of a detector for various foreign substances.

FIG. 7 shows the output $V_o$ of the scattered light detection unit 16 due to the scattered light from each of a large isolated foreign substance 7a, an isolated foreign substance 7b having a diameter of 0.5 $\mu$m, a foreign substance 7c kept in contact with a non-specified pattern and having a diameter of 0.5 $\mu$m, a foreign substance 7d kept in contact with a specified pattern and having a diameter of 0.5 $\mu$m, a non-specified pattern 7e and a specified pattern 7f. Further, two threshold levels $V_H$ and $V_L$ are set as shown in FIG. 7. When the output $V_o$ of the detection unit is not lower than the threshold level $V_H$, the large foreign substance 7a or the foreign substance 7d kept in contact with a specified pattern exists, and thus it is judged that a foreign substance is present. When the output $V_o$ is lower than the threshold level $V_L$, it is judged that no foreign substance is present. Further, in a case where the output $V_o$ lies in a range from $V_L$ to $V_H$ and any specified pattern is not detected, it is judged that a foreign substance is present. In a case where the output $V_o$ lies in the range from $V_L$ to $V_H$ and a specified pattern is present, it is judged that no foreign substance is present. That is, when the presence of a specified pattern is expressed by P, the presence D of a foreign substance is given by the following equation:

$$D = (V_o \geq V_H) \cup \{(V_o < V_H) \cap (V_o \geq V_L) \cap \bar{P}\}$$

Figure 8:
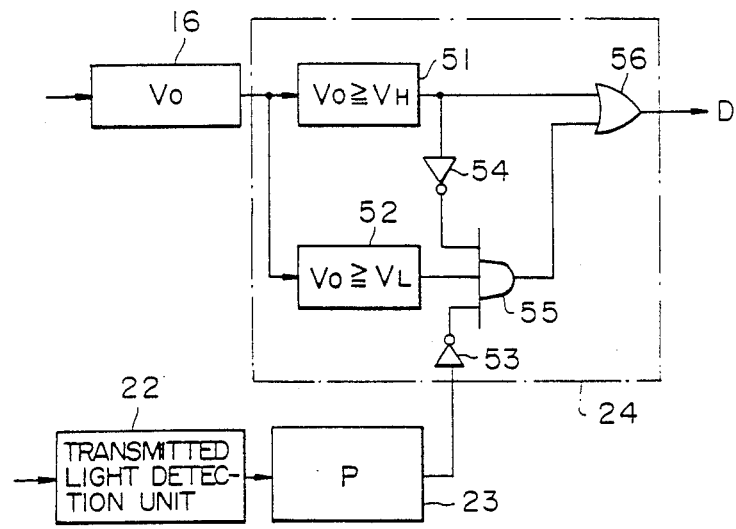
FIGS. 8 and 11 are block diagrams showing massive foreign substance judging circuits.

FIG. 8 shows an example of a circuit for the above algorithm. Referring to FIG. 8, the output $V_o$ of the scattered light detection unit 16 is applied to a comparator 51, to be compared with the threshold level $V_H$, and is also applied to another comparator 52, to be compared with the threshold level $V_L$. The output of the comparator 51 is applied to an OR circuit 56 and a NOT circuit 54. Meanwhile, the output of the transmitted light detection unit 22 is applied to a specified pattern extracting circuit 23, which delivers a signal having a level "1" when a specified pattern is detected. The output of the specified pattern extracting circuit 23 is polarity-inverted by a NOT circuit 53, and then applied to an AND circuit 55. The AND circuit 55 is also applied with the outputs of the comparator 52 and the NOT circuit 54. The output of the AND circuit 55 is applied to the OR circuit 56.

Figure 9:
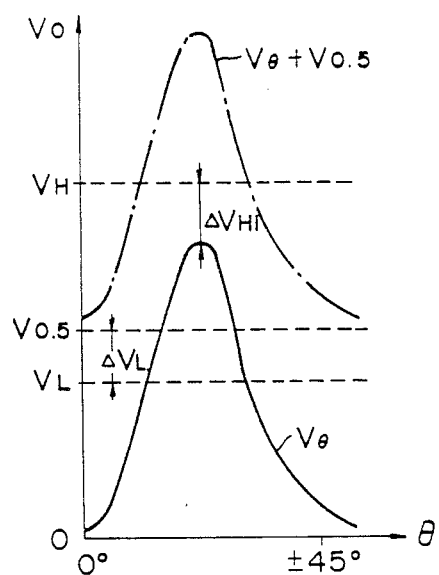
FIGS. 9 and 10 are graphs for explaining the operations of the judging circuits of FIGS. 8 and 11, respectively.

FIG. 9 shows the output $V_\theta$ of the scattered light detection unit for the scattered light from a pattern having a pattern angle of 0° to ±45°, the output $V_{0.5}$ for the scattered light from a standard foreign substance having a diameter of 0.5 $\mu$m, the output $V_0 + V_{0.5}$ for the scattered light from a 0.5 $\mu$m diameter standard foreign substance which exists in close proximity to a pattern having a pattern angle of 0° to ±45°, and the threshold levels $V_H$ and $V_L$. In a case where the standard foreign substance is discriminated from the pattern by the above-mentioned algorithm, the distance $\Delta V_L$ between the output $V_{0.5}$ and the threshold level $V_L$ is a margin for preventing the foreign substance from being missed, the distance $\Delta V_H$ between the peak value of the output $V_{74}$ and the threshold level $V_H$ is a margin for preventing the erroneous detection of the pattern. When the output $V_{0.5}$ is considered to be equal to one (1), each of the $\Delta V_L$ and $\Delta V_H$ is about 0.25.

As mentioned above, a fine foreign substance can be detected by the above-mentioned algorithm and the circuit of FIG. 8. The algorithm for surely detecting a foreign substance by enlarging the margins $\Delta V_H$ and $\Delta V_L$ will be explained below.

Figure 10:
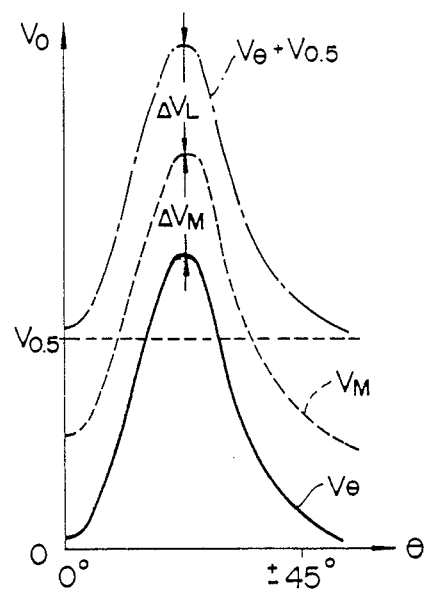
Figure 11:
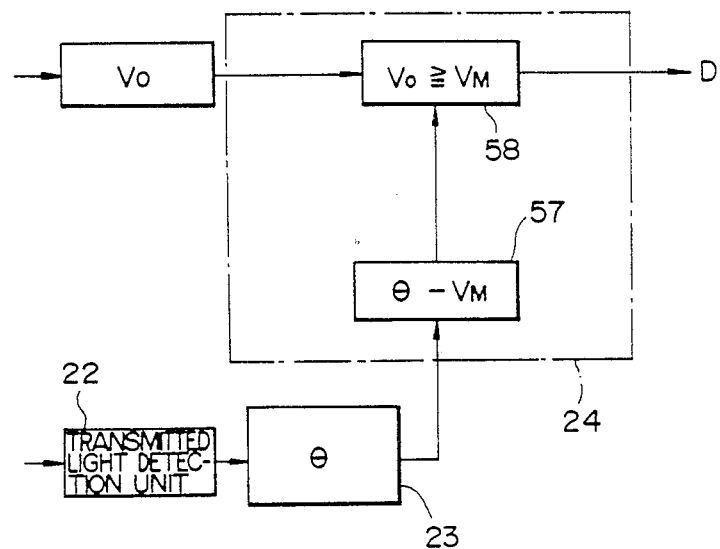

As shown in FIG. 6, the detected quantity of light scattered from a pattern varies with a pattern angle $\theta$. In view of this fact, a foreign substance is detected by the following algorithm. That is, a pattern angle $\theta$ on the photo-mask is first detected by using transmitted light. Then, a threshold level $V_M$ is varied as shown in FIG. 10 on the basis of the output $V_R$ of the detection unit corresponding to the detected pattern angle and previously stored in a memory. When the output $V_o$ of the scattered light detection unit 16 is not lower than the threshold level $V_M$, it is judged that a foreign substance is present. When the output $V_o$ is lower than the threshold level $V_M$, it is judged that no foreign substance is present. In this algorithm, the margins $\Delta V_H$ and $\Delta V_L$ are given as shown in FIG. 10. When the output $V_{0.5}$ of FIG. 10 is considered to be equal to 1 (one), each of the margins $\Delta V_H$ and $\Delta V_L$ is about 0.5. Thus, the margin $\Delta V_H$ or $\Delta V_L$ of FIG. 10 is twice larger than the margin $\Delta V_H$ or $\Delta V_L$ of FIG. 9. FIG. 11 shows an example of a circuit for the present algorithm. Referring to FIG. 11, the output $V_o$ of the scattered light detection unit 16 is applied to a comparator 58, to be compared with the threshold level $V_M$. The output of the transmitted light detection unit 22 is applied to the pattern portion extracting circuit 23, which detects the pattern angle $\theta$ of an inputted pattern. The detected pattern angle $\theta$ is applied to a $V_M$-level generating circuit 57, and the output $V_M$ of the circuit 57 is applied to the comparator 58.

Next, a method of extracting a specified pattern will be explained below, with reference to FIGS. 12a to 17. A specified pattern can be detected by checking whether or not an image of pattern formed by the transmitted light agrees with one of those images of specific patterns which are previously stored in a memory. In this method, however, it is necessary to extract the image of pattern very accurately, and hence the picture elements of the image pick-up device are required to be small in size. Accordingly, it is necessary to scan a specimen with a light beam a large number of times, and thus a time required for inspecting the specimen becomes long. For example, in a case where a 0.5-μm picture element is used for detecting a foreign substance having a diameter of 0.5 μm, it takes 46 minutes to scan an area of 100×100 mm, since it is impossible to make each of the moving speed of the specimen holding table and the response time of the detector greater than a limiting value.

Now, explanation will be made of a method of extracting a specified pattern by using a large picture element.

Figure 12A:
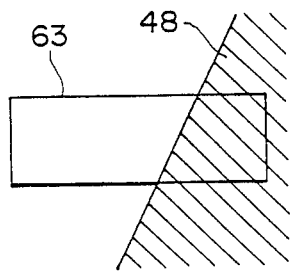
FIGS. 12a to 12c are plan views showing the picture element of a detector and the image of a pattern.
Figure 12B:
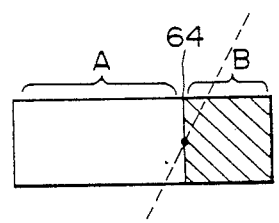
Figure 12C:
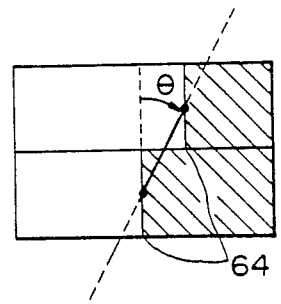

In a case where a pattern edge 48 is projected onto a rectangular picture element 63 (which may be replaced by a square picture element) of an image pick-up array as shown in FIG. 12a, the picture element 63, as shown in FIG. 12b, delivers an output $V_o \propto A/(A+B)$ corresponding to the mean position 64 of the pattern edge 48 at the picture element 63 in directions parallel to the longer sides thereof (namely, the position of the pattern edge 48 on that center line of the picture element 63 which is parallel to the longer sides thereof). Accordingly, when a plurality of picture elements are used as shown in FIG. 12c, a pattern angle $\theta$ of the edge 48 can be detected from the outputs of the picture elements. As mentioned above, according to this method, a specified pattern can be detected accurately even when large picture elements are used. Accordingly, this method is suitable for the high-speed detection of a foreign substance.

Figure 13:
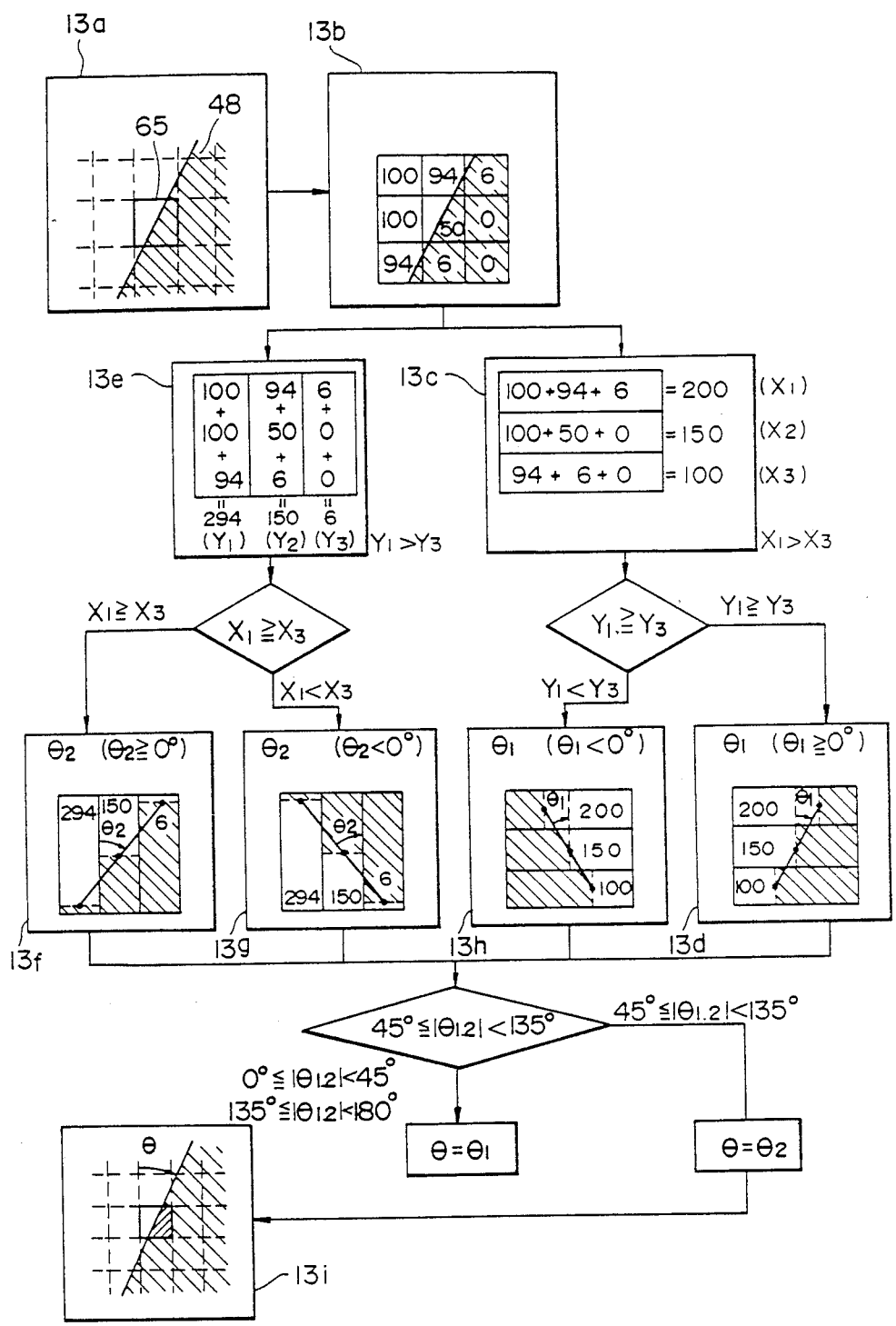
FIG. 13 is a diagram showing an algorithm for determining a pattern angle.
Figure 16A:
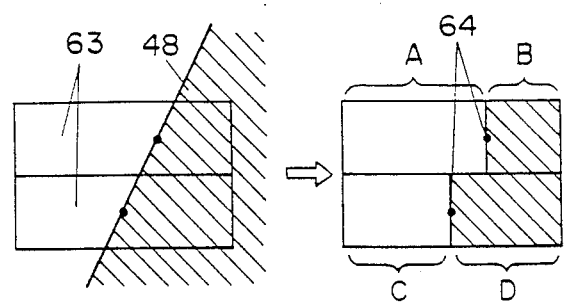
Figure 16B:
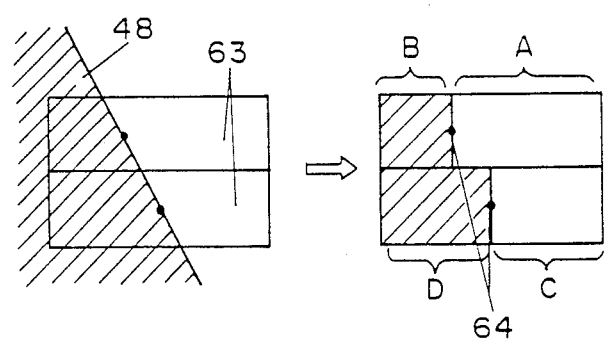

FIG. 13 shows an example of the detection of a pattern angle according to the above method. Referring to FIG. 13, a block 13a shows an image of a pattern 48 which is formed on the light receiving surface of an image pick-up array by transmitted light, or is formed by scanning a specimen surface with a single photodetector for receiving the transmitted light, and a block 13b shows 3×3 picture elements including a central picture elements 45 for detecting the pattern angle of the pattern 48. A block 13c shows respective outputs of the picture elements shown in the block 13b. It is to be noted that the saturation output of a picture element is supposed to be 100 and the actual output of the picture element is normalized on the basis of the saturation output thereof. A block 13d shows the sum of the outputs of three picture elements arranged in an X-direction, and the above sum corresponds to the output of the picture element of FIG. 12b. A pattern angle $\theta$ can be determined from the sum of outputs of three picture elements arranged in one of two adjacent rows and the sum of outputs of three picture elements arranged in the other row. A block 13i shows that the pattern angle calculated from the values of the block 13d is used as a pattern angle $\theta$. When the outputs of picture elements in two upper rows and the outputs of picture elements in two lower rows are used, a pattern angle can be detected, even when the image of a corner of the pattern appears on the central one 65 of the 3×3 picture elements as shown in FIG. 14. In a case where, unlike the arrangement of FIG. 12a, the image of the pattern edge 48 is inclined at a small angle to the long side of the picture element 63 as shown in FIGS. 15a and 15b, the determination of pattern angle by the above calculation is not accurate. Hence, in addition to a pattern angle $\theta_1$ calculated from the sum of outputs of three picture elements arranged in an X-direction, another pattern angle $\theta_2$ is calculated from the sum of outputs of three picture elements arranged in a Y-direction. The pattern angles $\theta_1$ and $\theta_2$ thus obtained are used as follows. That is, when the angles $\theta_1$ and $\theta_2$ lie in ranges $0° \leq |\theta_{1,2}| < 45°$ and $135° \leq |\theta_{1,2}| < 180°$, the angle $\theta_1$ is used as a pattern angle $\theta$. When the angles $\theta_1$ and $\theta_2$ lie in a range $45° \leq |\theta_{1,2}| < 135°$, the angle $\theta_2$ is used as the pattern angle $\theta$. However, there is a case where each of two adjacent picture elements has the same output for two arrangements of the image of the pattern 48, as shown in FIGS. 16a and 16b. In order to discriminate the two arrangements from each other, a decision process shown in FIG. 13 is used. That is, it is judged whether or not the sum of the outputs of three picture elements in the leftmost column is greater than the sum of the outputs of three picture elements in the rightmost column. When the sum in the leftmost column is greater than that in the rightmost column, it is judged that the image of the pattern 48 is arranged as shown in FIG. 16a. When the sum in the leftmost column is smaller than that in the rightmost column, it is judged that the image of the pattern 48 is arranged as shown in FIG. 16. It is needless to say that the outputs of two picture elements 63 shown in FIGS. 16a and 16b are given by $V_o \propto A/(A+B)$ and $V_o \propto C/(C+D)$.

When the outputs of picture elements $P_{11}$ to $P_{33}$ arranged as shown in FIG. 17 are expressed by $V_{11}$ to $V_{33}$, a pattern angle $\theta$ at a central picture element $P_{22}$ is given as follows:

$$\left.\begin{array}{l}\theta = \tan^{-1}\left(\sum_{i=1}^{3} V_{1i} - \sum_{i=1}^{3} V_{2i}\right) \\ \text{or} \\ \theta = \tan^{-1}\left(\sum_{i=1}^{3} V_{2i} - \sum_{i=1}^{3} V_{3i}\right)\end{array}\right\} \begin{array}{l}\sum_{i=1}^{3} V_{i1} \geqq \sum_{i=1}^{3} V_{i3} \\ , 0'' \leqq |\theta| \leqq 45°\end{array}$$

$$\left.\begin{array}{l}\theta = 90° - \tan^{-1}\left(\sum_{i=1}^{3} V_{1i} - \sum_{i=1}^{3} V_{2i}\right) \\ \text{or} \\ \theta = 90° - \tan^{-1}\left(\sum_{i=1}^{3} V_{2i} - \sum_{i=1}^{3} V_{3i}\right)\end{array}\right\} \begin{array}{l}\sum_{i=1}^{3} V_{1i} \geqq \sum_{i=1}^{3} V_{3i} \\ , 45° \leqq \theta < 135°\end{array}$$

$$\left.\begin{array}{l}\theta = 180° - \tan^{-1}\left(\sum_{i=1}^{3} V_{1i} - \sum_{i=1}^{3} V_{2i}\right) \\ \text{or} \\ \theta = 180° - \tan^{-1}\left(\sum_{i=1}^{3} V_{2i} - \sum_{i=1}^{3} V_{3i}\right)\end{array}\right\} \begin{array}{l}\sum_{i=1}^{3} V_{i1} < \sum_{i=1}^{3} V_{i3} \\ , 135° \leqq \theta < 180°\end{array}$$

$$\left.\begin{array}{l}\theta = -90° + \tan^{-1}\left(\sum_{i=1}^{3} V_{1i} - \sum_{i=1}^{3} V_{2i}\right) \\ \text{or} \\ \theta = -90° + \tan^{-1}\left(\sum_{i=1}^{3} V_{2i} - \sum_{i=1}^{3} V_{3i}\right)\end{array}\right\} \begin{array}{l}\sum_{i=1}^{3} V_{1i} < \sum_{i=1}^{3} V_{3i} \\ , -45° > \theta > -135°\end{array}$$

$$\left.\begin{array}{l}\theta = -180° - \tan^{-1}\left(\sum_{i=1}^{3} V_{1i} - \sum_{i=1}^{3} V_{2i}\right) \\ \text{or} \\ \theta = -180° - \tan^{-1}\left(\sum_{i=1}^{3} V_{2i} - \sum_{i=1}^{3} V_{3i}\right)\end{array}\right\} \begin{array}{l}\sum_{i=1}^{3} V_{i1} > \sum_{i=1}^{3} V_{i3} \\ , -135° \geqq \theta > -180°\end{array}$$

In the above explanation, a pattern has been detected by using transmitted light. Alternatively, the pattern may be detected by other illumination methods.

Next, explanation will be made of the operation of the spatial filter 26 shown in FIG. 1. Referring to FIG. 1, the laser device 5 is mounted in the oblique illumination unit 9 by the setting means 8. The linearly-polarized light 74 emitted from the laser device 5 passes through the beam expander 6 and the focusing lens 7, and then impinges on the photo-mask 36 at an incident angle i. Light reflected and diffracted from the photo-mask 36 passes through the objective lens 10 and the relay lens 12, and is then focused on the spatial filter 26. That is, the real image of the light source of the linearly-polarized light is formed on the spatial filter 26 by the beam expander 6, the focusing lens 7, the objective lens 10 and the relay lens 12. In this case, the Fraunhofer diffraction image of the pattern 48 provided on the photo-mask 36 is formed in a plane which contains the spatial filter 26. The plane of polarization of the linearly-polarized light 74 is made perpendicular to the plane of incidence defined by the linealy-polarized light 74 and an optical axis 75, to obtain P-polarized light, or is made parallel to the plane of incidence to obtain S-polarized light.

The above optical arrangement may be modified as follows. That is, the diameter dp of the light beam incident upon the focusing lens 7 is put in a range from 0.5 to 2 mm and the distance Lp between the focusing lens 7 and the photo-mask 36 is put in a range from 30 to 100 mm, to form the image of the light source of the above light beam on the photo-mask 36. Further, the spatial filter 26 is disposed in a Fourier transform plane which is formed only by the objective lens 10 and the relay lens 12. According to this optical arrangement, light rays incident upon the photo-mask 36 are substantially parallel to each other, and hence it can be considered that the light rays are Fourier-transformed only by the objective lens 10 and the relay lens 12. In this case, an illuminated portion on the photo-mask 36 has the form of an ellipse, and the length $a_i$ of the minor axis of the ellipse is given by the following equation:

$$a_i = 1.22 \cdot \lambda \cdot Lp/dp \ldots \qquad (1)$$

where $\lambda$ indicates the wavelength of the incident light ray. The length $a_i$ is determined in accordance with a light intensity necessary for the detection of a foreign substance and an area to be illuminated. In the present embodiment, the beam diameter dp is made equal to 1 mm and the distance Lp is made equal to 50 mm, to make the length $a_i$ equal to 40 μm.

In the scattered light detection unit 16, the images of the pattern 48 and the foreign substance 49 which exist on the photo-mask 36, are formed on the one-dimensional pick-up device 15 by the objective lens 10 and the relay lenses 12 and 38.

Further, the spatial filter 26 is placed in an image formation plane, on which the image of the light source of the beam 74 is formed by the beam expander 6, the focusing lens 7, the relay lens 12 and the objective lens 10. The analyzer 13 (that is, a polarization filter) is disposed at substantially the same position as the spatial filter 26.

The plane of polarization of the analyzer 13 is directed so that the analyzer 13 intercepts the light beam 74. That is, for the S-polarized light beam, the plane of polarization of the analyzer 13 is made perpendicular to the above-mentioned plane of incidence. For the P-polarized light beam, the plane of polarization of the analyzer 13 is made parallel to the plane of incidence. The analyzer 13 may be disposed at a desired position between the photo-mask 36 and the one-dimensional solid state pick-up device 15.

Further, the spatial filter 26 may be disposed at a position which exists between the photo-mask 36 and the objective lens 10 and is close to the objective lens 10. The reason for this is as follows. The light beam 74 is substantially formed of parallel light rays and the pattern 48 on the photo-mask 36 is very fine. Accordingly, the Fraunhofer diffraction image of the pattern can be formed without using the objective lens 10 and others. In a case where a filmy foreign substance is to be detected, however, it is desirable that an optical system for detecting the filmy foreign substance does not contain the spatial filter 26.

In a case where a collective lens including the relay lens 12 is used as the objective lens 10 and the image of the light source of the beam 74 is formed within the objective lens 10 by the beam expander 6, the focusing lens 7 and the objective lens 10, it is required to dispose the spatial filter 26 at the image formation position existing behind the relay lens 12. Further, a Fourier transform lens may be used as the relay lens 12. In this case, the Fourier transform image of the pattern 48 becomes sharp, and thus the light from the pattern 48 can be intercepted effectively by the spatial filter.

The interference filter 14 is used for intercepting light from the transmitted-light generating illumination unit 26, and thus can extract only the light from the laser device 5.

Next, the shape of the spatial filter 26 will be explained, with reference to FIGS. 74 to 88. The shape of the spatial filter 26 is to be appropriately determined in accordance with the method of illumination and the state of polarization of light incident on the spatial filter.

Figure 74:
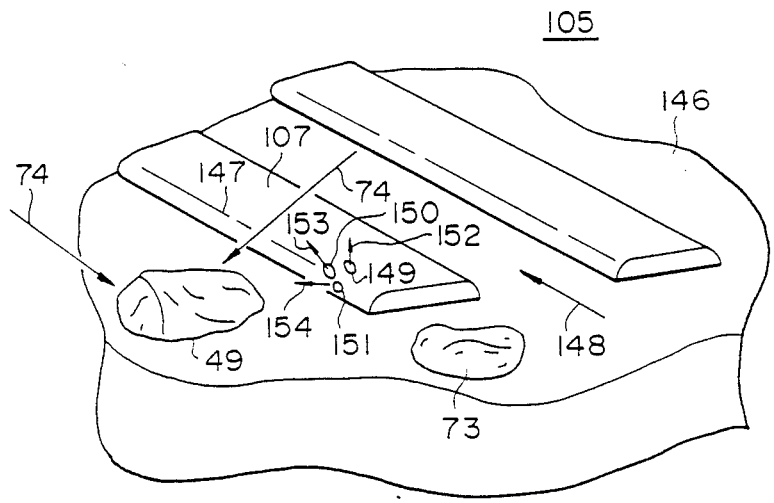
FIG 74 is a perspective view showing a portion of a photo-mask.
Figure 75:
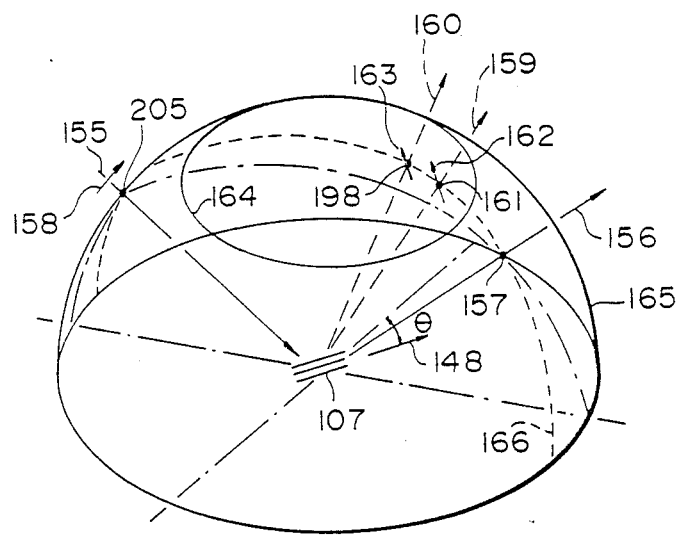
FIG. 75 is a perspective view showing diffracted light from a circuit pattern.

At first, explanation will be made of the behavior of illumination light. FIG. 74 is an enlarged view of a photo-mask 105. Referring to FIG. 74, a pattern 107 having an edge 147 parallel to a direction 148 is formed on a substrate 146. The pattern 107 and the substrate 146 are made of chromium oxide and $SiO_2$, respectively. FIG. 75 is a sketch showing a positional relation among light 155 incident on the photo-mask 105, diffracted light rays 159 and 160 from the pattern 107 parallel to the direction 148, and the aperture 164 of the objective lens 10. In FIG. 75, reference numerals 158, 162 and 163 designate the planes of polarization. Now, let us suppose a spherical surface 165 inscribed with the aperture 164 of the objective lens 10. The planes of polarization 162 and 163 of the diffracted light rays 159 and 160 are the planes of polarization at the intersections 161 and 198 of the spherical surface 165 and the diffracted light rays 159 and 160. Further, a circle 166 on the spherical surface 165 passes through the intersections 161 and 198.

Figure 76:
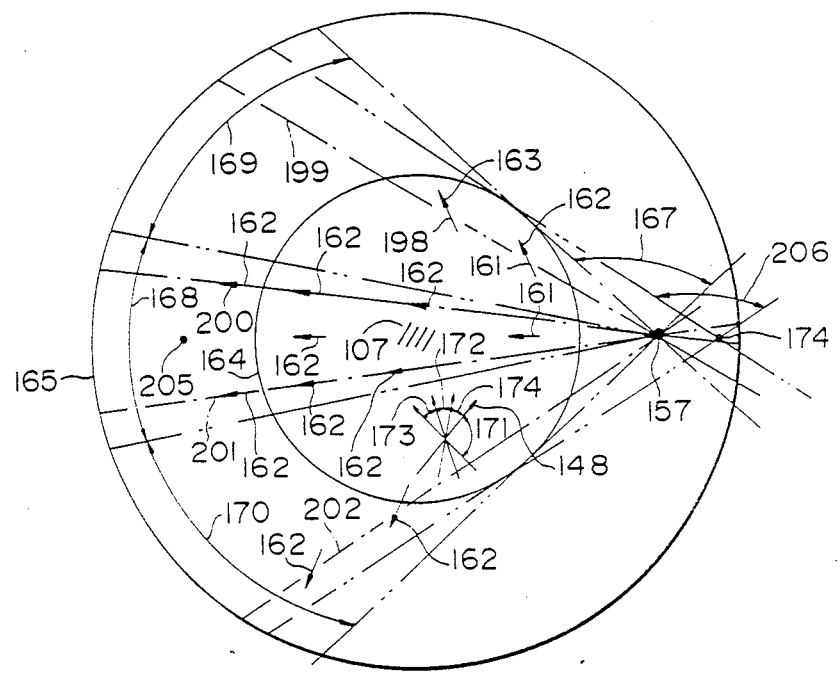
FIGS. 76 and 78 are plan view showing diffracted light from various circuit patterns.

FIG. 76 is a plan view of the sketch of FIG. 75. In FIG. 76, that circle on the spherical surface 165 which passes through the intersections of the spherical surface 165 and the diffracted rays corresponding to one of four pattern directions, is indicated by one of four straight lines 199 to 202. Further, the intersection of the incident light 155 and the spherical surface 165 and the intersection of the outgoing light 156 and the spherical surface 165 are indicated by points 205 and 157, respectively.

As described in the above-referred article having the Japanese title corresponding to "Analysis of the Light Reflected from the Micro Patterns on the LSI Wafers" (Trans. of the Society of the Instrument and Control Engineers, Vol. 21, No. 8, pages 86 to 92), when linearly-polarized light impinges on a specimen having a refractive index n at an incident angle i, the state of polarization of the reflected light from the specimen is given by the following equation:

$$(R_S, R_P) = (S(i)E_S, P(i)E_P) \ldots \qquad (2)$$

where $E_S$ and $E_P$ indicate the intensities of S- and P-polarized components of the incident light, $R_S$ and $R_P$ indicate the intensities of S- and P-polarized components of the reflected light, and S(i) and P(i) are given by the following equations:

$$\left.\begin{array}{l} S(i) = -\sin(i - i')/\sin(i + i') \\ P(i) = \tan(i - i')/\tan(i + i') \\ n\sin i' = \sin i \end{array}\right\} \qquad (3)$$

When P-polarized light (namely, linearly-polarized light having the electric field vector parallel to the plane of incident) impinges upon the photo-mask 105, the plane of polarization 162 of the diffracted light ray 159 at the intersection 161 can be calculated from the equations (2) and (3). In the above calculation, it is supposed that, as shown in FIG. 74, the edge 147 of the pattern 107 is formed of three planes 149, 150 and 152 having normal vectors 152, 153 and 154, and the reflection from each of the above planes is calculated. That is, the direction and the plane of polarization of the reflected light from each of the planes 149 to 151 for a case where the P-polarized light impinges on the planes 149 to 151, are calculated by the equation (2), to be used as the direction and the plane of polarization 162 of the diffracted light ray 159. The planes of polarization 162 thus obtained are indicated by arrows 162 in FIG. 76.

Now, the interception of diffracted light from the pattern will be explained below. The diffracted light from the pattern can be intercepted effectively by setting the incident angle i of the incident light 155 appropriately and by using the spatial filter 26 and the analyzer 13.

Referring again to FIG. 76, diffracted light within an angular range 167 does not pass through the aperture 164 of the objective lens 10. That is, when the incident angle i of the incident light is set so that the diffracted light from the pattern lies in the angular range 167, the diffracted light is intercepted. When the incident angle i is made large, the outgoing point 157 moves to a point 174 which is farther away from the aperture 164 than the point 157, and thus the diffracted light within an angular range 206 wider than the angular range 167 is intercepted.

Further, by setting the incident angle i appropriately, the diffracted light from the pattern parallel to a direction within an angular range 171 of FIG. 76 such as the pattern parallel to the direction 148 perpendicular to the circle 166 can be intercepted.

As shown in FIG. 76, the plane of polarization of the polarized light within an angular range 168 is substantially parallel to the plane of incidence. Meanwhile, the plane of polarization of the polarized light within angular ranges 169 and 170 is not parallel to the plane of incidence. Hence, the diffracted light within the angular range 168 is intercepted by the polarization filter (namely, analyzer) 13, and the diffracted light within angular ranges 169 and 170 is intercepted by the spatial filter 26.

Figure 77:
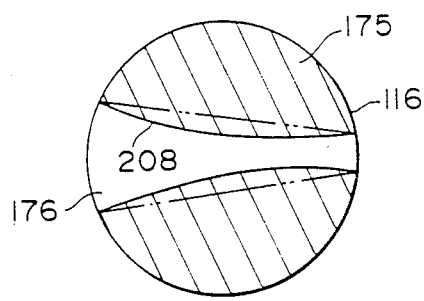
FIGS. 77, 79 to 81, 85, 86 and 88 are plan views showing various spatial filters.

FIG. 77 shows the shape of the spatial filter 26. Referring to FIG. 77, the spatial filter 26 includes a light intercepting portion 175 and a light transmitting portion 176. An edge 208 pf the spatial filter 26 has the form of a curved line for the reason that the aperture 164 is in a plane, and the locus of the intersection of the diffracted light 159 and the aperture 164 forms a curved line. The aperture 164 lies in the Fourier transform plane, and hence the shape of the spatial filter 26 is determined on the basis of the intensity distribution of the diffracted light at the aperture 164. That is, the shape of the spatial filter 26 is made similar to the cross-sectional shape of the diffracted light beam at the aperture 164. At this time, it is to be noted that the aperture 164 is formed of a plane.

The diffracted light in the angular range 168 is caused by the pattern parallel to a direction within an angular range 172, and the diffracted light in the angular ranges 169 and 170 is caused by the pattern parallel to a direction within angular ranges 173 and 174.

As can be seen from the above explanation, the diffracted light from each of patterns having various directions can be intercepted by setting the incident angle i appropriately, setting the plane of polarization of the polarization filter (namely, analyzer) 13 appropriately and selecting the shape of the spatial filter 26 appropriately.

Meanwhile, the planes of polarization of scattered light rays from a foreign substance are not parallel, though the planes of polarization of diffracted light rays from a pattern are parallel to each other. Accordingly, the scattered light within the angular range 168 may have the plane of polarization which is not parallel to the plane of polarization 172, and hence can not pass through the filters 13 and 26. The plane of polarization of scattered light from a foreign substance is discussed on pages 652 to 656 of a publication entitled "Principle of Optics" by Born and Wolf.

Figure 78:
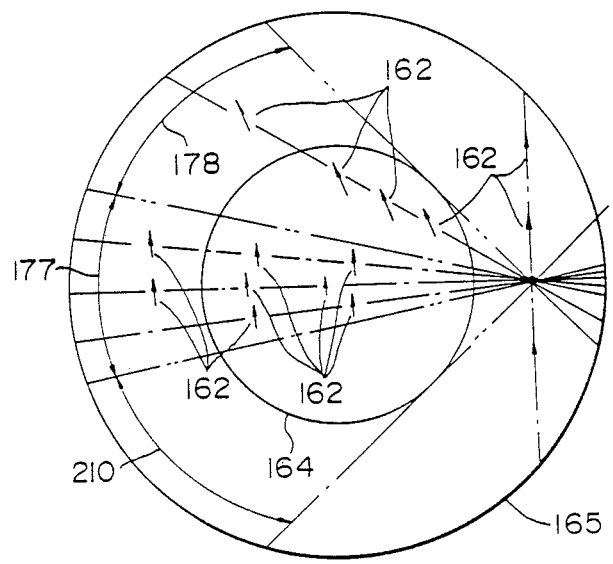

FIG. 78 shows the plane of polarization of diffracted light from the pattern for a case where S-polarized light (namely, linearly-polarized light having the electric field vector perpendicular to the plane of incidence) impinges on the photo-mask. In this case, the diffracted light within angular ranges 178 and 210 is intercepted by the same spatial filter as shown in FIG. 77, and the diffracted light within an angular range 177 is intercepted by rotating the plane of polarization of the analyzer 13 for the diffracted light within the angular range 168 of FIG. 76, by an angle of 90°.

Figure 79:
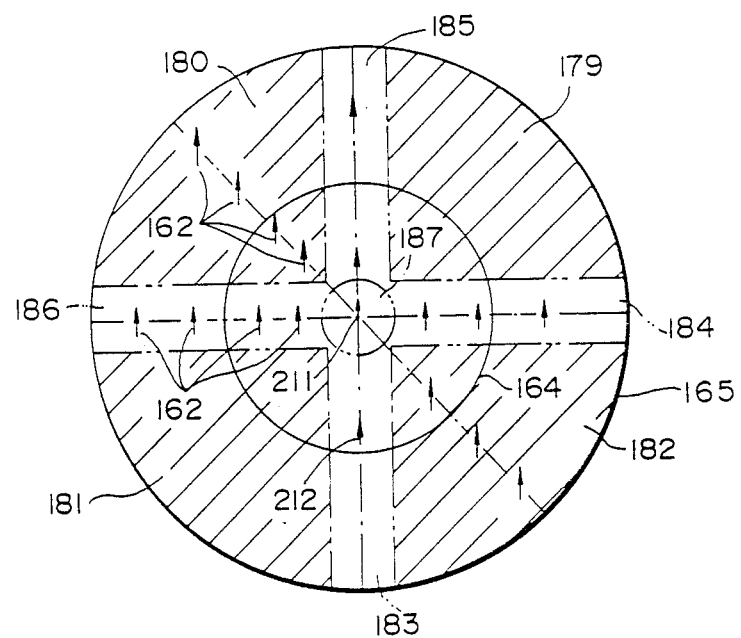
Figure 80:
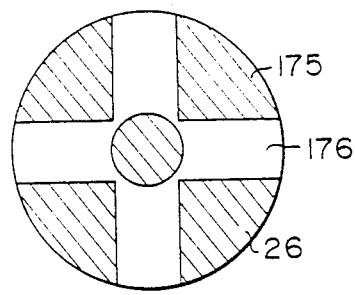

FIG. 79 shows the plane of polarization 211 of linearly-polarized light incident upon the photo-mask vertically and the plane of polarization 212 of the diffracted light from a pattern. Referring to FIG. 79, the diffracted light within angular ranges 179, 180, 181 and 182 can be intercepted by the spatial filter 26 having such a shape as shown in FIG. 80, and the diffracted light within ranges 183, 184, 185 and 186 can be intercepted by the analyzer 13.

Figure 81:
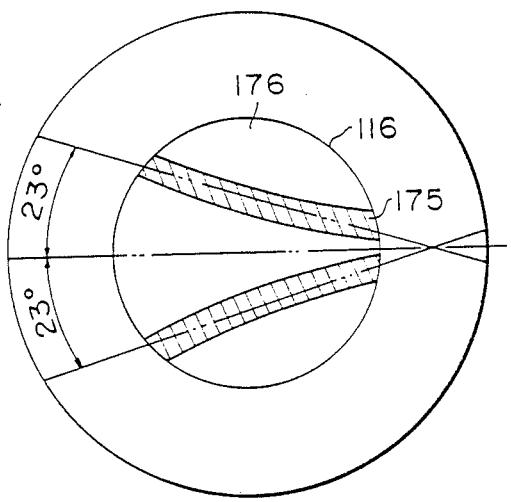

It has been found by experiments that, when linearly-polarized light impinges on the photo-mask at an incident angle of about 60°, the reflected light from the pattern having a pattern angle of about 23° is very strong. When the spatial filter having such a shape as shown in FIG. 81, the diffracted light from the pattern having a pattern angle of 23° is effectively intercepted, and the scattered light from a foreign substance can pass through the spatial filter.

Further, it has been found by experiments that when the incident angle i is made large, the quantity of the scattered light from the foreign substance increases.

Figure 73:
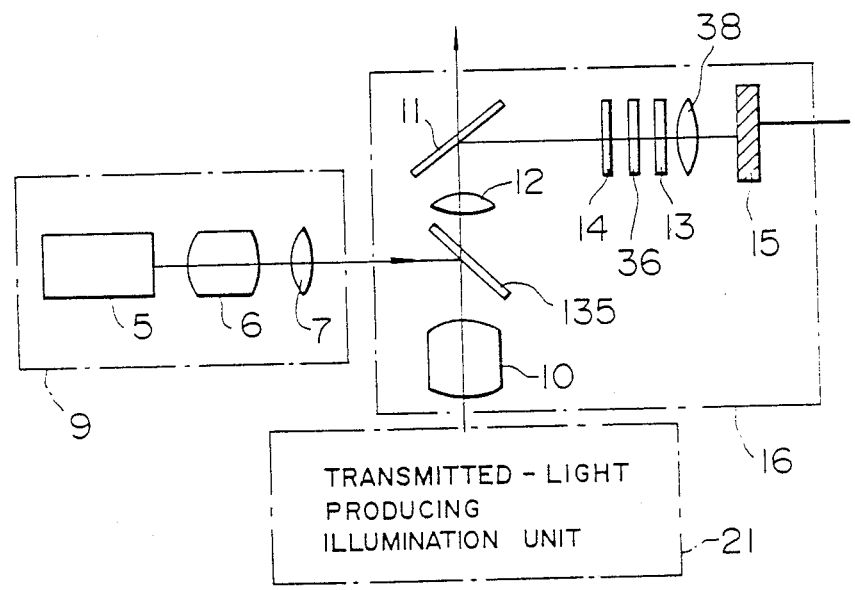
FIGS. 73 and 84 are block diagrams showing massive foreign substance detecting systems.
Figure 82:
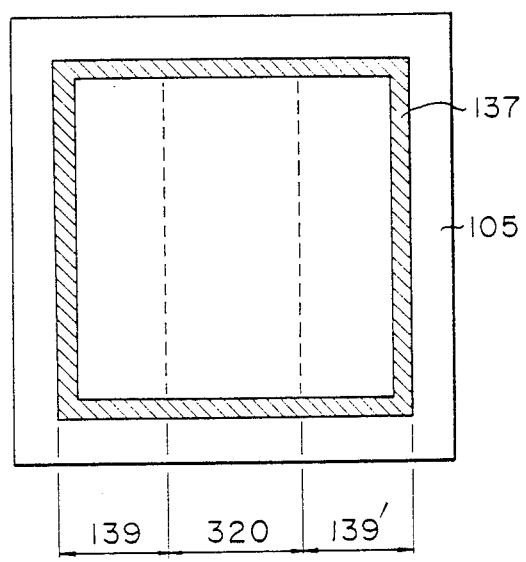
FIGS. 82 and 83 are sectional and plan views showing a photo-mask.
Figure 83:
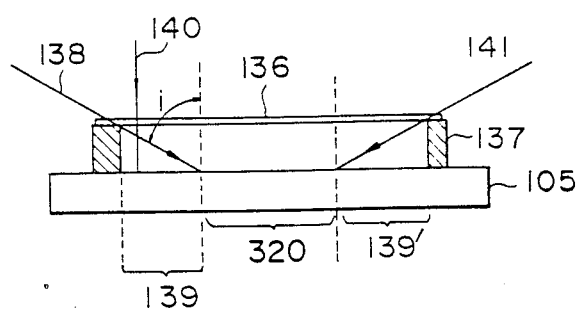
Figure 84:
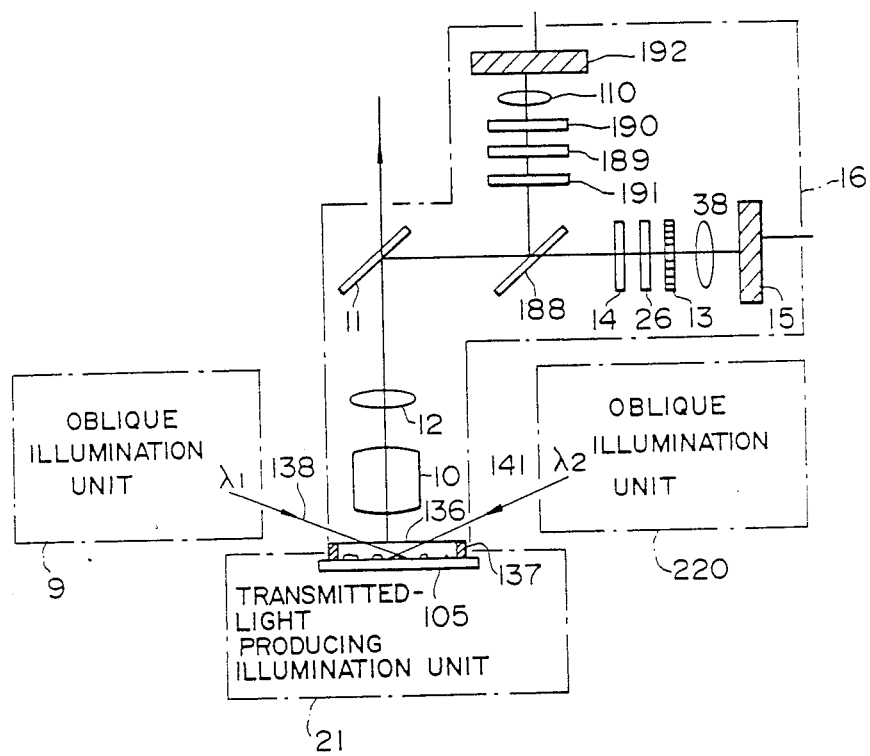

In some cases, the photo-mask 105 is provided with a pellicle structure for preventing a foreign substance from being attached to the photo-mask. As shown in FIGS. 82 and 83, the pellicle structure is made up of a thin transparent film (namely, pellicle film) 136 and a pellicle frame 137 for holding the pellicle film 136. In the above cases, when the incident angle i is made large, a wide area 139 on the photo-mask is not illuminated with incident light, since the incident light is intercepted by the pellicle frame 137. This problem can be solved by using two oblique illumination units 9 and 220. That is, the oblique illumination units 9 and 220 equal in construction are disposed so that, as shown in FIG. 83, the incident light 138 from the unit 9 and the incident light 141 from the unit 220 are substantially symmetrical with respect to the optical axis of the present embodiment. In this case, as shown in FIG. 84, the reflected light from the photo-mask is divided by a half mirror 188, and moreover a spatial filter 189, an analyzer (namely, polarization filter) 190, an interference filter 191, a relay lens 110 and a one-dimensional solid state pick-up device 192 are added to the scattered light detection unit 16 of FIG. 73. Further, the spatial filter of FIG. 81 and the turned-up version thereof are used as the spatial filters 26 and 189 of FIG. 84, respectively. In order to inspect the area 139 of FIG. 83, the incident light 141 is used, and the reflected light from the photo-mask is detected by the pick-up device 192. Thus, all the area under the pellicle film 136 can be inspected.

Alternatively, the area 139 of FIG. 83 may be inspected by rotating the photo-mask round the optical axis by an angle of 180°, without using the oblique illumination unit 220.

Further, the light 138 from the oblique illumination 9 is made different in wavelength from the light 141 from the oblique illumination unit 220. That is, the light 138 has a wavelength $\lambda_1$ and the light 141 has a wavelength $\lambda_2$. In this case, the wavelengths $\lambda_1$ and $\lambda_2$ can be separated from each other by using a wavelength separation mirror in place of the half mirror 188, and moreover the light sources in the oblique illumination units 16 and 220 are not required to be alternately turned off.

The use of two oblique illumination units produces another effect. That is, as shown in FIG. 74, an actual, fine foreign substance is not symmetrical with respect to the center axis thereof. Accordingly, the reflecting surface of the foreign substance for the incident light 138 is different in size and shape from the reflecting surface for the incident light 141, and hence the scattered light from the former reflecting surface is different in intensity and plane of polarization from the scattered light from the latter reflecting surface. When only one of the incident light 138 and the incident light 141 is used, there is a fear that the foreign substance is missed. When both of the light 138 and the light 141 are used, there is a fair chance for the foreign substance on an area 320 (shown in FIG. 83) to be detected by the light 138 or 141, and thus the reliability of the detection of foreign substance is enhanced.

Figure 85:
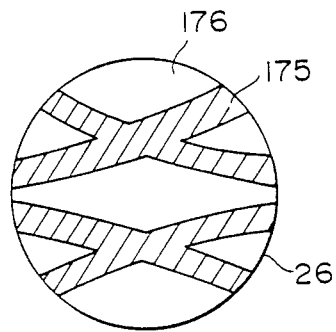

When a spatial filter shown in FIG. 85 is used, a foreign substance can be detected without requiring the members 110, 188, 189, 190, 191 and 192 in the scattered light detection unit 16.

Figure 86:
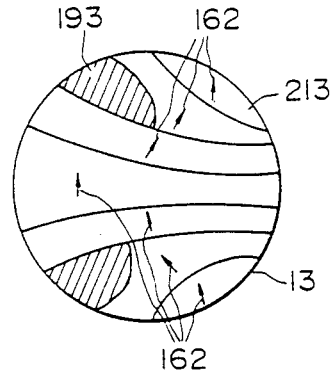

Further, when the direction of the plane of polarization of the analyzer 13 is locally varied as shown in FIG. 86 on the basis of the result of the above-mentioned calculation, the reflected light from the pattern 107 can be intercepted. In a case where the direction of the plane of polarization of the reflected light varies widely in a narrow region, however, it is preferable to use a shading plate together with the analyzer of FIG. 86. In this case, it is necessary to change the combination of polarizing plates 213 of FIG. 86 on the basis of calculation using the equation (2), since the distribution of the direction of plane of polarization of reflected light is dependent upon the materials of the pattern 107 and the substrate 146.

In the above, explanation has been made of a case where S- or P-polarized light impinges upon the photo-mask. In a case where linearly-polarized light other than the S-polarized light and the P-polarized light impinges upon the photo-mask, also, the state of polarization of the reflected light from the pattern can be calculated, and thus the polarization filter for intercepting the reflected light from the pattern can be designed.

Figure 87:
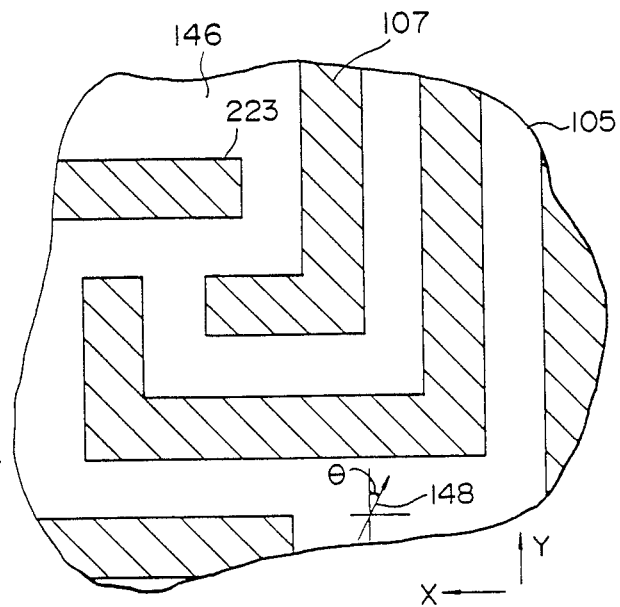
FIG. 87 is a plan view showing a circuit pattern on a photo-mask.
Figure 88:
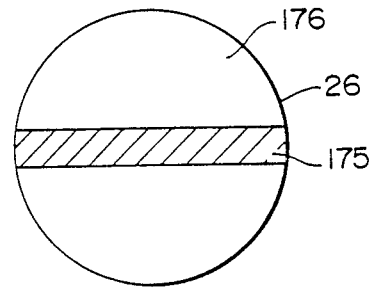

As shown in FIG. 87, the pattern 107 on an actual photo-mask 105 is often formed of pattern portions having a pattern angle equal to 0° and pattern portions having a pattern angle of 90°. In this case, it is desirable to use a spatial filter shown in FIG. 88, since the scattered light from the pattern portions having a pattern angle equal to 0° can be intercepted by a light intercepting portion 175. Further, as has been already explained, when the light from the oblique illumination unit 9 impinges upon the pattern portions having a pattern angle of 90°, the scattered light from the pattern portions does not impinge on the objective lens 10. The plane of polarization of incident light, the incident angle i, the shape of the spatial filter, and the plane of polarization of the analyzer (namely, polarization filter) are to be determined on the basis of the above facts.

Now, the detection of a filmy foreign substance will be explained below, with reference to FIGS. 1 and 18 to 22.

The transmitted-light producing illumination unit 21 of FIG. 1 operates as follows. Light emitted from a light source 17 (for example, a mercury lamp or a mercury-xenon lamp) passes through the wavelength selection filter 19, the condenser lens 18, the ring diaphragm 28 and the focusing lens 20, and then impinges upon the photo-mask. The ring diaphragm 28 is used only when a phase contrast microscope is formed as mentioned later. The transmitted light having passed through the photo-mask 36 is converted into convergent light by the objective lens 10, and then passes through the relay lens 12, the half mirror 11, the interference filter 40 for separating the transmitted light from the scattered light, the phase plate 27 and the relay lens 39. The light from the lens 39 is focused on the one-dimensional solid state pick-up device 41. The phase plate 27 is used only when the phase contrast microscope is formed. A detection signal indicative of an image of the photo-mask 36 formed by the transmitted light is sent to the differentiating/emphasizing circuit 25, to emphasize the filmy foreign substance, and the filmy foreign substance is discriminated from the pattern by the filmy foreign substance judging circuit 30, to be detected.

In a case where the filmy foreign substance is low in light intercepting ability, a multiple interference arises within the foreign substance when light passes through the foreign substance, and thus the quantity of transmitted light is decreased. Since this phenomenon is caused by interference of light, the reduction in quantity of transmitted light depends upon the wavelength of transmitted light. In order to find a foreign substance which is harmful at an exposing time, it is necessary to make the wavelength of the transmitted light for inspection equal to the wavelength of exposing light. Accordingly, the filter 19 for selecting the same wavelength as that of the exposing light is included in the illumination unit 21. It is needless to say that the filter 19 may be disposed at a desired position between the light source 17 and the photo-mask 36.

Figure 18:
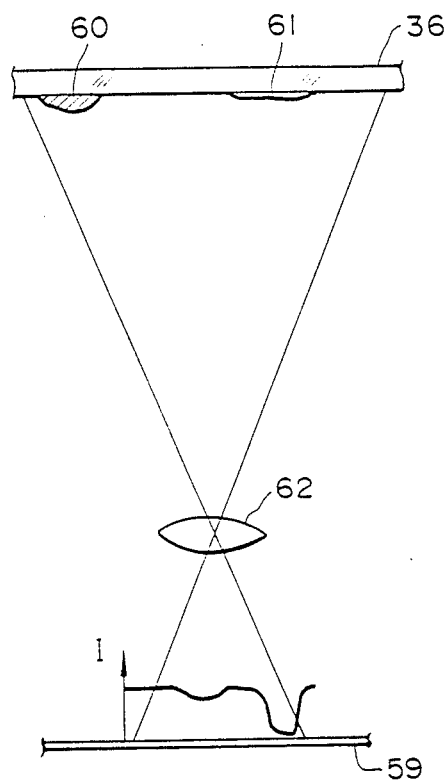
FIG. 18 is a schematic diagram for explaining how foreign substances on a photo-mask are projected onto a wafer.

Now, the defferentiating/emphasizing circuit 25 for the detection signal due to transmitted light will be explained below. Referring to FIG. 18, in a case where the photo-mask 36 is projected on a wafer 59, when a foreign substance 60 on the photo-mask 36 is high in light intercepting ability, the light intensity I on the wafer 59 is greatly reduced at a position corresponding to the foreign substance 60. That is, the highly opaque foreign substance 60 has a great influence on the projection of the photo-mask 36 on the wafer 59. When a foreign substance 61 is low in light intercepting ability, the light intensity I on the wafer 59 is reduced only a little at a position corresponding to the foreign substance 61. That is, the influence of the slightly opaque foreign substance 61 on the above projection is less than that of the highly opaque foreign substance on the projection.

Figure 19:
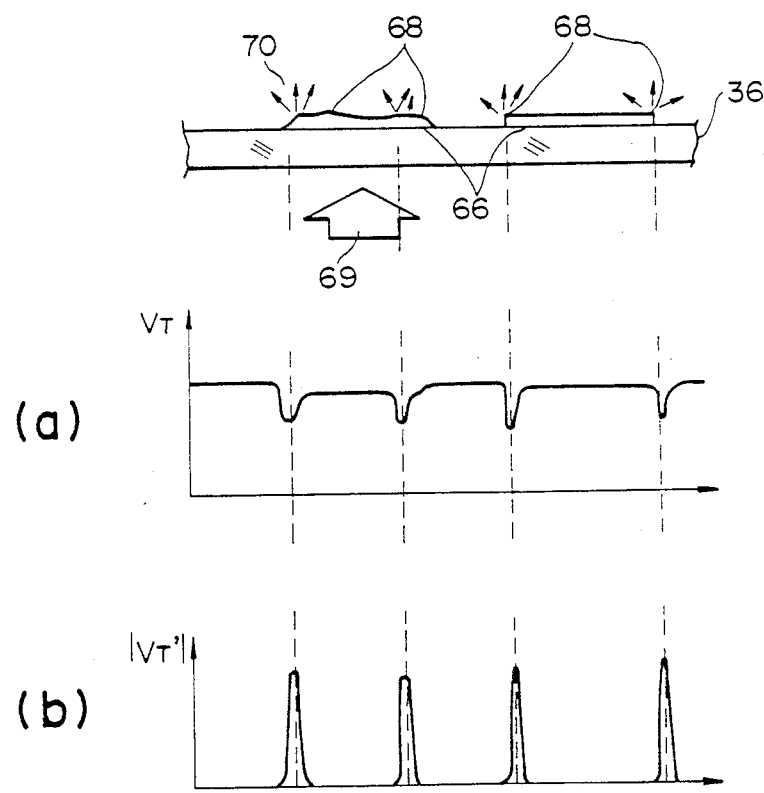
FIG. 19a and 19b show the waveform of a detection signal due to transmitted light from a photo-mask and the differentiated one of the detection signal.

It has been found by experiments that, when a slightly opaque foreign substance has fine irregularities or an edge portion, the foreign substance has a great influence on the above projection. This is because, in FIG. 19, exposing light 69 is diffracted by fine irregularities 68 and edge portions 68 as indicated by reference numeral 70, and thus the intensity of transmitted light is reduced at these positions. Accordingly, it is necessary to make the fine irregularities and edge portions clear and to detect them. Hence, the transmitted light detection unit 22 is formed of a phase contrast microscope, or a detection signal $V_T$ due to transmitted light is electrically differentiated. As shown in FIG. 19, a signal $|V_T'|$ obtained by differentiating the signal $V_T$ clearly shows the fine irregularities 68 and the edge portions 68.

Figure 20A:
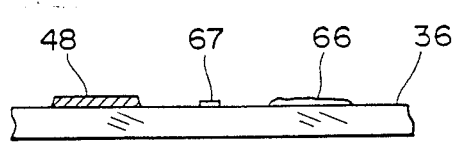
FIGS. 20a to 20f show how a circuit pattern can be detected from a detection signal due to transmitted light.
Figure 20B:
Figure 20C:
Figure 20D:
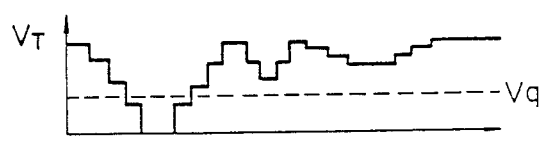
Figure 20E:
Figure 20F:
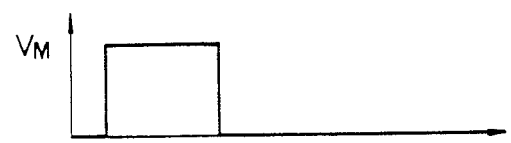
Figure 21:
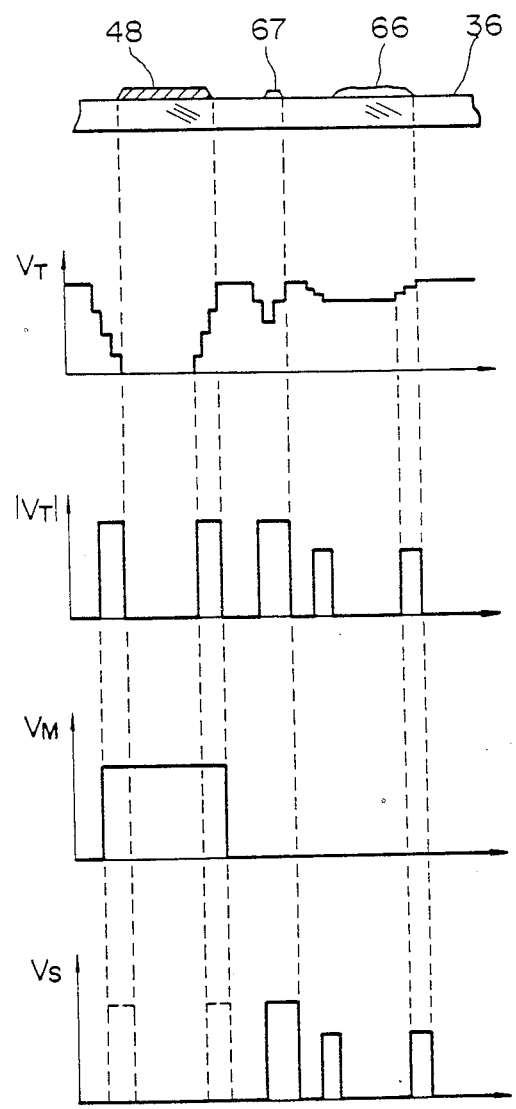
FIG. 21 shows how only foreign substances can be extracted from a detection signal due to transmitted light.

Next, explanation will be made on how a foreign substance is discriminated from the pattern. FIG. 20a shows the photo-mask 36 having a pattern 48, a large, filmy, slightly-opaque foreign substance 66 and a small, filmy, highly-opaque foreign substance 67. The pattern 48 is formed of a highly-opaque metal film, and hence the light passing through the photo-mask 36 is weakened at the pattern 48. FIGS. 20b to 20d show detection signals $V_T$ due to the transmitted light from the photo-mask of FIG. 20a. When the detection signal $V_T$ has such a waveform as shown in FIG. 20b, it is impossible to discriminate between the pattern 48 and the highly-opaque foreign substance 67 by comparing the detection signal $V_T$ with a threshold level. FIG. 20c shows a detection signal $V_T$ which has been obtained by using an optical system which is lower in resolving power than an optical system for obtaining the detection signal of FIG. 20b. FIG. 20d shows a detection signal $V_T$ which has been obtained by using a detector which is larger in size than a detector for obtaining the detection signal of FIG. 20b. As can be seen from FIGS. 20c and 20d, detection systems for obtaining the detection signals of FIGS. 20c and 20d are both low in resolving power. In the detection signals of FIGS. 20c and 20d, a reduction in signal level due to the highly-opaque foreign substance 67 is less than a reduction in signal level due to the pattern 48, and hence the foreign substances 66 and 67 can be discriminated from the pattern 48 by using an appropriate threshold level $V_n$ or $V_g$. By using a detection system having an appropriate resolving power and an appropriate threshold level, a binary signal $V_p$ shown in FIG. 2e can be extracted from a detection signal. Further, when the binary signal $V_p$ is enlarged by picture elements, a signal $V_M$ shown in FIG. 20f is obtained. Referring now to FIG. 21, when the differentiated signal $|V_T'|$ of the detection signal $V_T$ due to transmitted light is masked by the above signal $V_M$, a signal $V_S$ indicating only the foreign substances is obtained, and thus the foreign substances can be detected.

Figure 22:
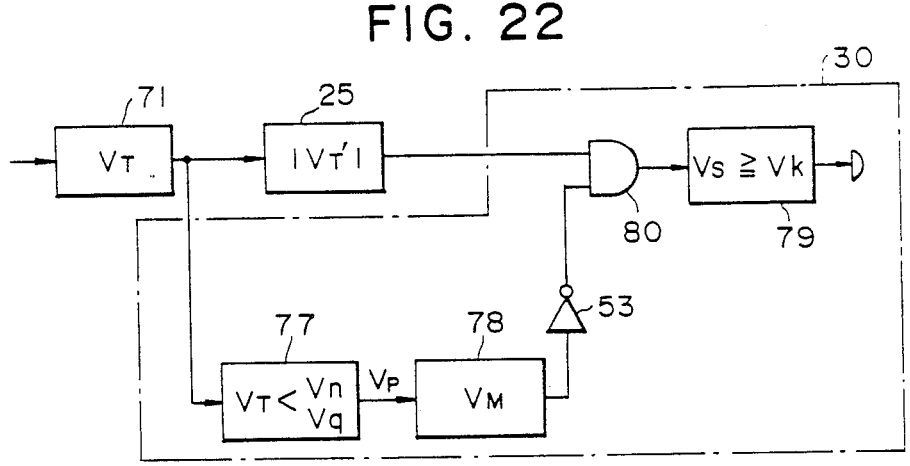
FIG. 22 is a block diagram showing a filmy foreign substance detecting circuit.

FIG. 22 shows the circuit configuration of the filmy foreign substance detecting circuit 30. Referring to FIG. 22, a detection signal $V_T$ from a transmitted-light detecting circuit 71 is differentiated by the differentiating/emphasizing circuit 25, to obtain a differentiated signal $|V_T'|$. The detection signal $V_T$ is also compared with a threshold level $V_n$ or $V_g$ by a comparator circuit 77, to obtain a binary signal $V_p$, which is applied to a picture-element enlarged circuit 78 to obtain a masking signal $V_M$. The masking signal $V_M$ is applied to one input terminal of an AND circuit 80 through an inverter 53, and the other input terminal of the AND circuit 80 is applied with the differentiated signal $|V_T'|$. That is, an output signal $V_S$ from the AND circuit 80 is the logical sum of the outputs of the differentiating circuit 25 and the inverter 59, and is not affected by the pattern. The signal $V_S$ is compared with a threshold level $V_k$ by a comparator circuit 79, to obtain a foreign substance detection signal D.

Next, explanation will be made of a case where the transmitted light detection unit 22 is formed of a phase contrast microscope.

In the transmitted-light producing illumination unit 21 of FIG. 1, light from the light source 17 impinges on the ring diaphragm 28 having a ring-shaped aperture through the condenser lens 18 and the interference filter 19, and the light from the ring diaphragm 28 impinges on the back side of the photo-mask 36 through the focusing lens 20. The transmitted light from the photo-mask 36 passes through the objective lens 10, the relay lens 12, the half mirror 11 and the interference filter 40 for intercepting light from the oblique illumination unit 9, and is then focused on the phase plate 27.

The phase contrast microscope is explained in many publications, for example, a Japanese publication entitled "OYO-KOGAKU (Applied optics)" by H. Kubota, pages 129 to 136, and hence explanation thereof will be omitted.

A filmy foreign substance to be detected by the phase contrast microscope is required to produce a detectable phase difference, that is, is required to a thickness of 10 nm or more. A thick filmy foreign substance can be detected, since variations in thickness thereof cause a phase difference. Thus, a filmy foreign substance having a thickness of 10 nm to 10 μm can be detected by the phase contrast microscope.

When the phase contrast microscope is used for detecting a filmy foreign substance, only that portion of the field of view where a phase difference is generated, that is, only the portion corresponding to the foreign substance can be made bright. Accordingly, it is not required to detect the pattern in the above-mentioned manner, and thus the system for detecting the filmy foreign substance can be simplified in structure.

Figure 23:
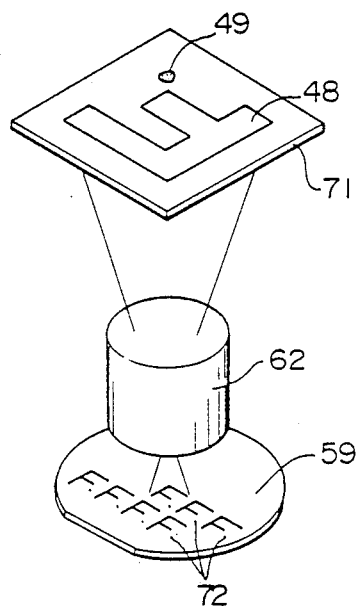
FIG. 23 is a perspective view showing the formation of a defect common to all chips.
Figure 24:
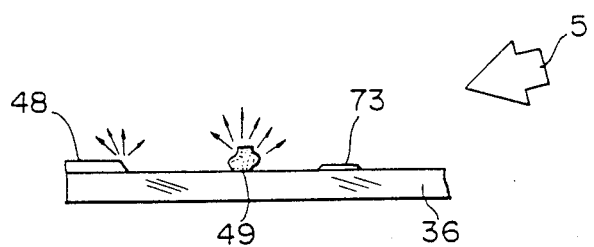
FIG. 24 is a sectional view showing a specimen irradiated obliquely with a light beam.

Incidentally, FIG. 23 shows that a foreign substance 49 on a photo-mask 71 is repeatedly projected onto a wafer 59, and FIG. 24 shows that light from the oblique illumination unit is scarcely scattered from a filmy foreign substance 73.

FIGS. 25 to 72 show examples of the circuit configuration of a foreign substance detecting apparatus according to the present invention. In FIGS. 25 to 72, like reference numerals designate like circuits or parts.

Figure 25:
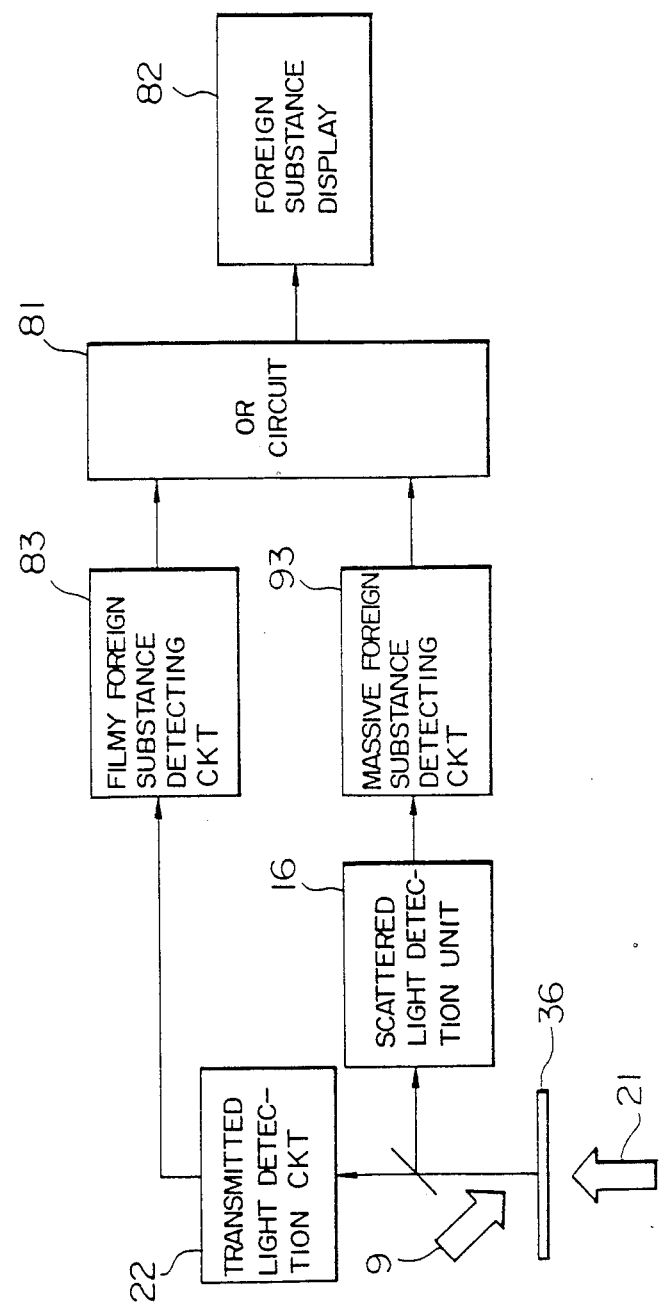
FIGS. 25 to 72 are block diagrams showing examples of the fundamental construction of a foreign substance detecting apparatus according to the present invention.

Referring to FIG. 25, a specimen (for example, photo-mask) 36 is irradiated with the light from the oblique illumination unit 9 and the light from the transmitted-light producing illumination unit 21. An image of the photo-mask 36 formed by transmitted light is converted by the transmitted light detection unit 22 into a detection signal. A filmy foreign substance detecting circuit 83 performs a differentiating/emphasizing operation for the detection signal due to transmitted light, if necessary, to detect a filmy foreign substance. An image of the photo-mask formed by scattered light is converted by the scattered light detection unit 16 into another detection signal. A massive foreign substance detecting circuit 93 detects a massive foreign substance from the detection signal due to scattered light. The filmy and massive foreign substances thus detected are displayed by a foreign substance display device 82 after the double detection of each foreign substance has been prevented by an OR circuit 81.

Figure 26:
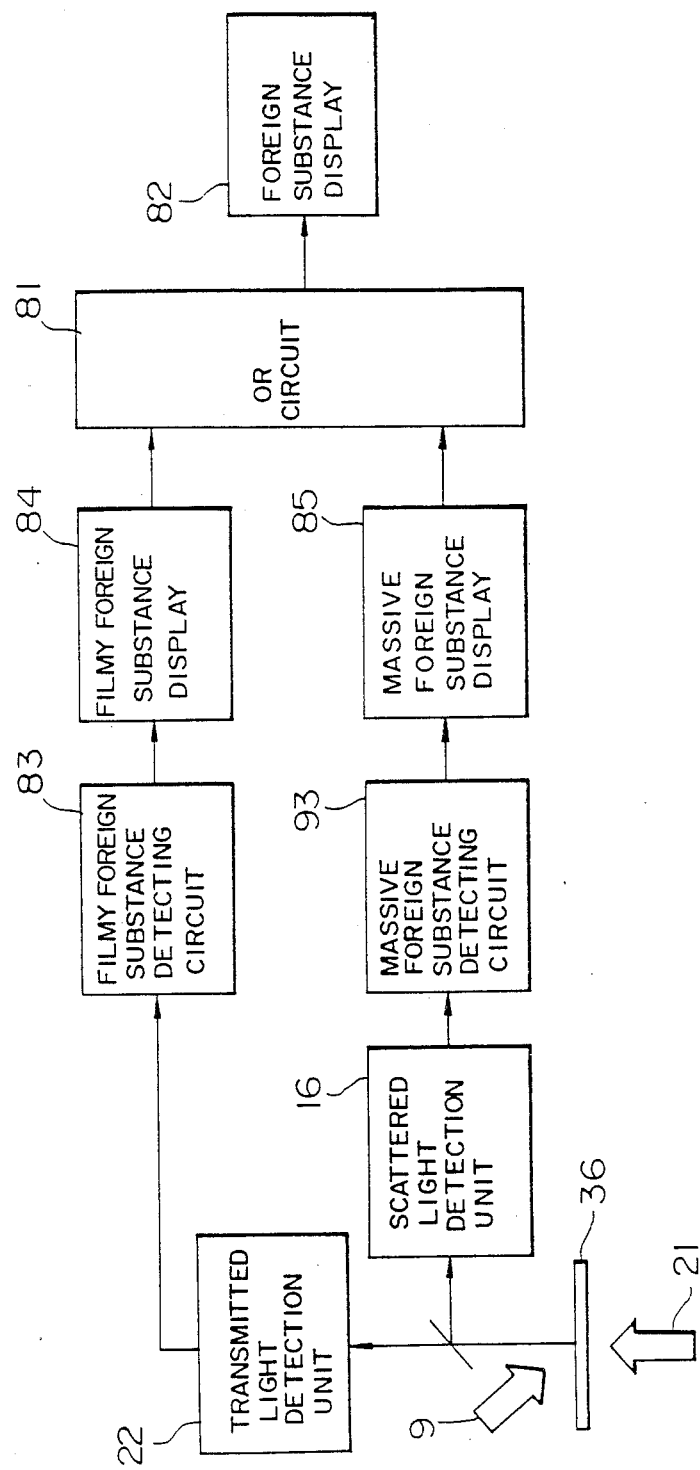

The circuit configuration of FIG. 26 is different from the circuit configuration of FIG. 25 in that the filmy foreign substance detected by the foreign substance detecting circuit 83 is displayed by a filmy foreign substance display device 84 before sent to the OR circuit 81, and the massive foreign substance detected by the massive foreign substance detecting circuit 93 is displayed by a massive foreign substance display device 85 before sent to the OR circuit 81.

Figure 27:
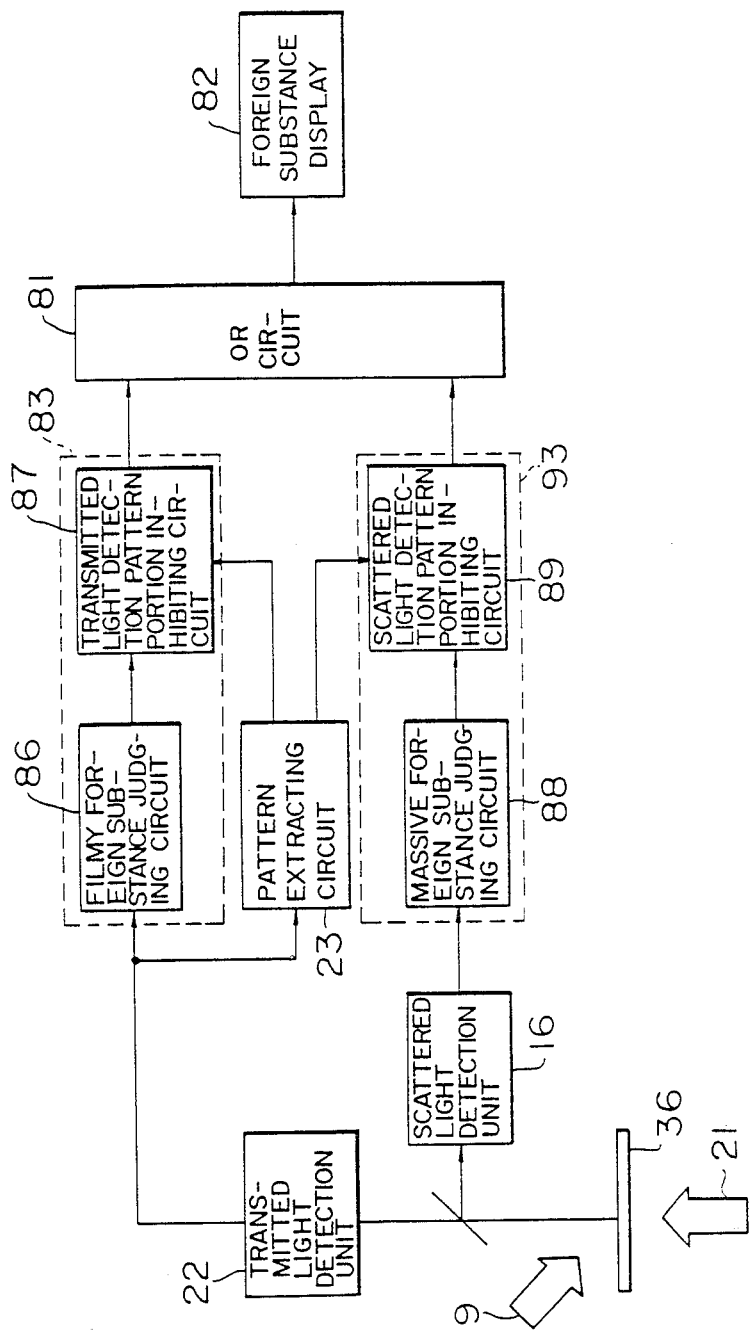

The circuit configuration of FIG. 27 is different from the circuit configuration of FIG. 25 in that the pattern extracting circuit 23 is additionally provided. In more detail, false information on a pattern portion is removed from the result of judgement of a filmy foreign substance judging circuit 86 (which includes the differentiating/emphasizing circuit 25, if necessary) by a pattern portion inhibiting circuit 87 which pattern is for detecting the transmitted light, and false information on the pattern portion due to scattered light is removed from the result of judgment of a massive foreign substance judging circuit 88 by another pattern portion inhibiting circuit 89 which pattern portion is for detecting the scattered light.

Figure 28:
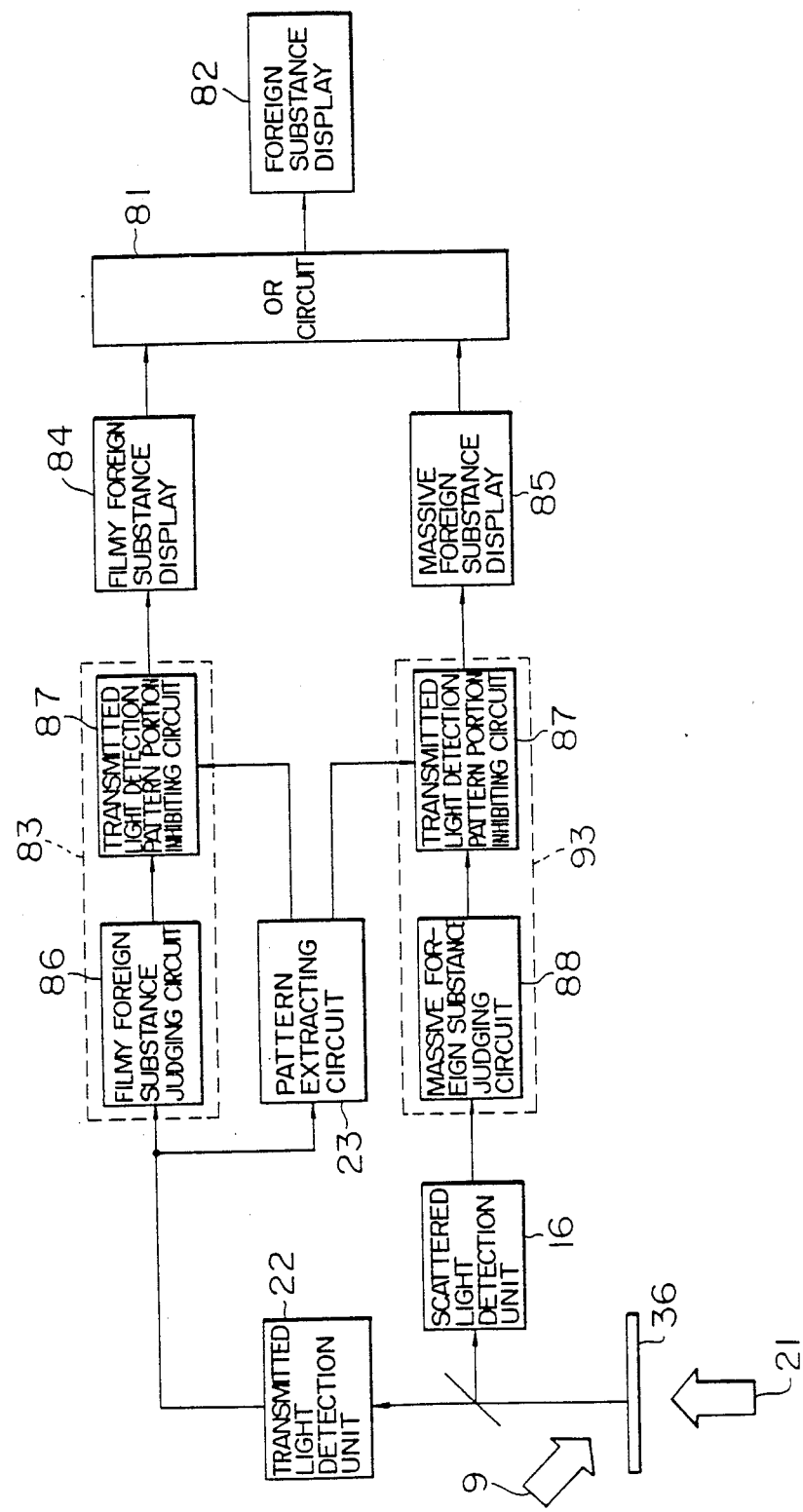

The circuit configuration of FIG. 28 is different from the circuit configuration of FIG. 26 in that the pattern extracting circuit 23 and the pattern portion inhibiting circuits 87 and 89 are provided.

Figure 29:
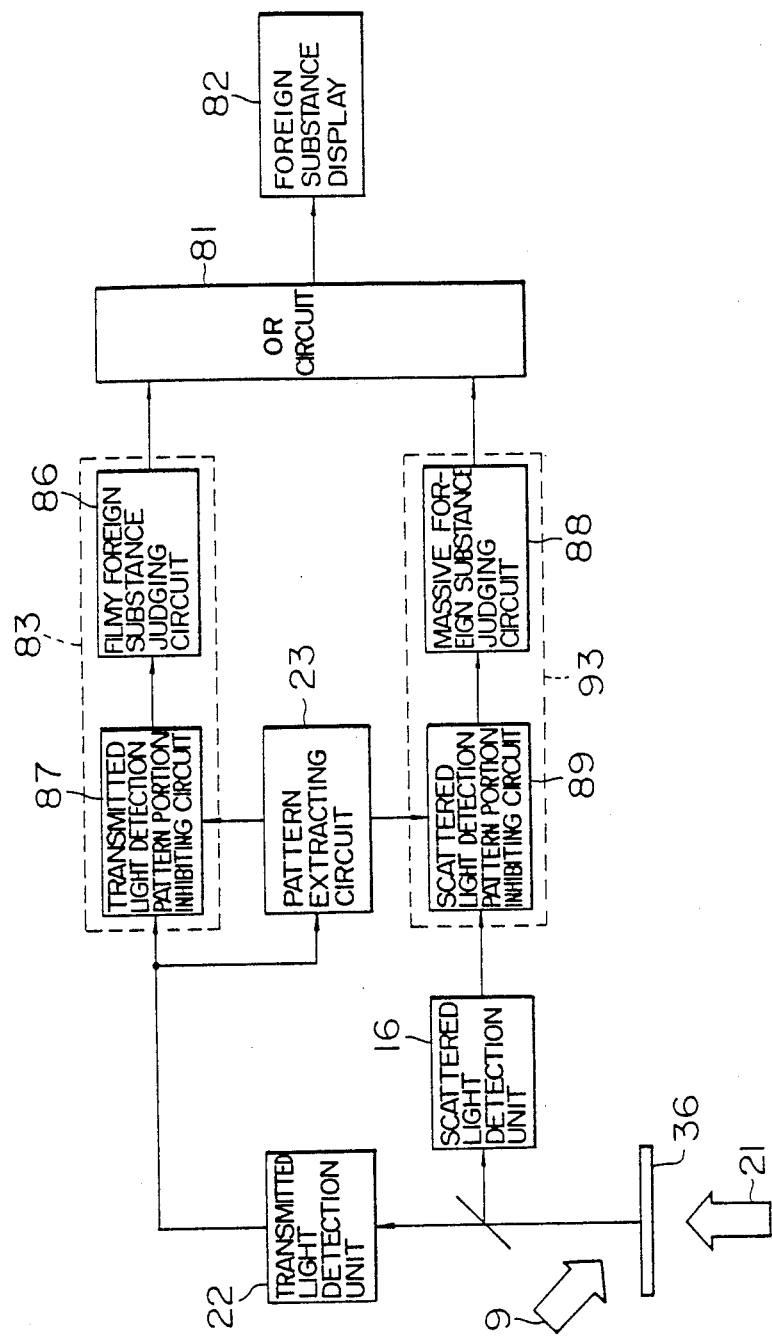

The circuit configuration of FIG. 29 is different from the circuit configuration of FIG. 27 in that the pattern portion inhibiting circuits 87 and 89 are provided before the foreign substance judging circuits 86 and 88, respectively.

Figure 30:
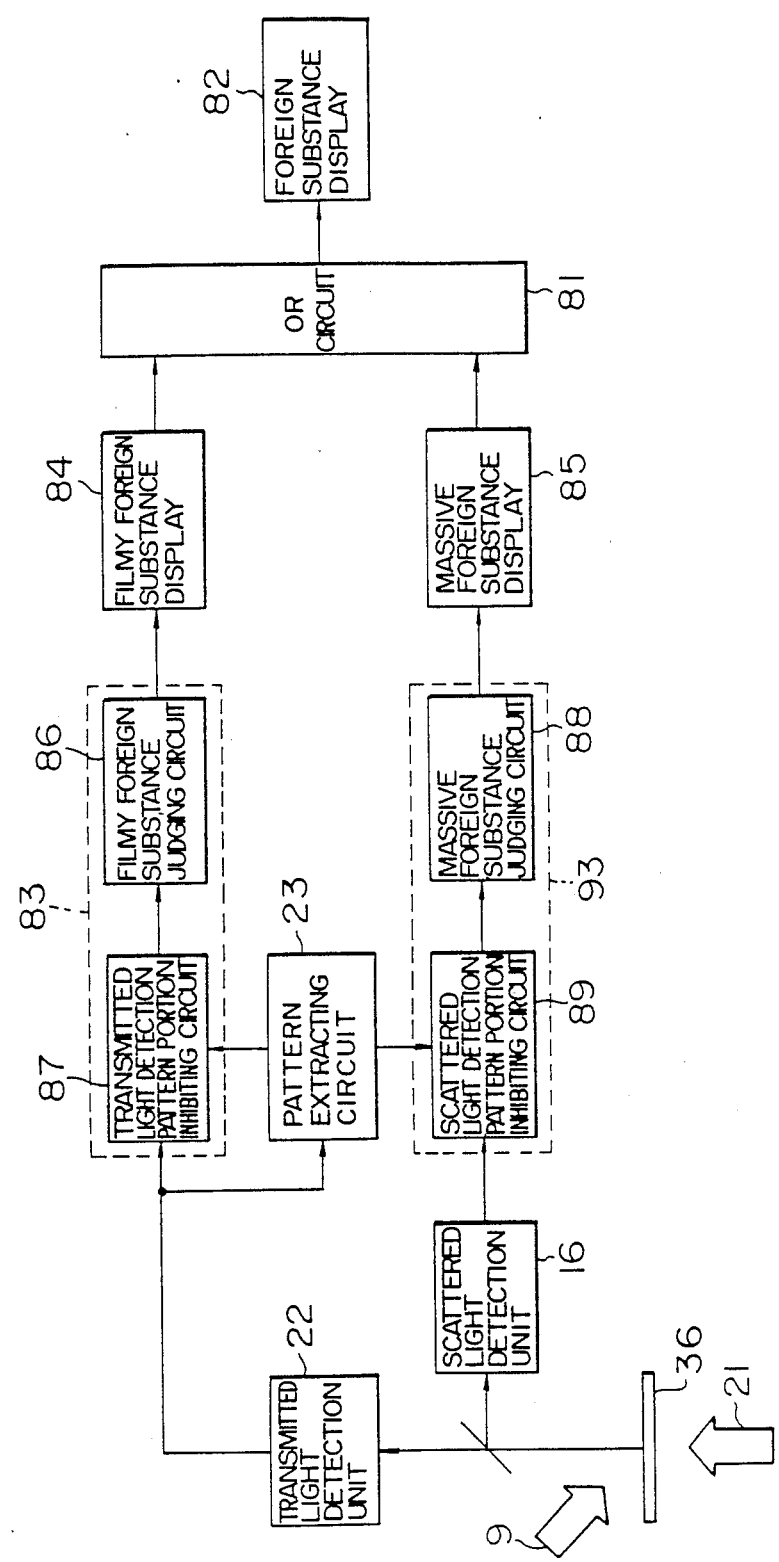

The circuit configuration of FIG. 30 is different from the circuit configuration of FIG. 28 in that the pattern portion inhibiting circuits 87 and 89 are provided before the foreign substance judging circuits 86 and 88, respectively. Alternatively, in the circuit configuration of FIG. 30, an analyzer or the combination of a spatial filter and an analyzer may be used for optically inhibiting the image of a pattern portion.

Figure 31:
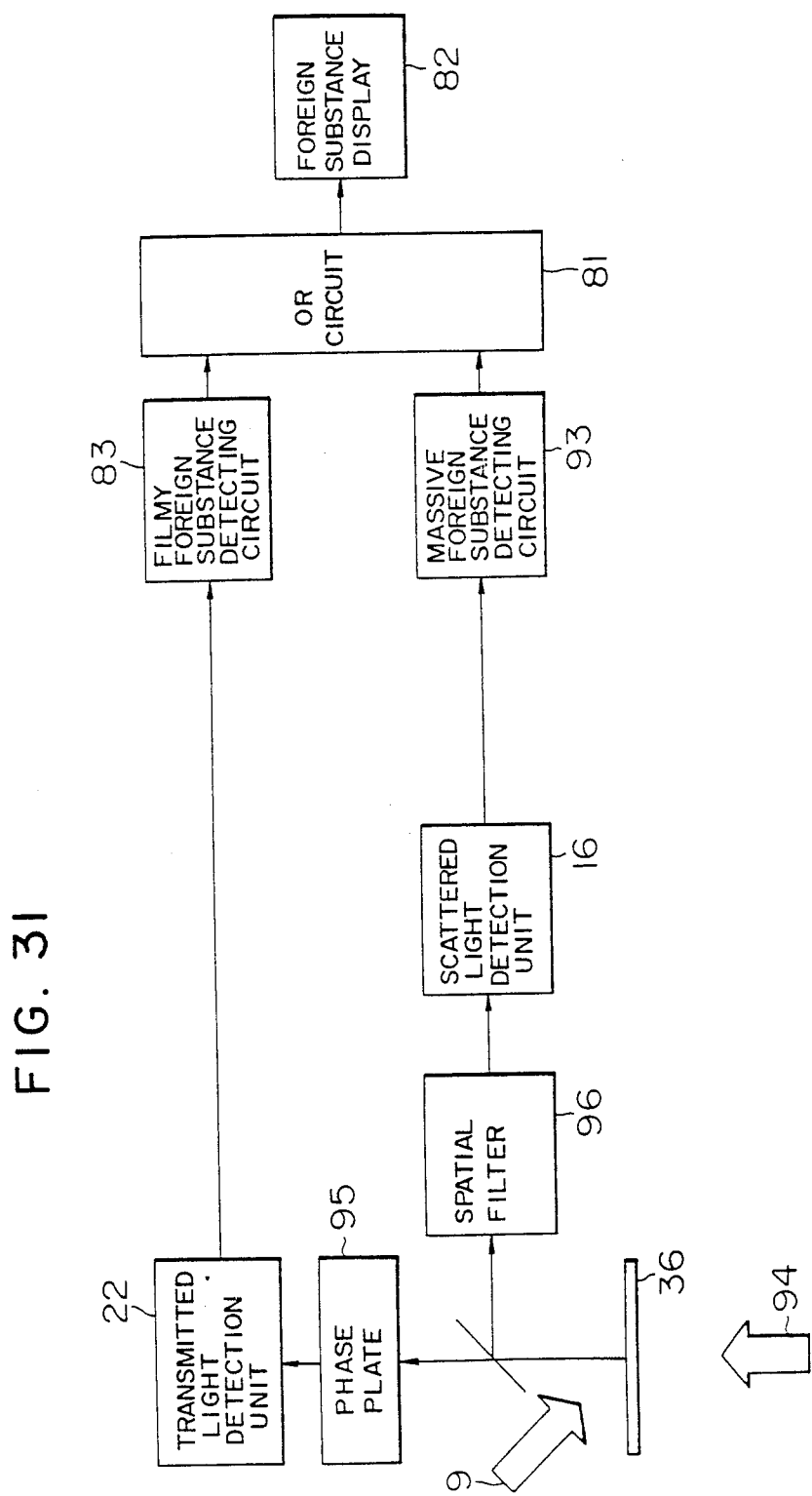
Figure 32:
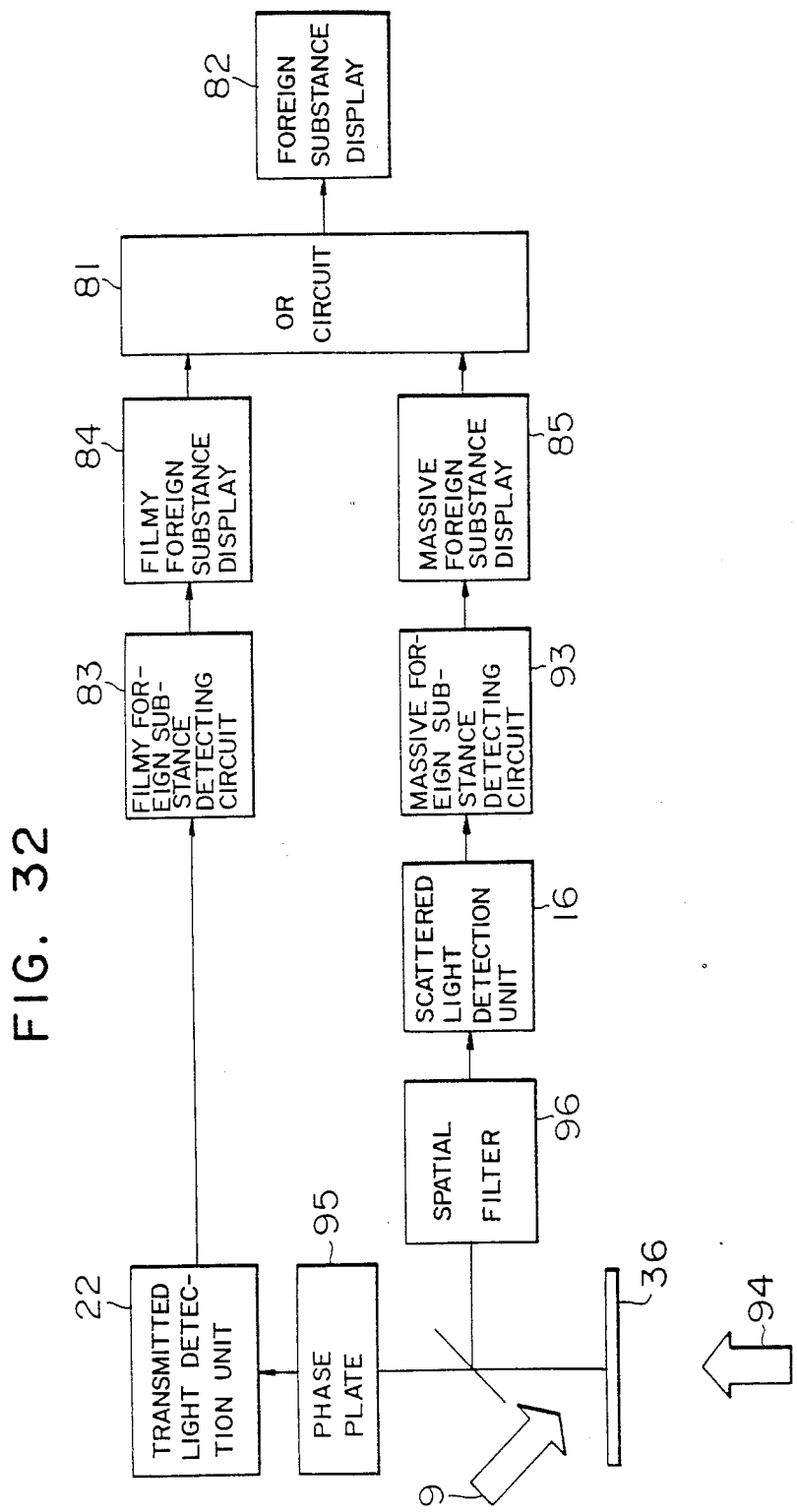
Figure 33:
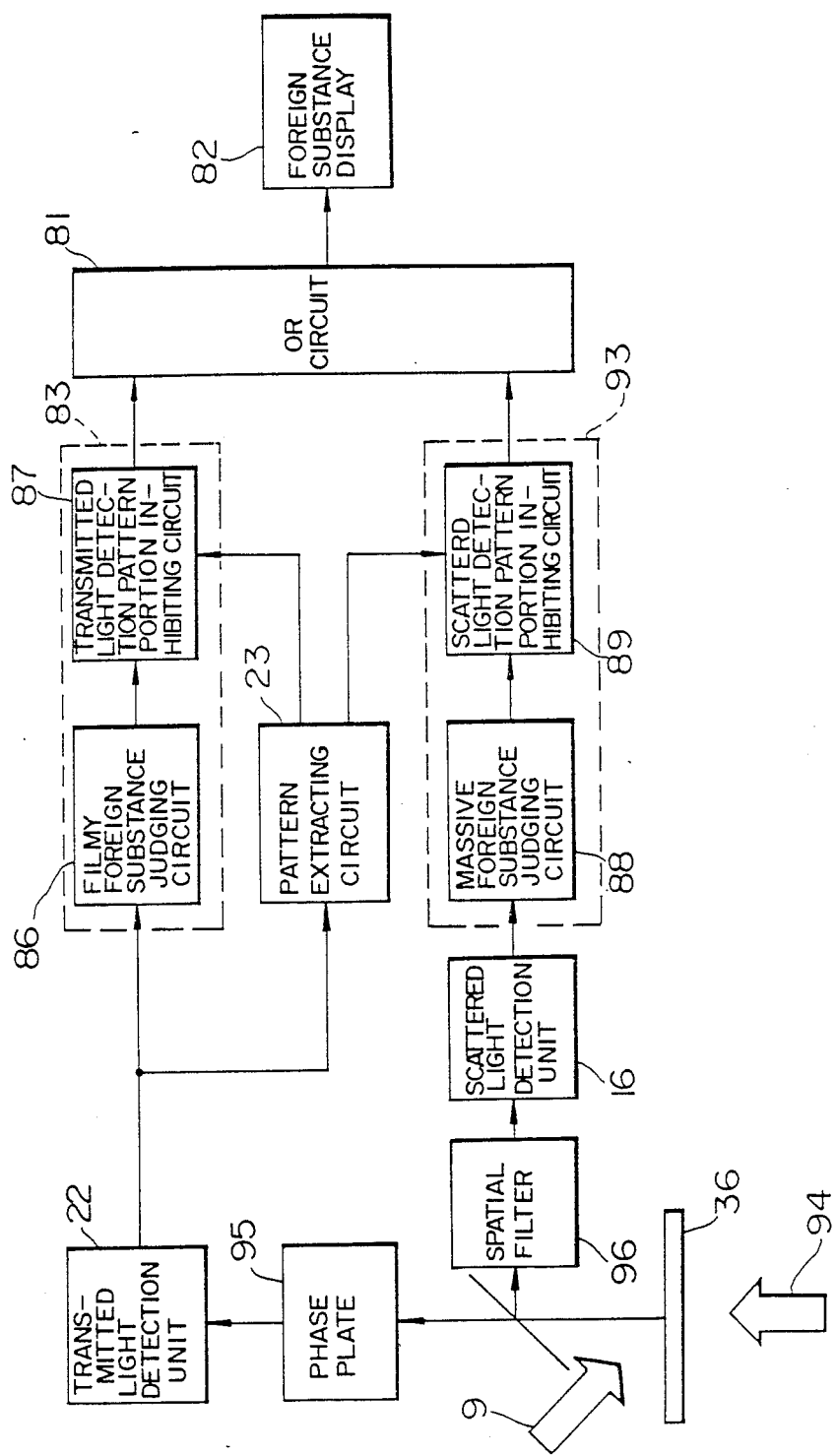
Figure 34:
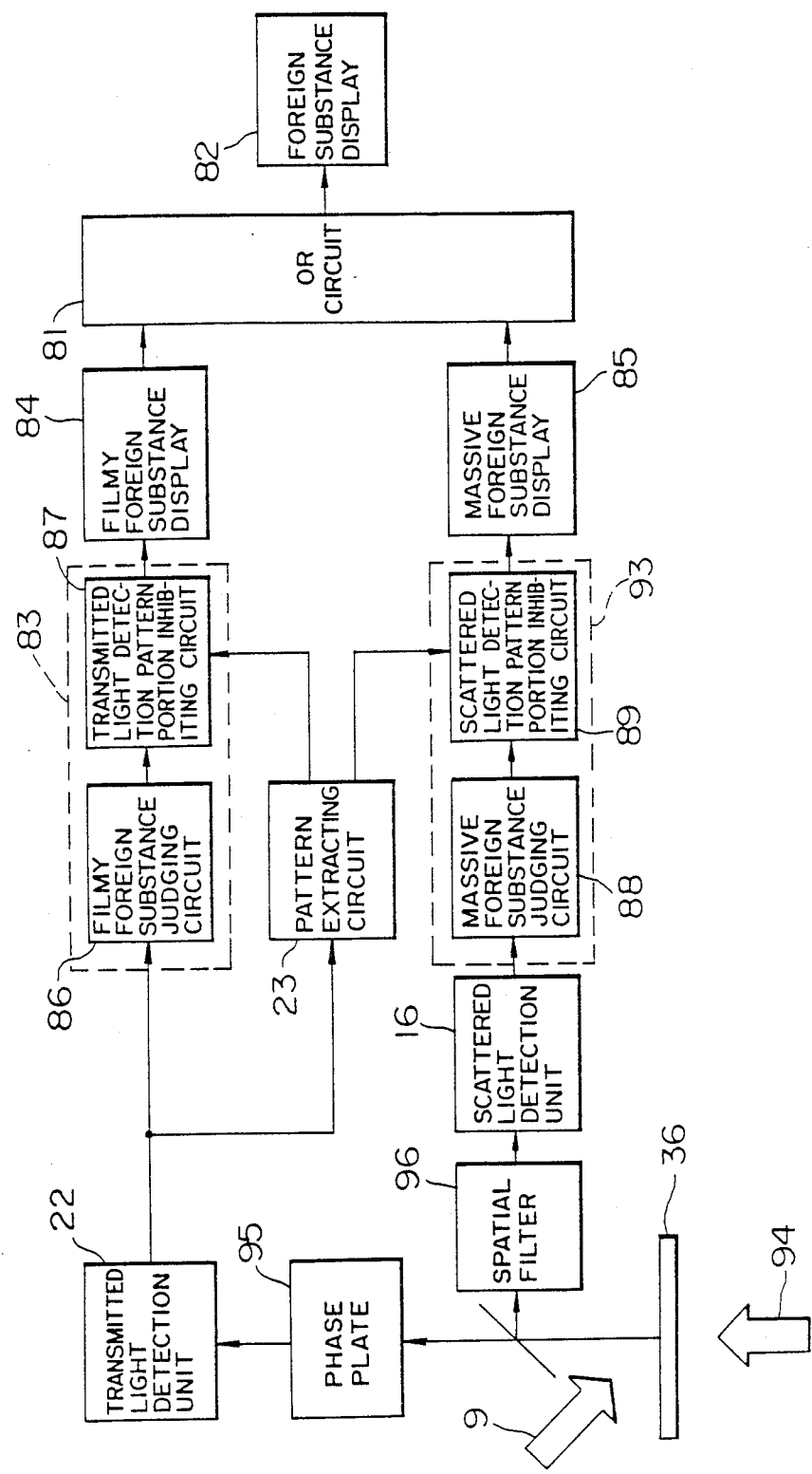
Figure 35:
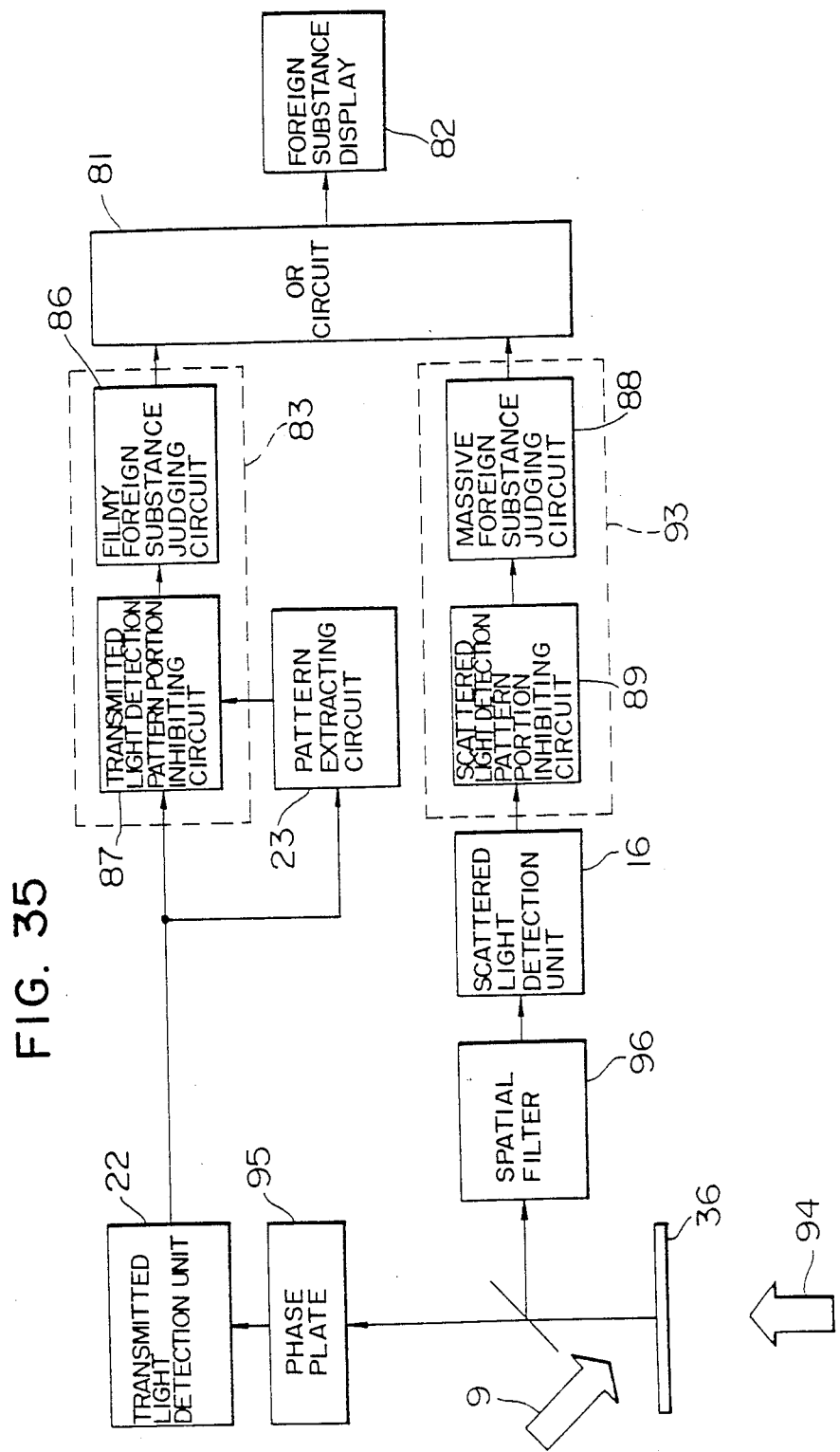
Figure 36:
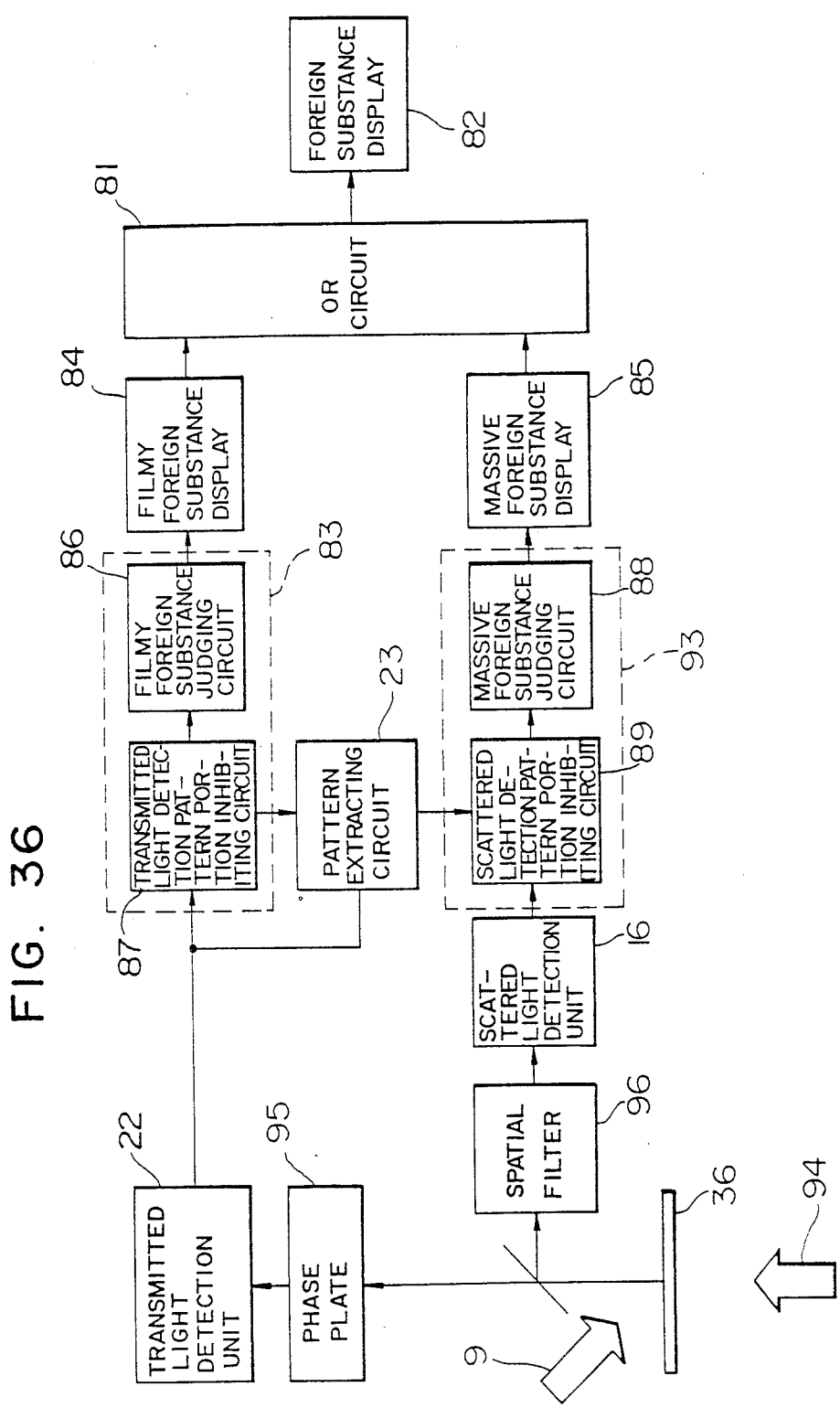
Figure 37:
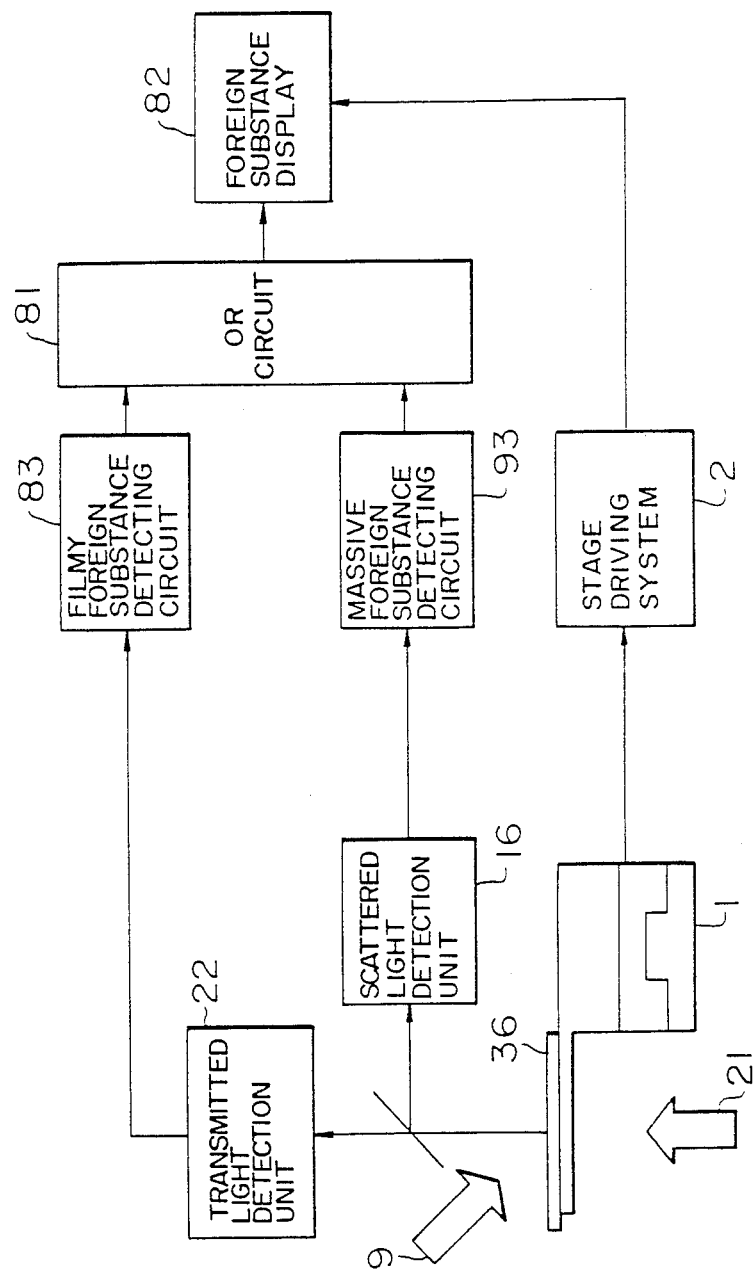
Figure 38:
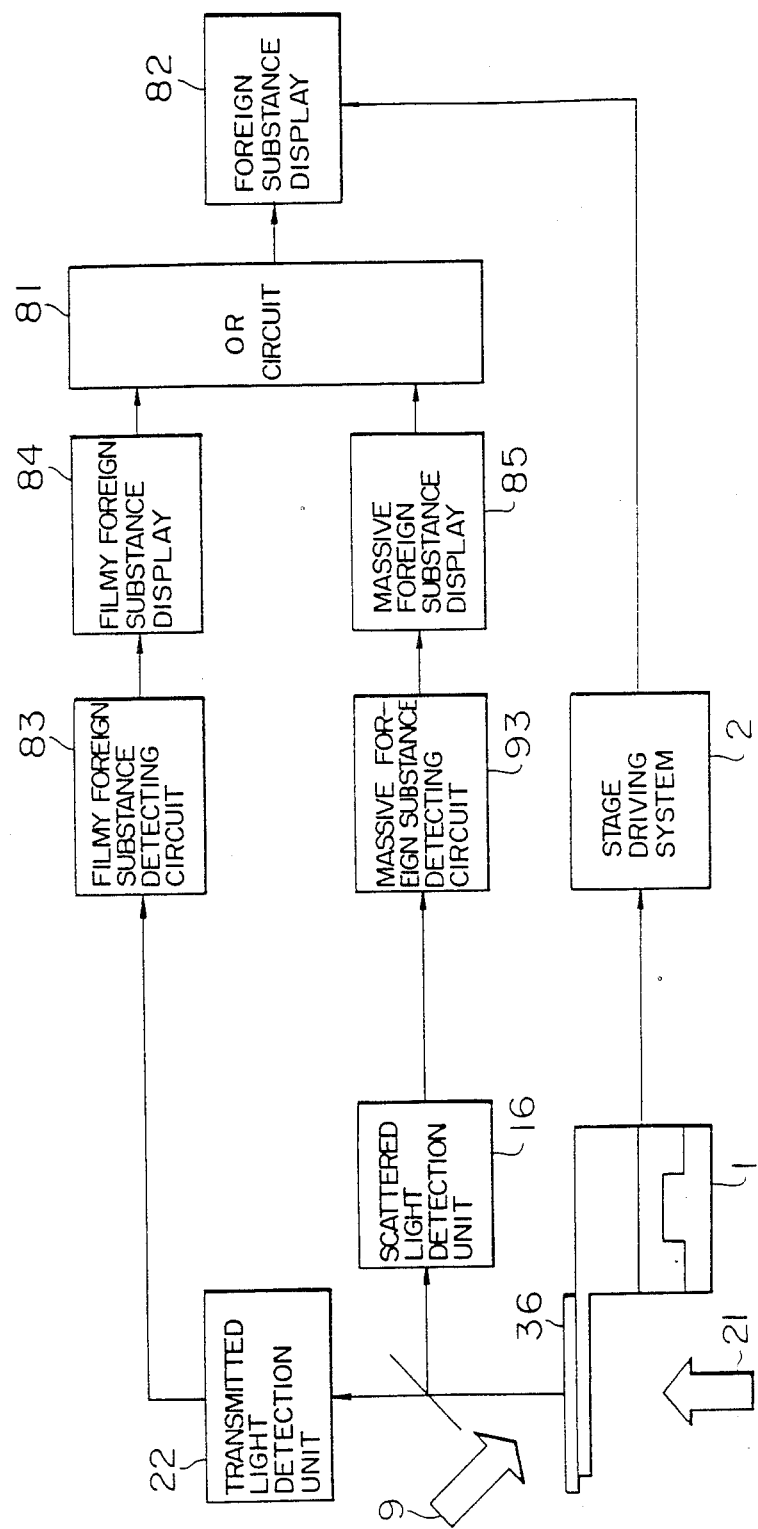
Figure 39:
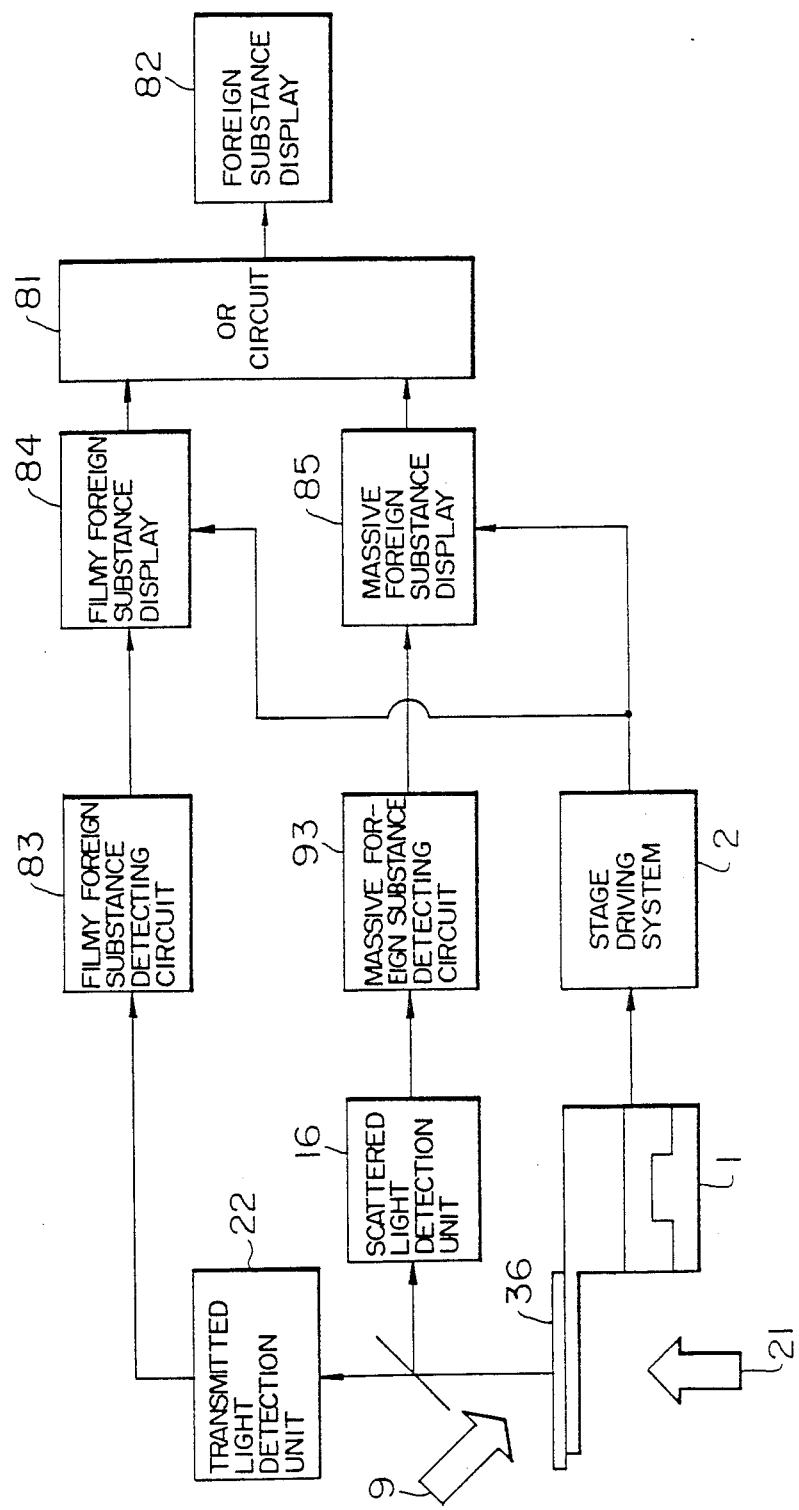
Figure 40:
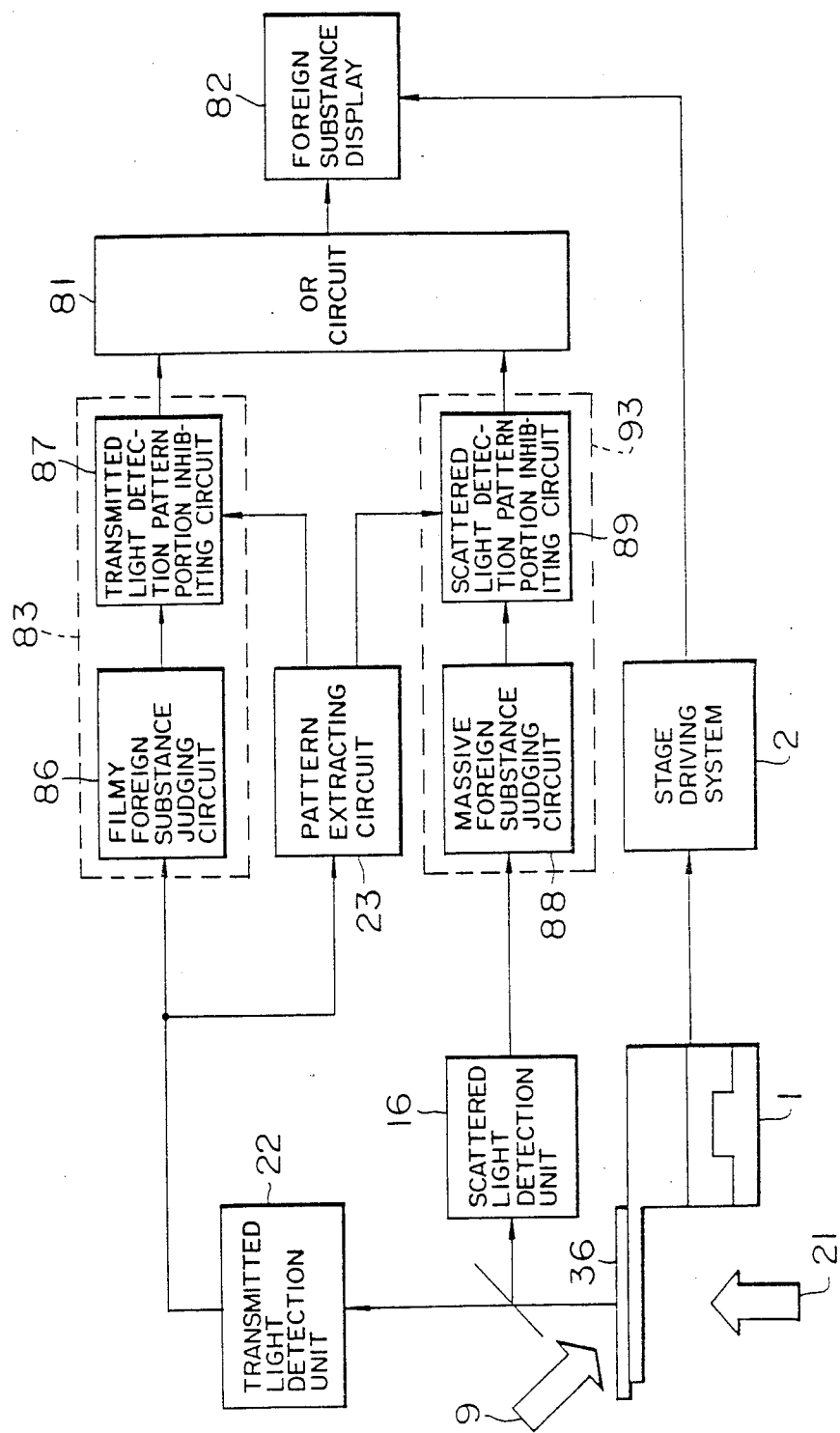
Figure 41:
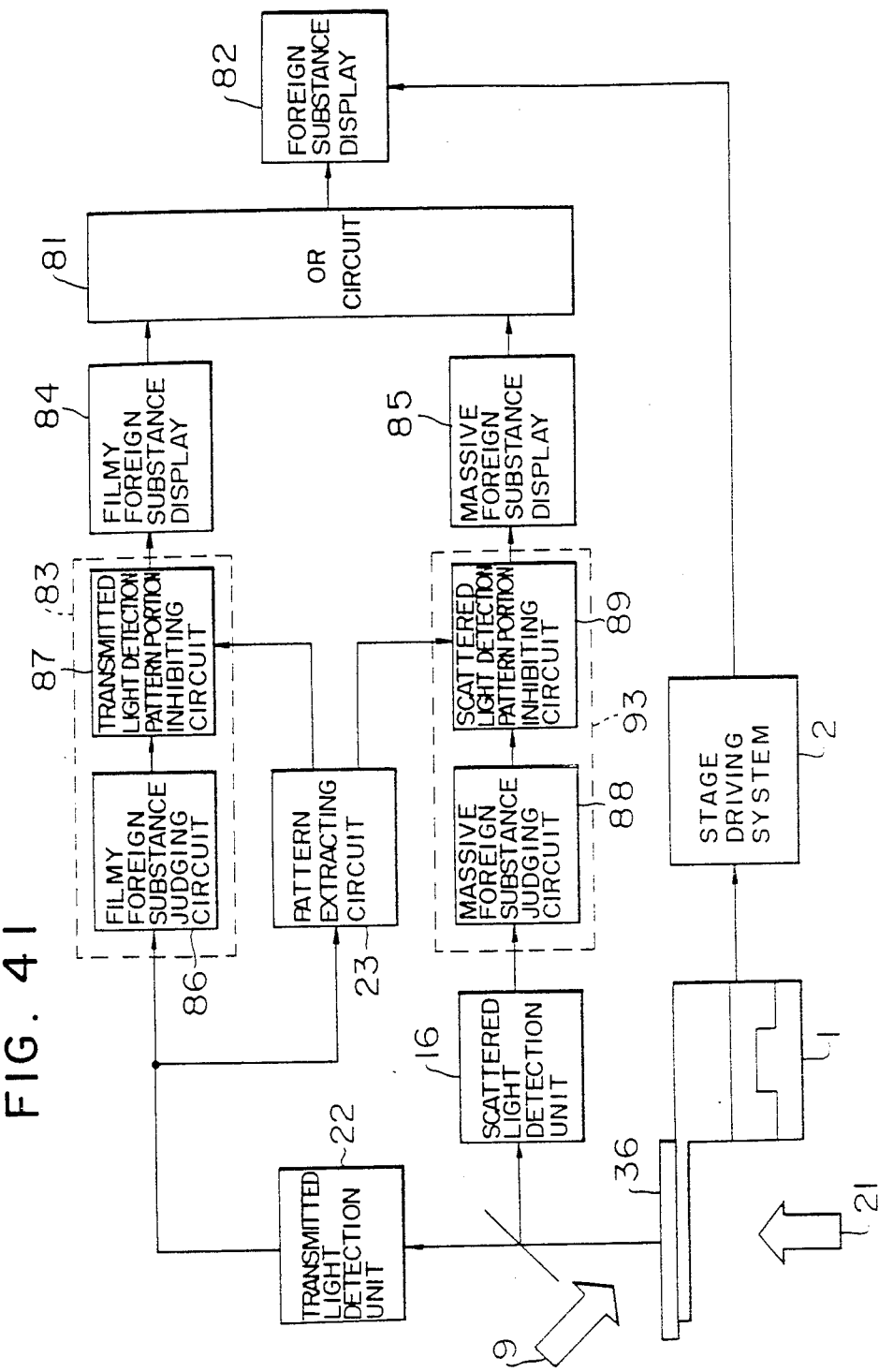
Figure 42:
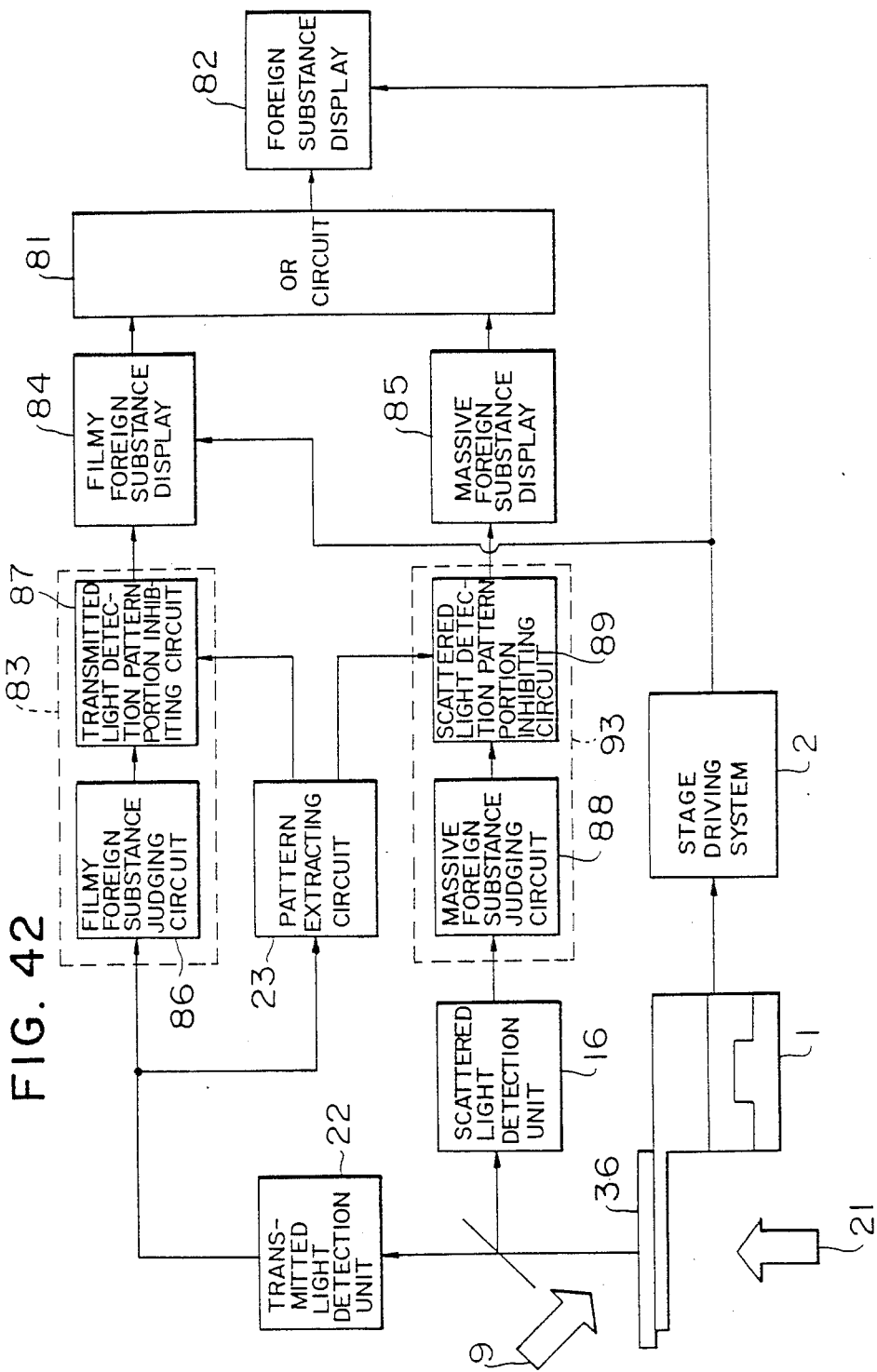
Figure 43:
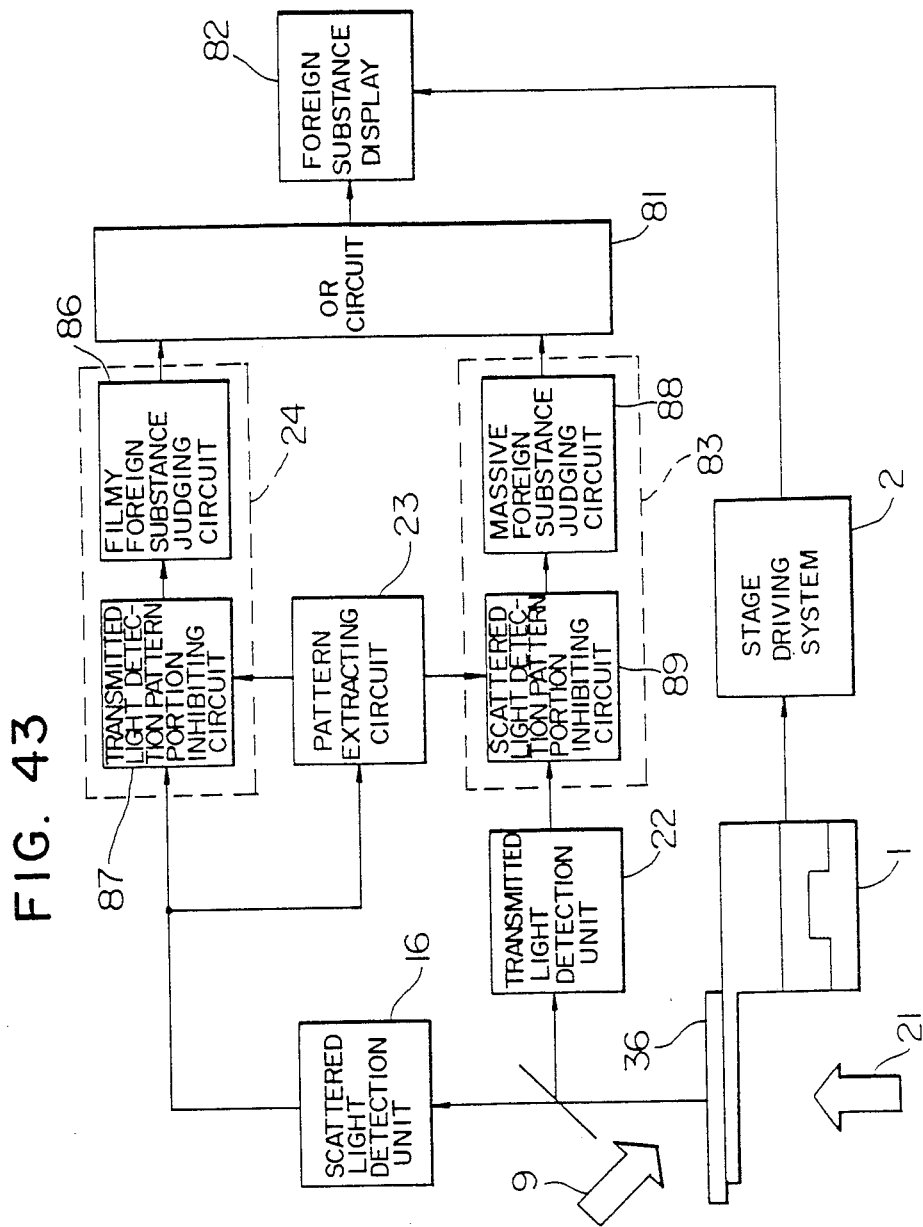
Figure 44:
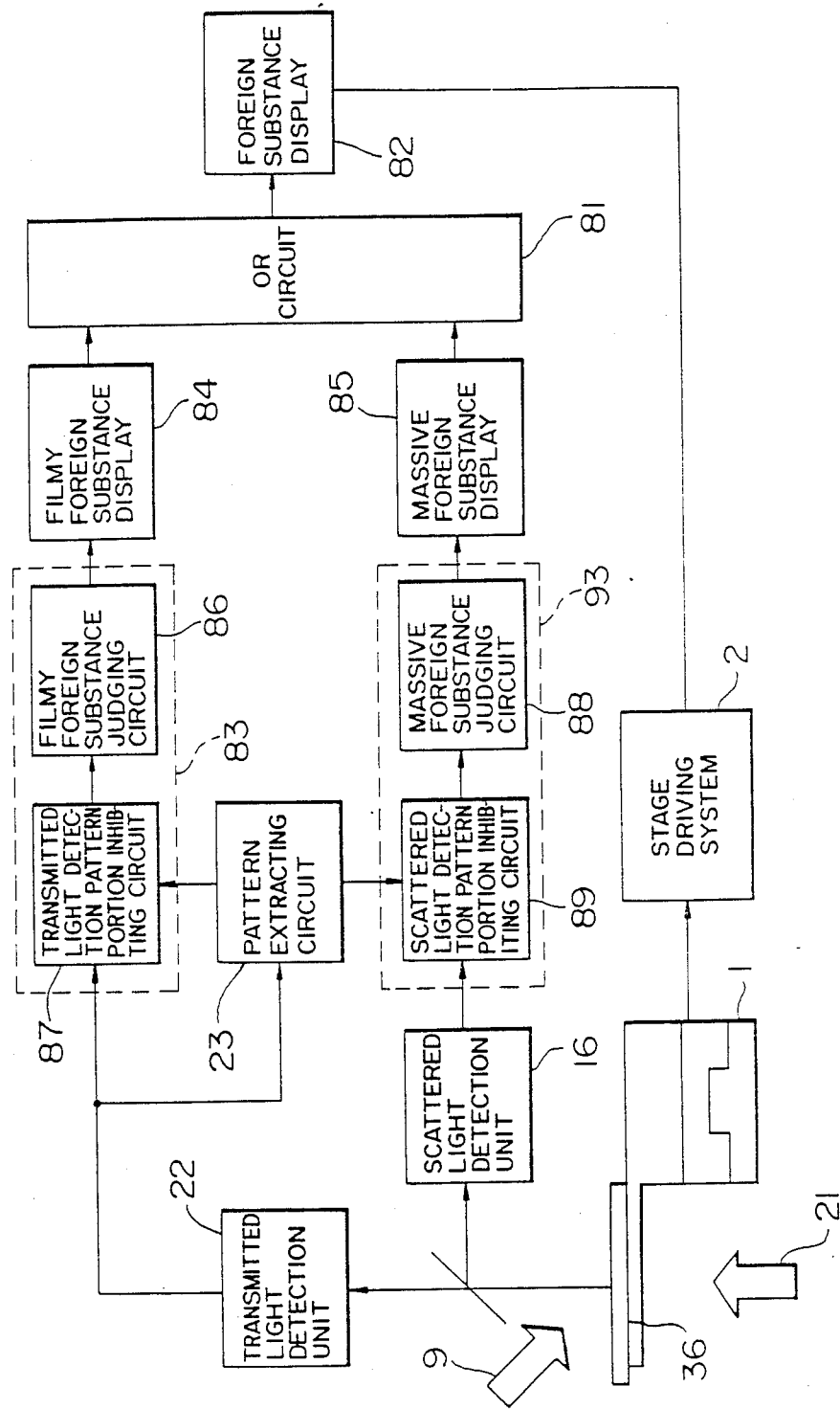
Figure 45:
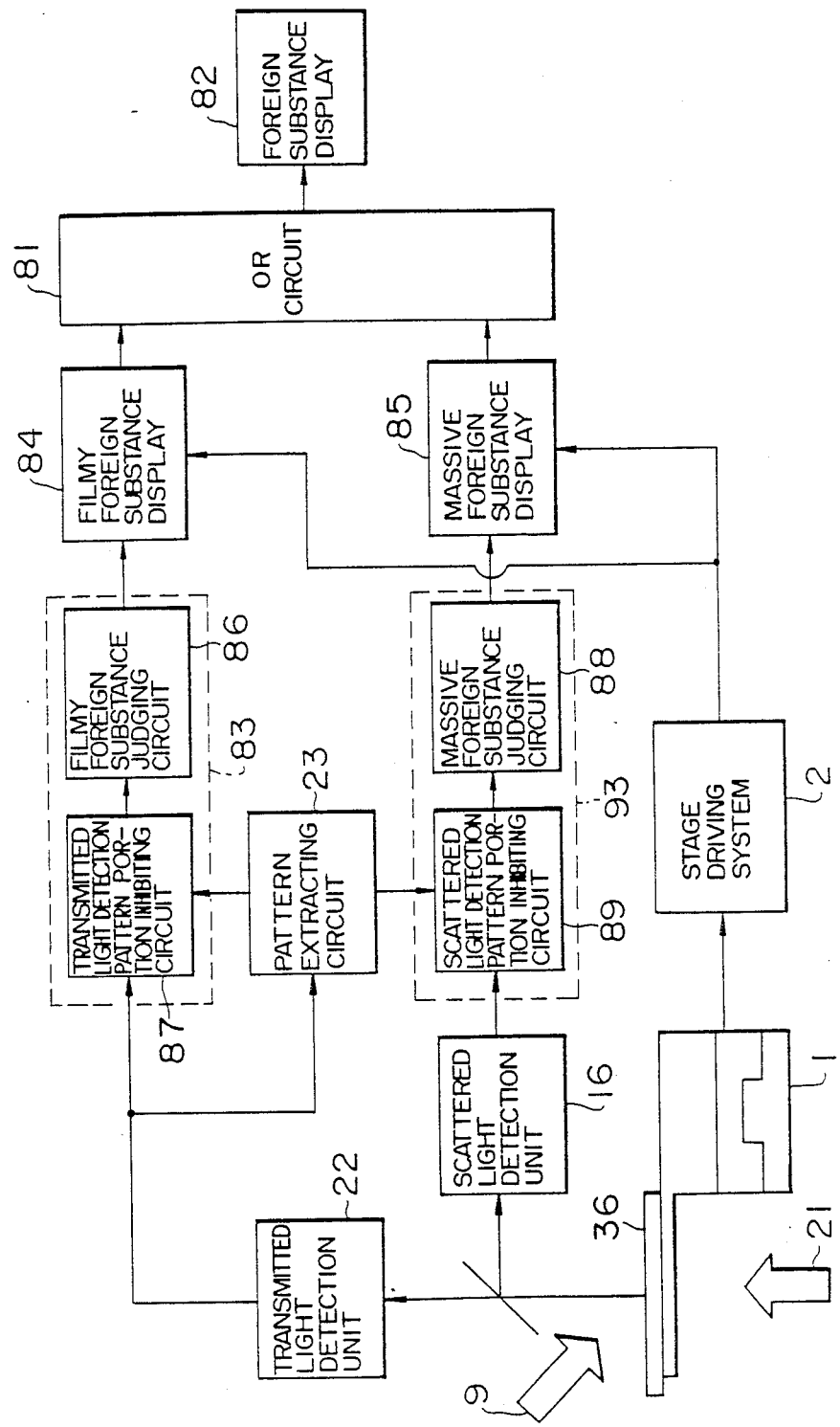
Figure 46:
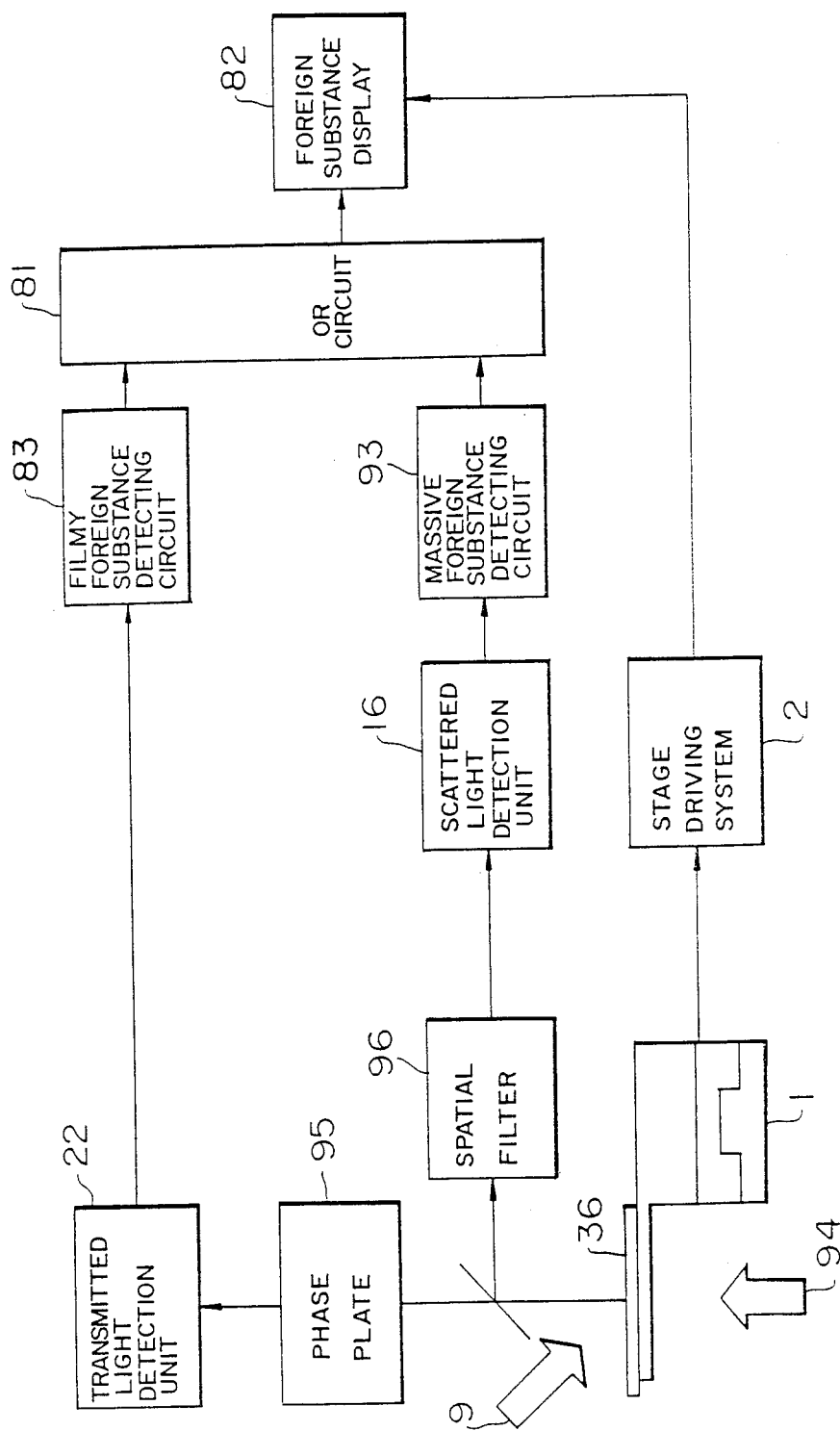
Figure 47:
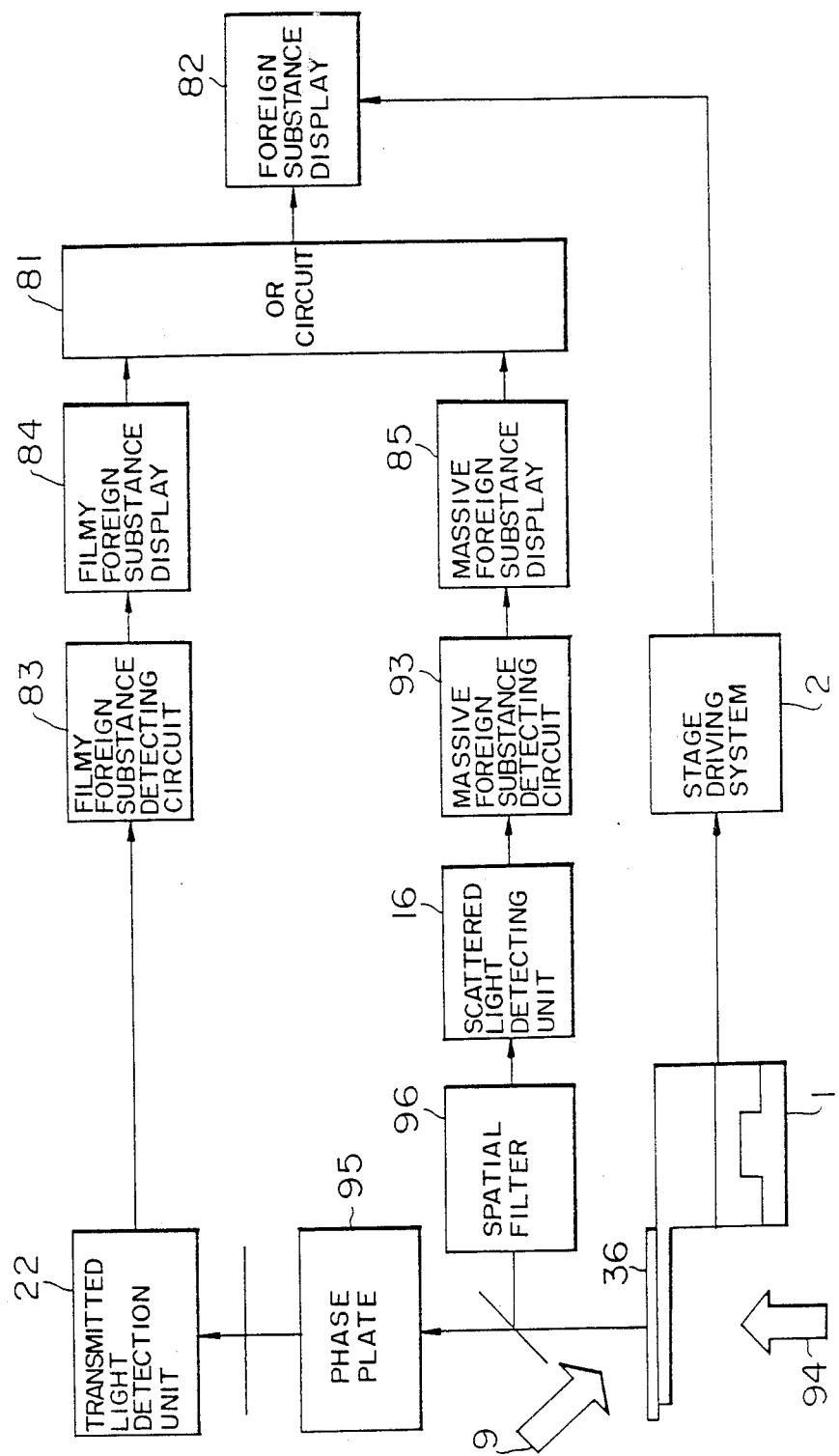
Figure 48:
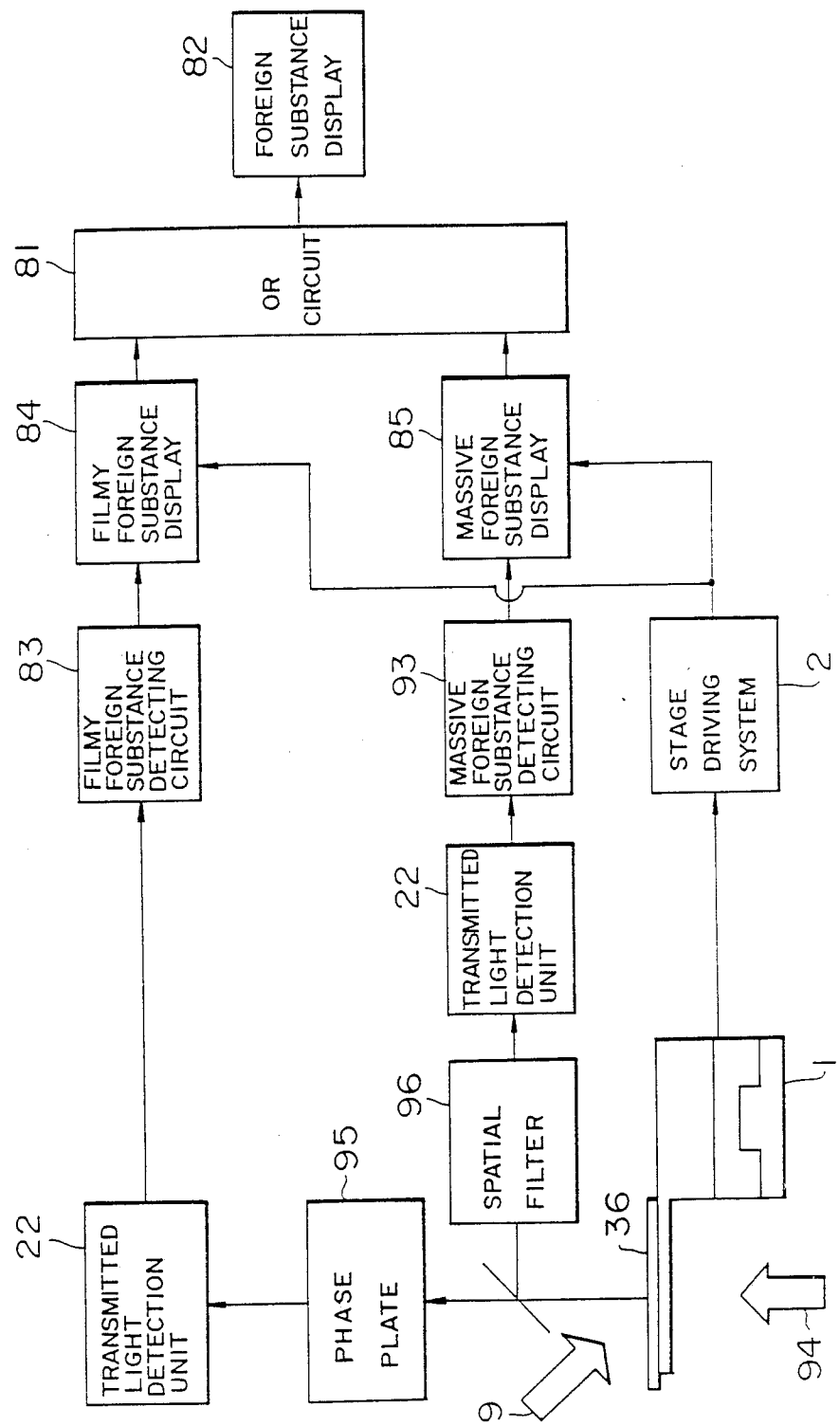
Figure 49:
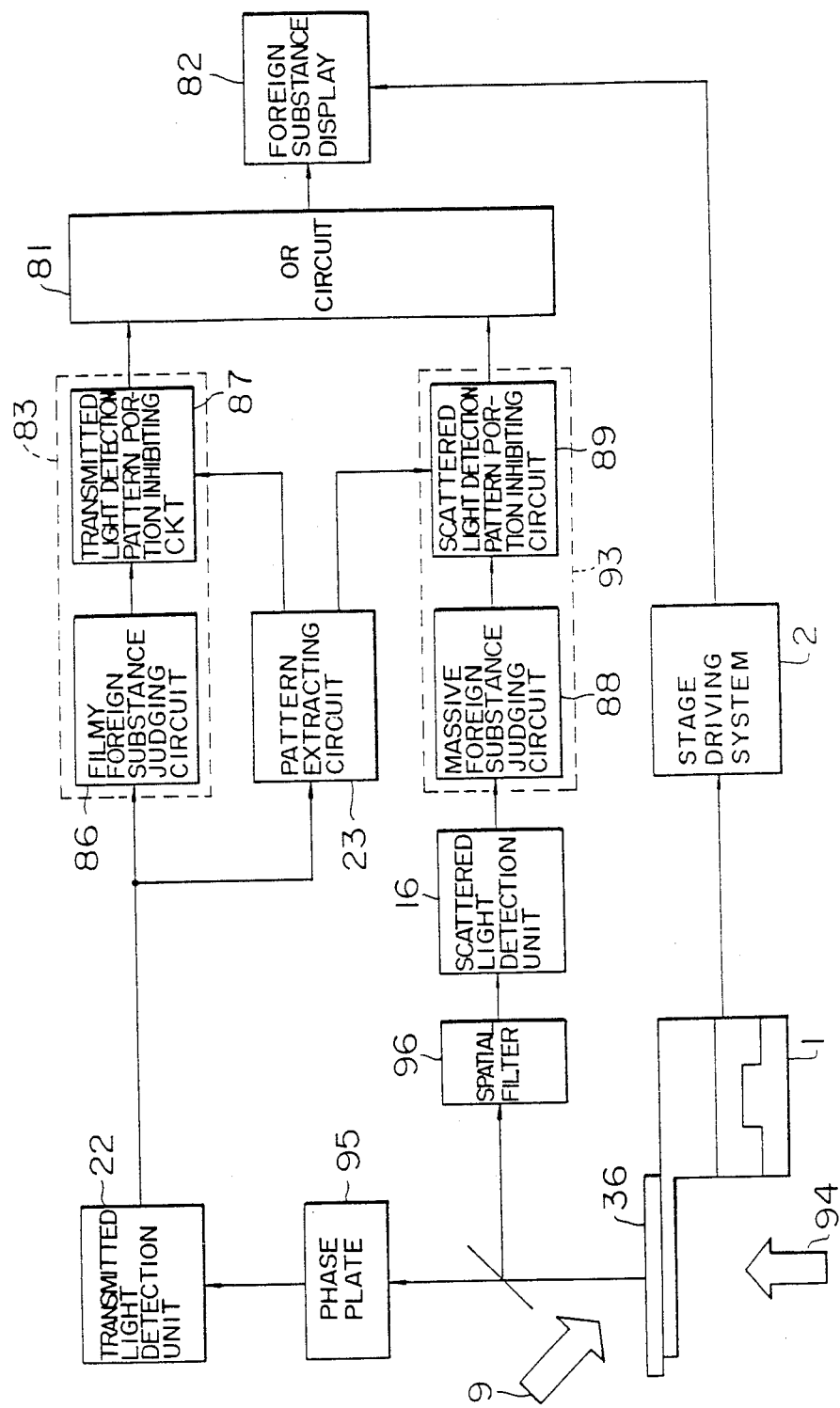
Figure 50:
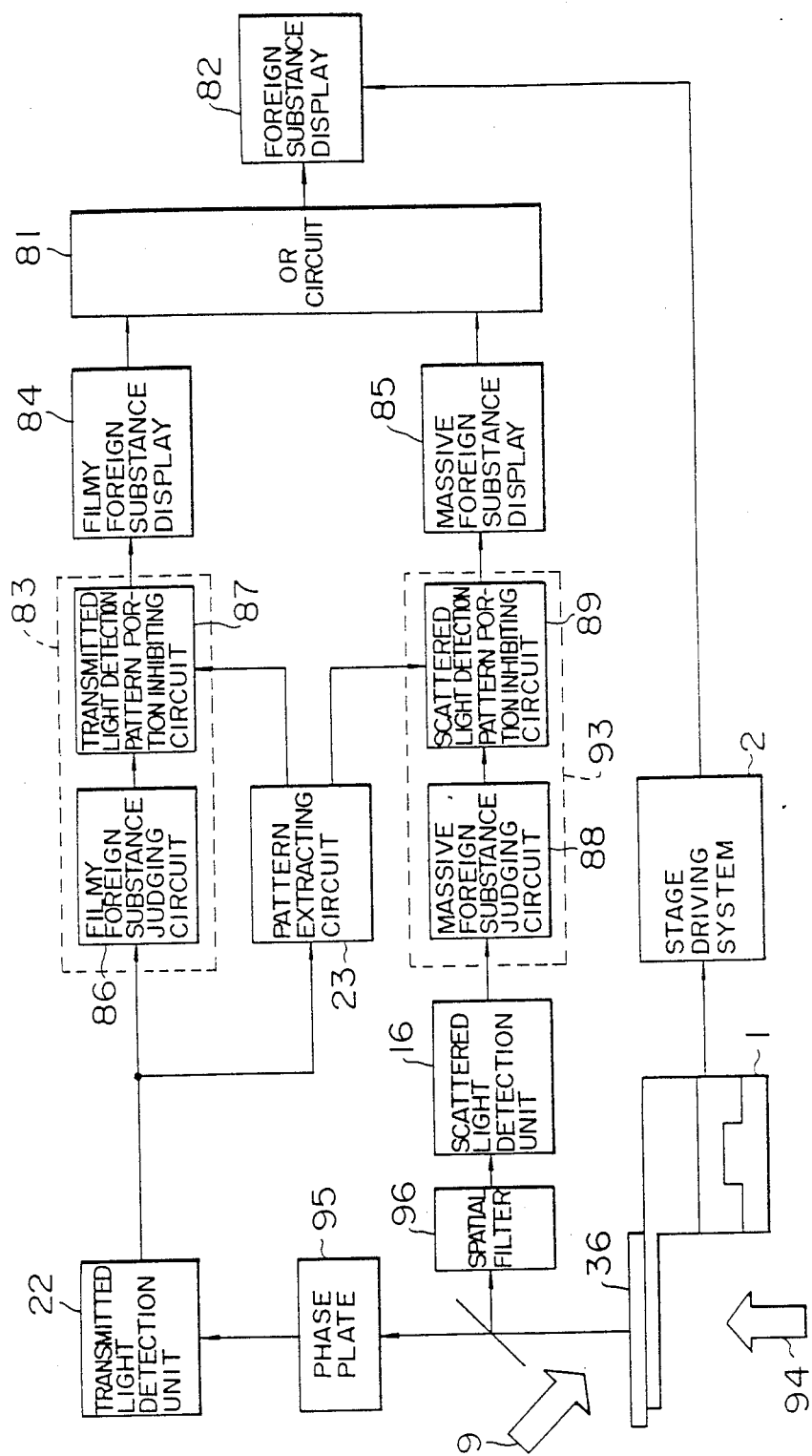
Figure 51:
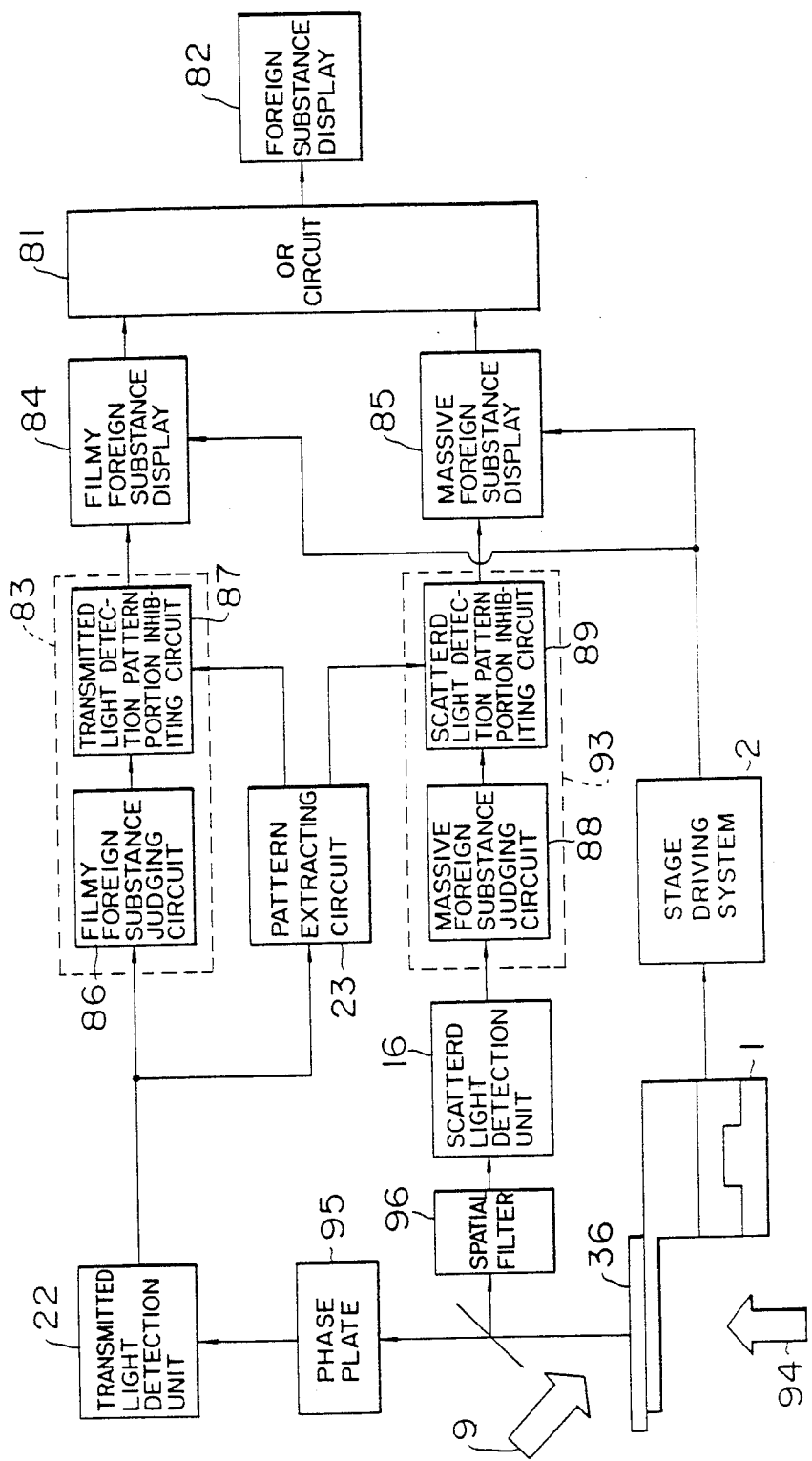
Figure 52:
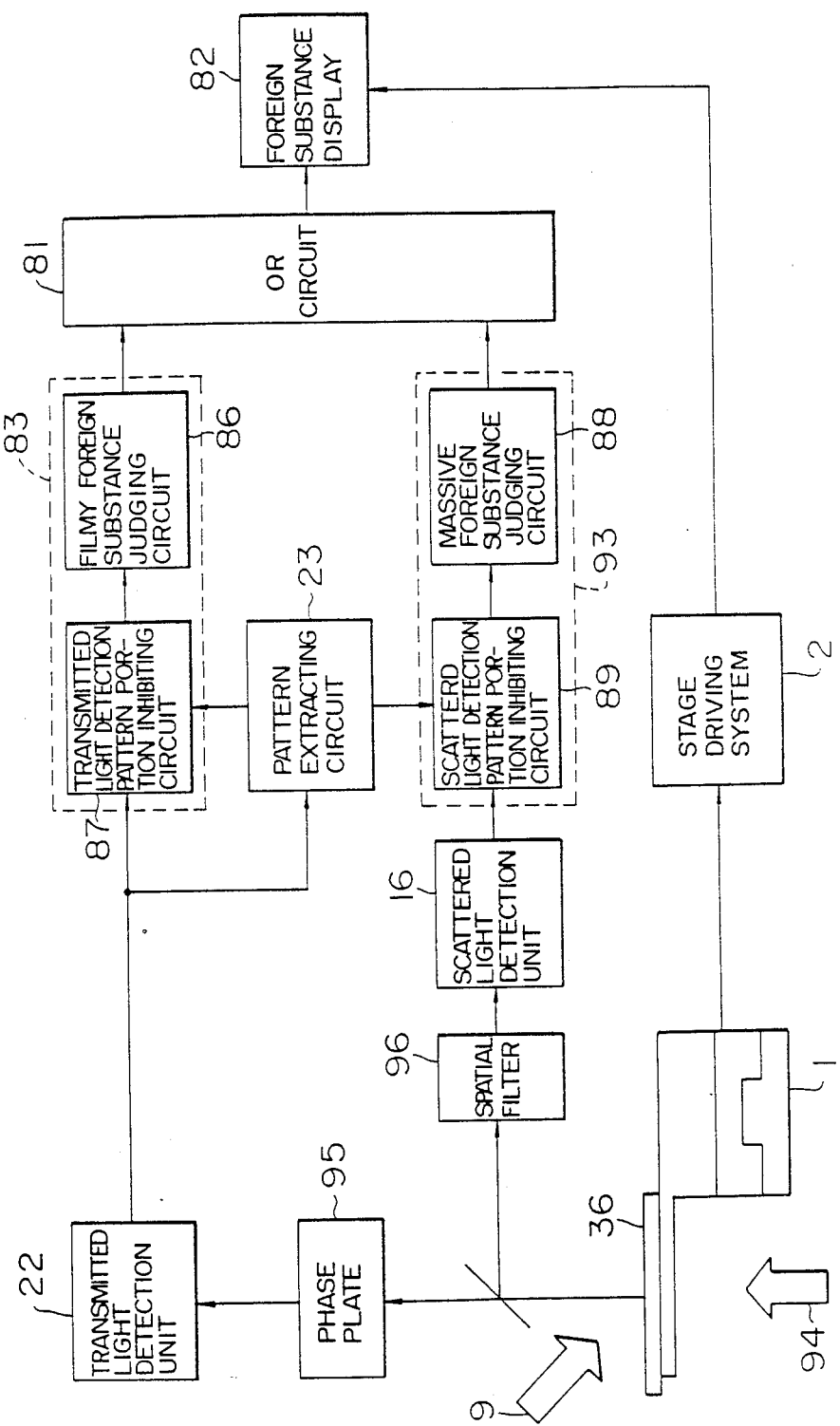
Figure 53:
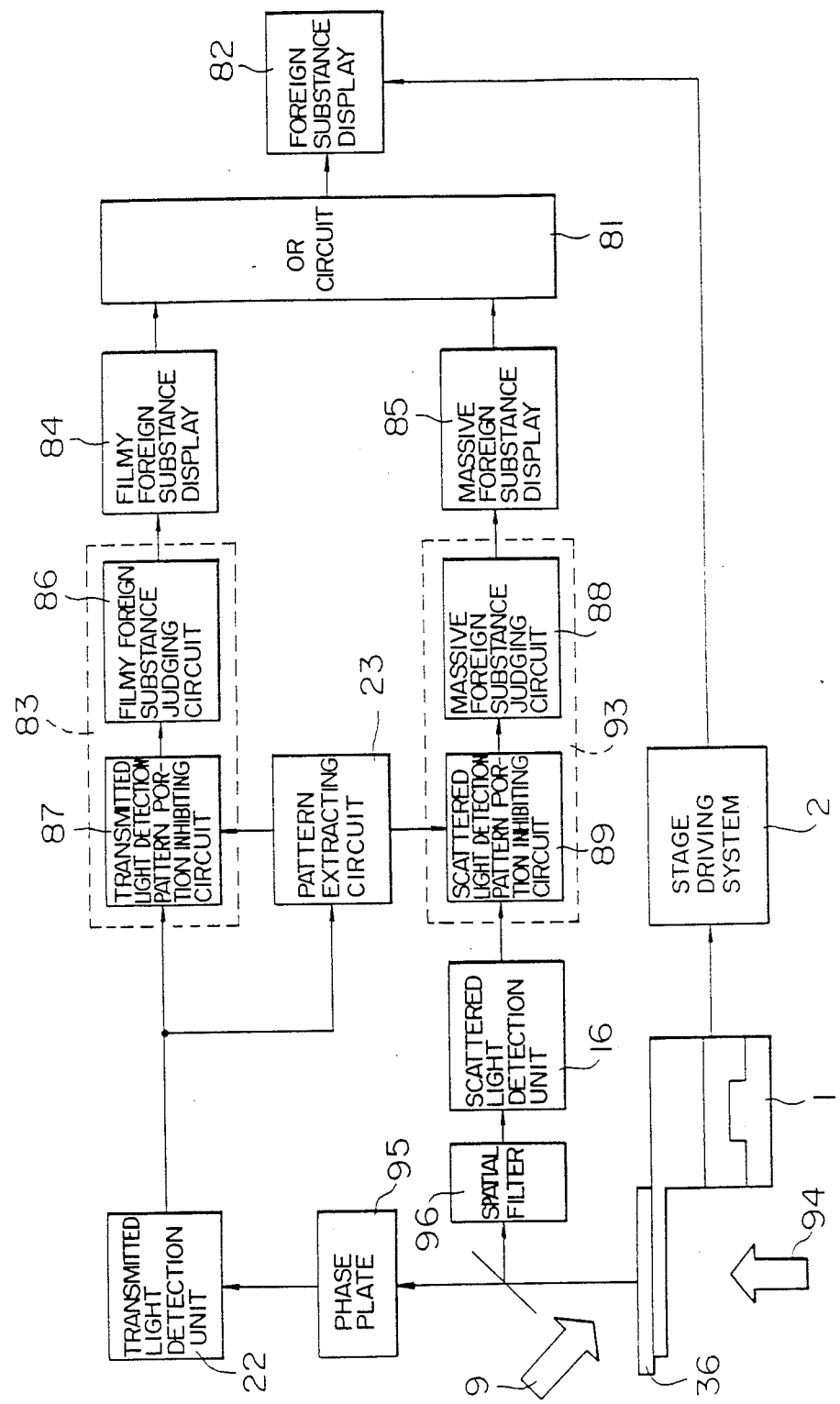
Figure 54:
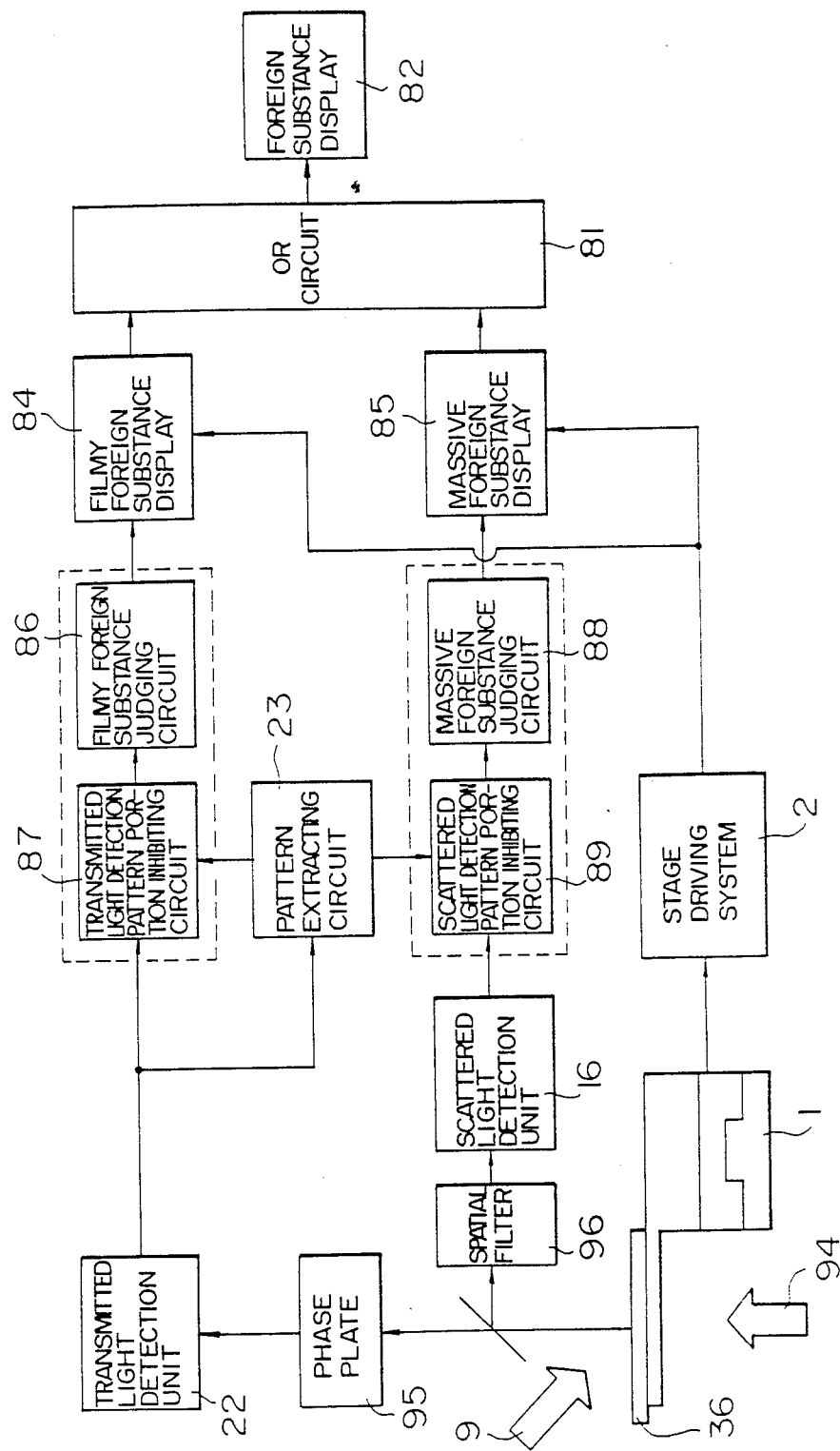
Figure 55:
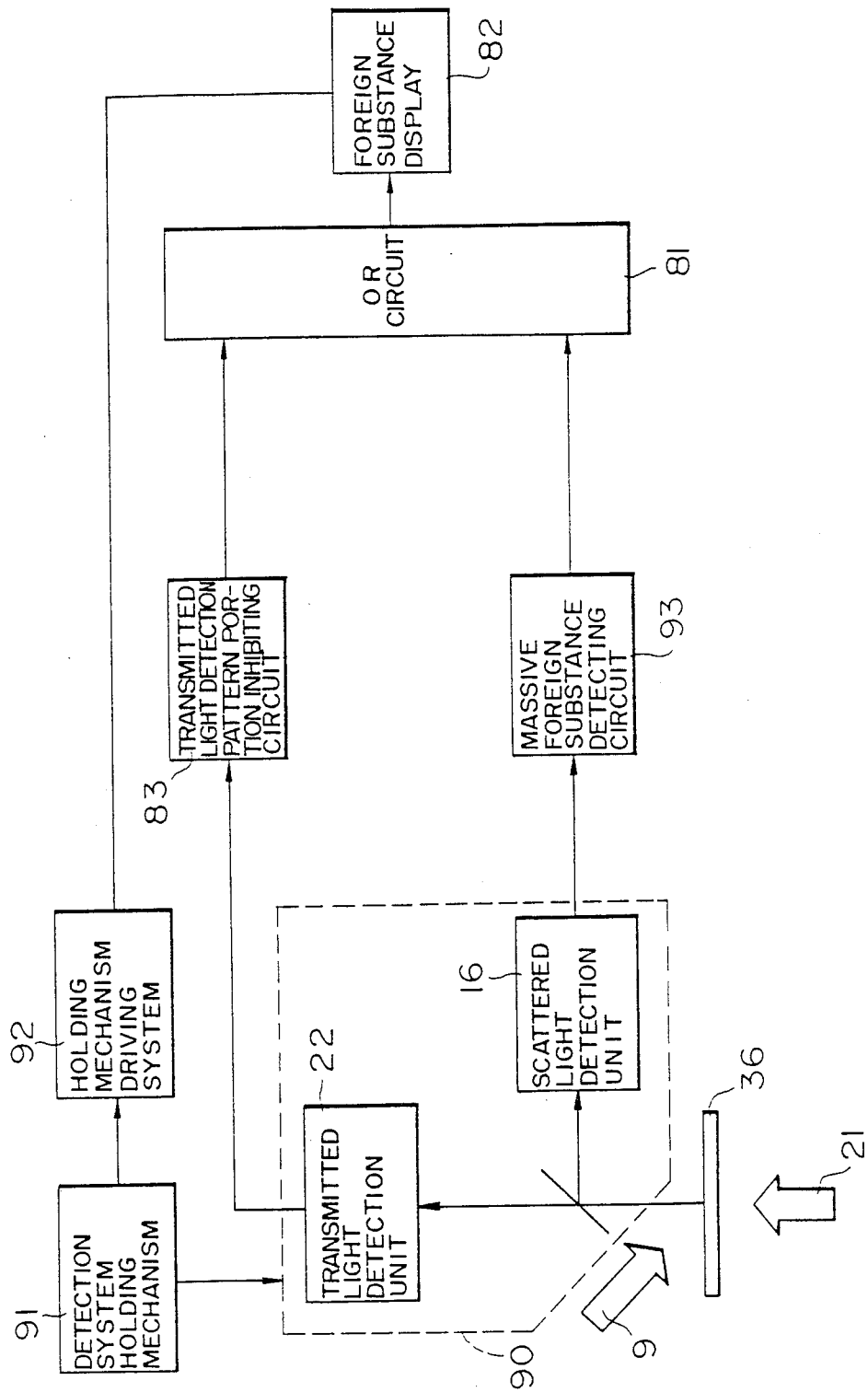
Figure 56:
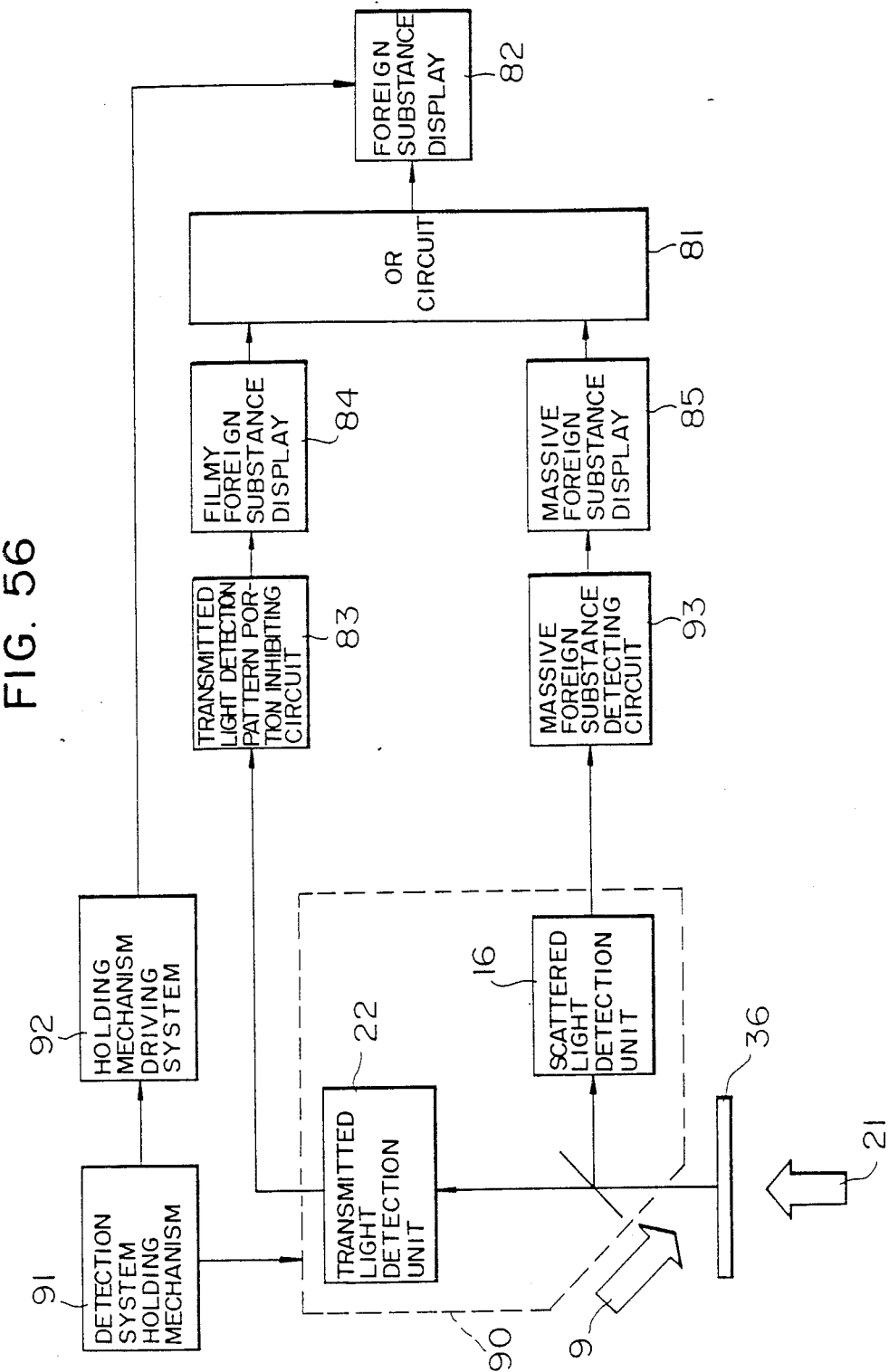
Figure 57:
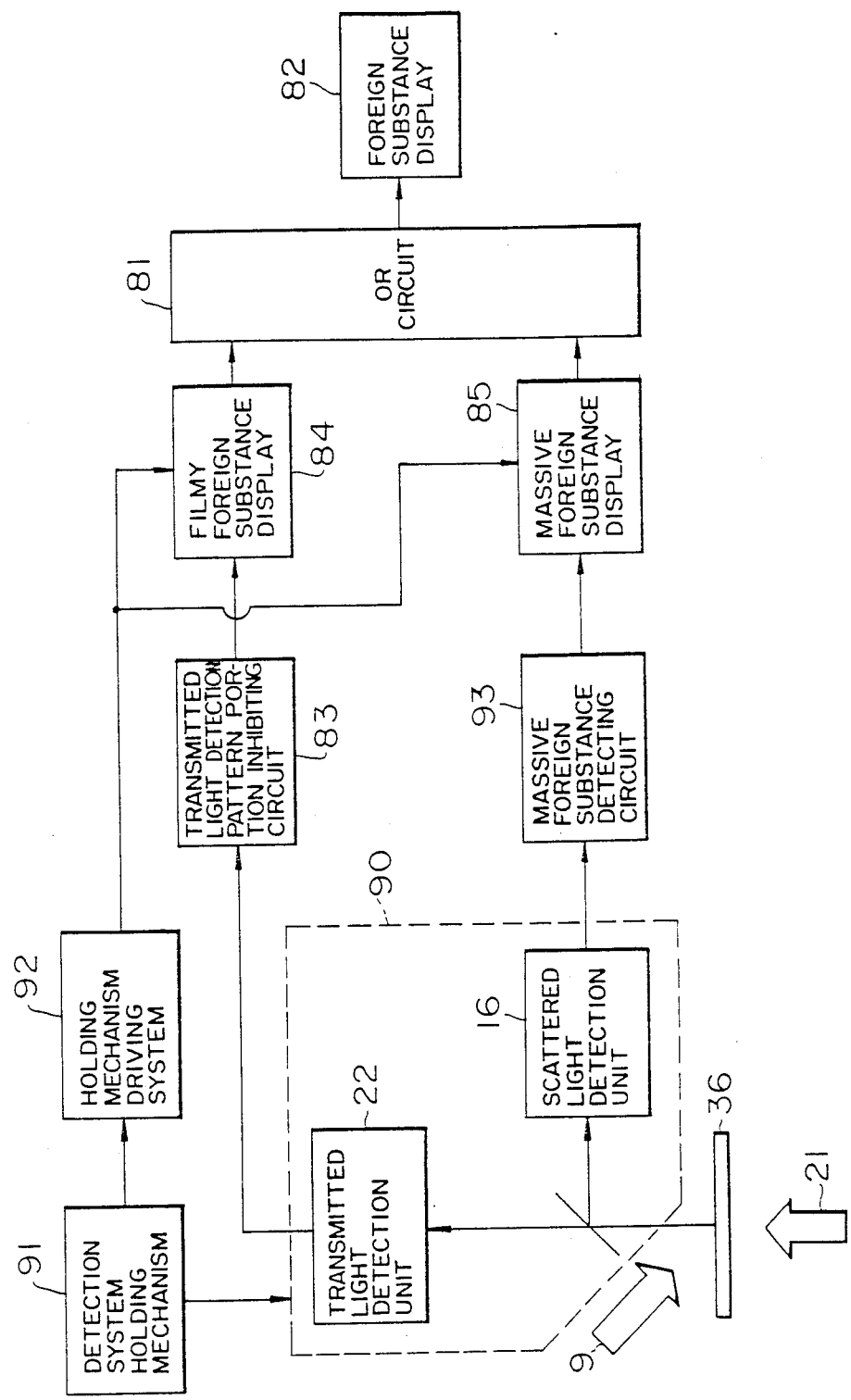
Figure 58:
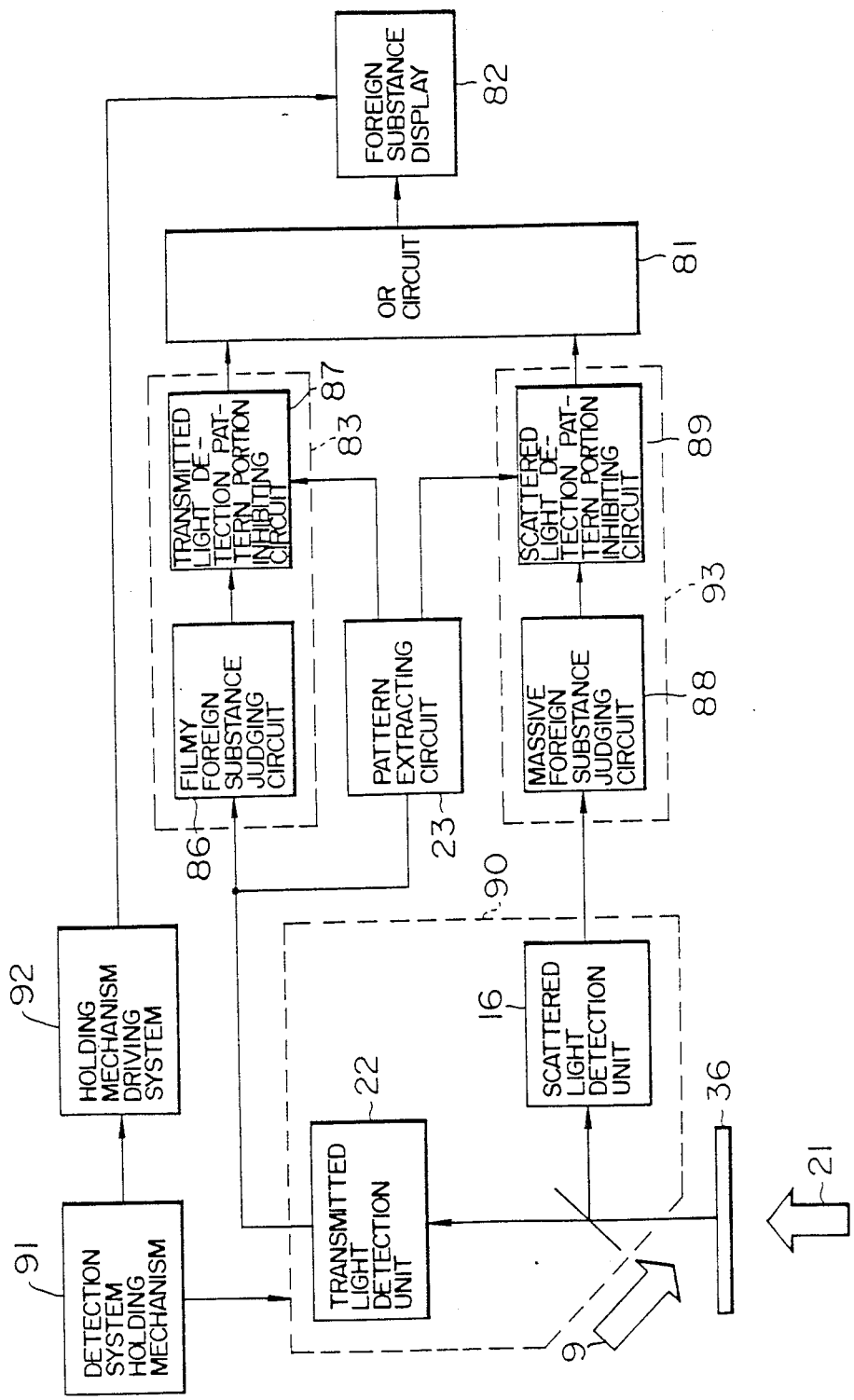
Figure 59:
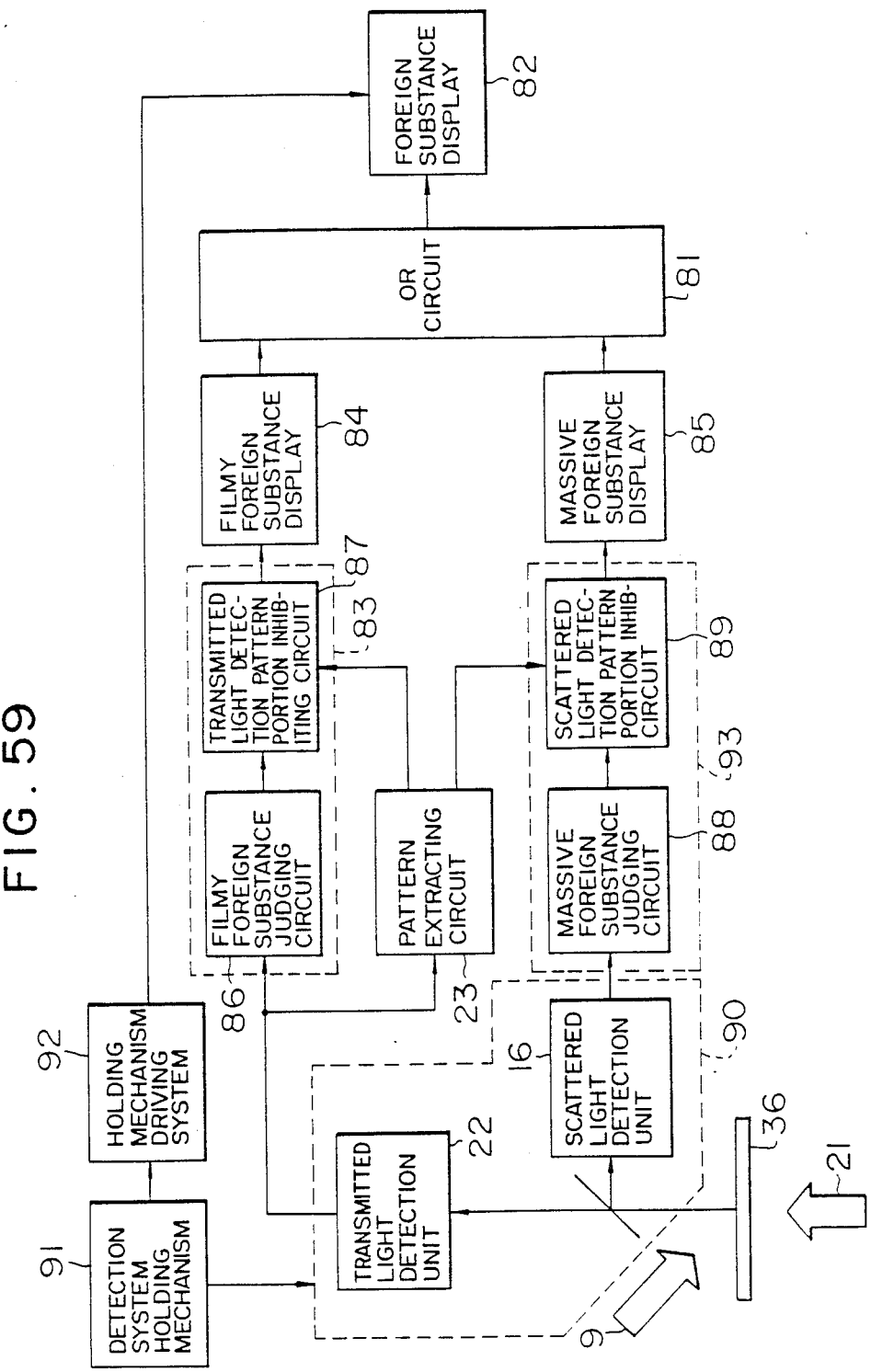
Figure 60:
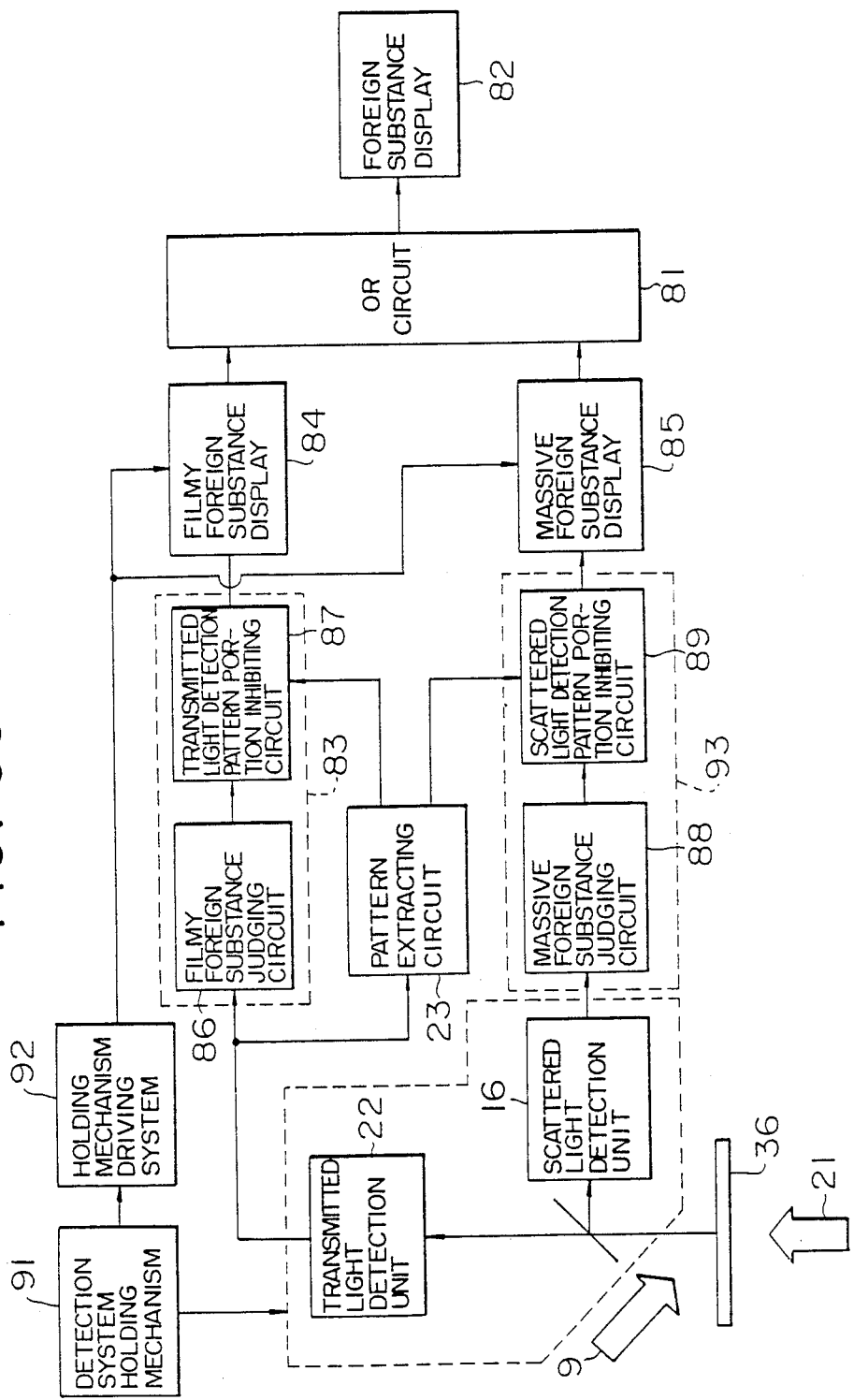
Figure 61:
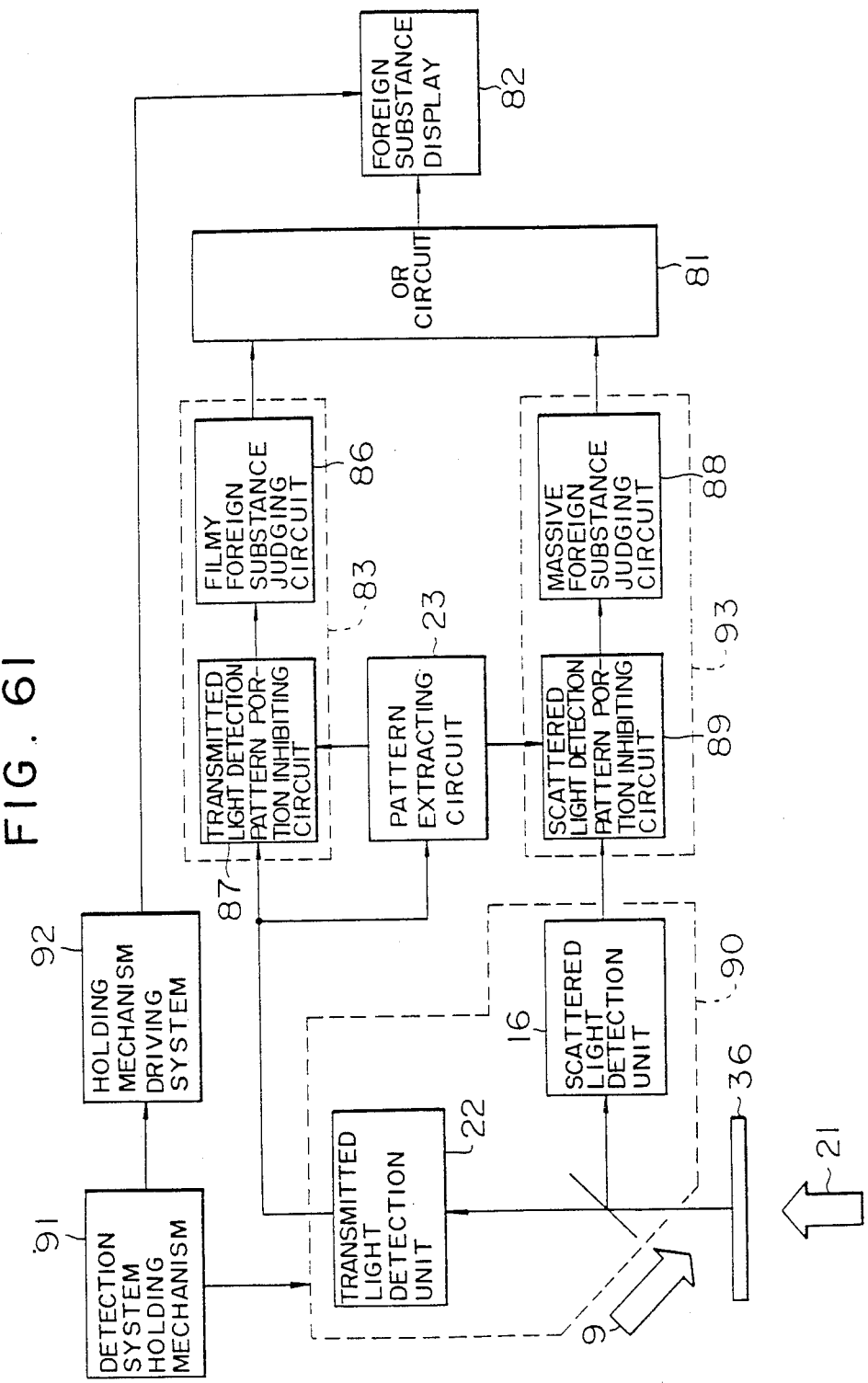
Figure 62:
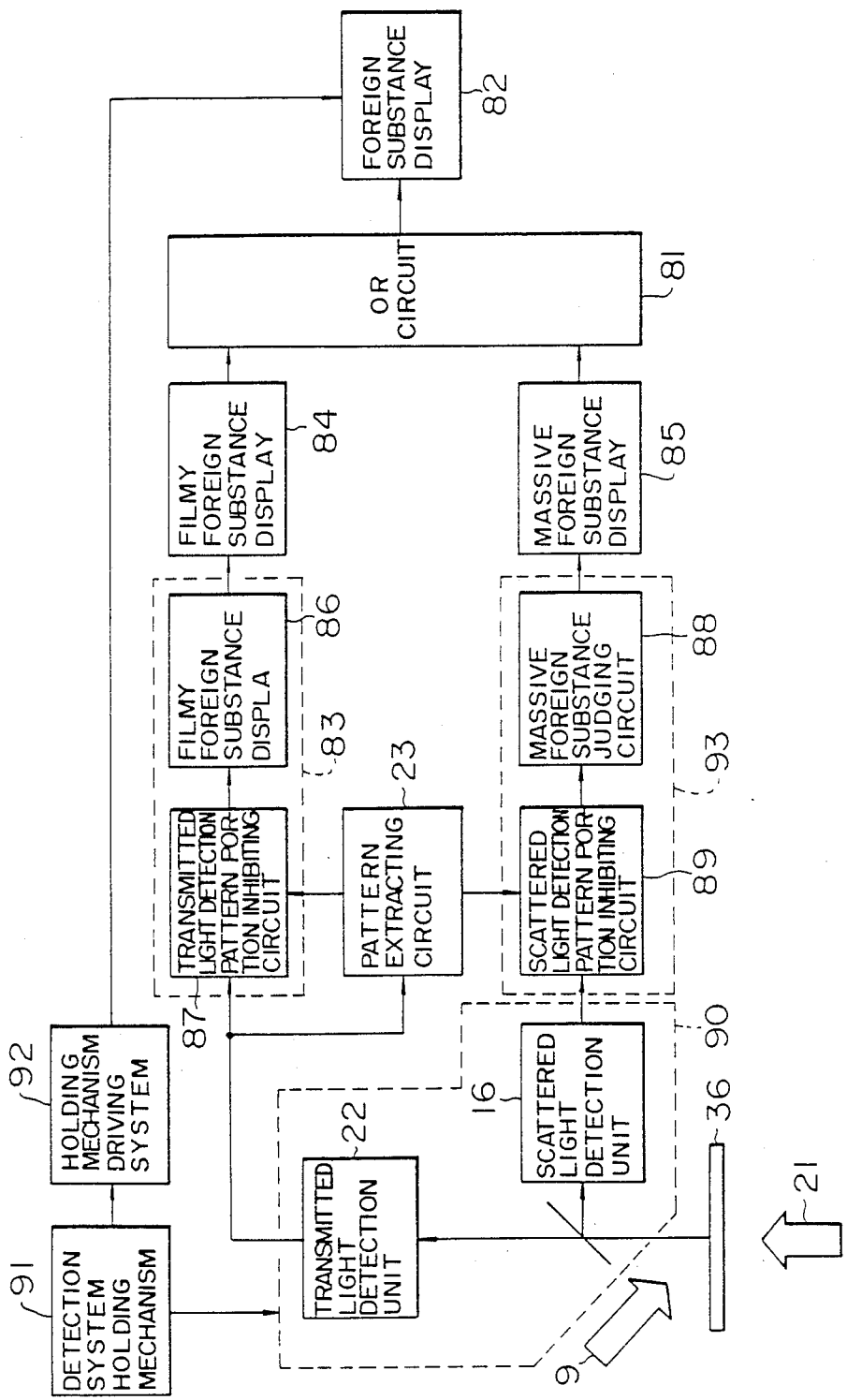
Figure 63:
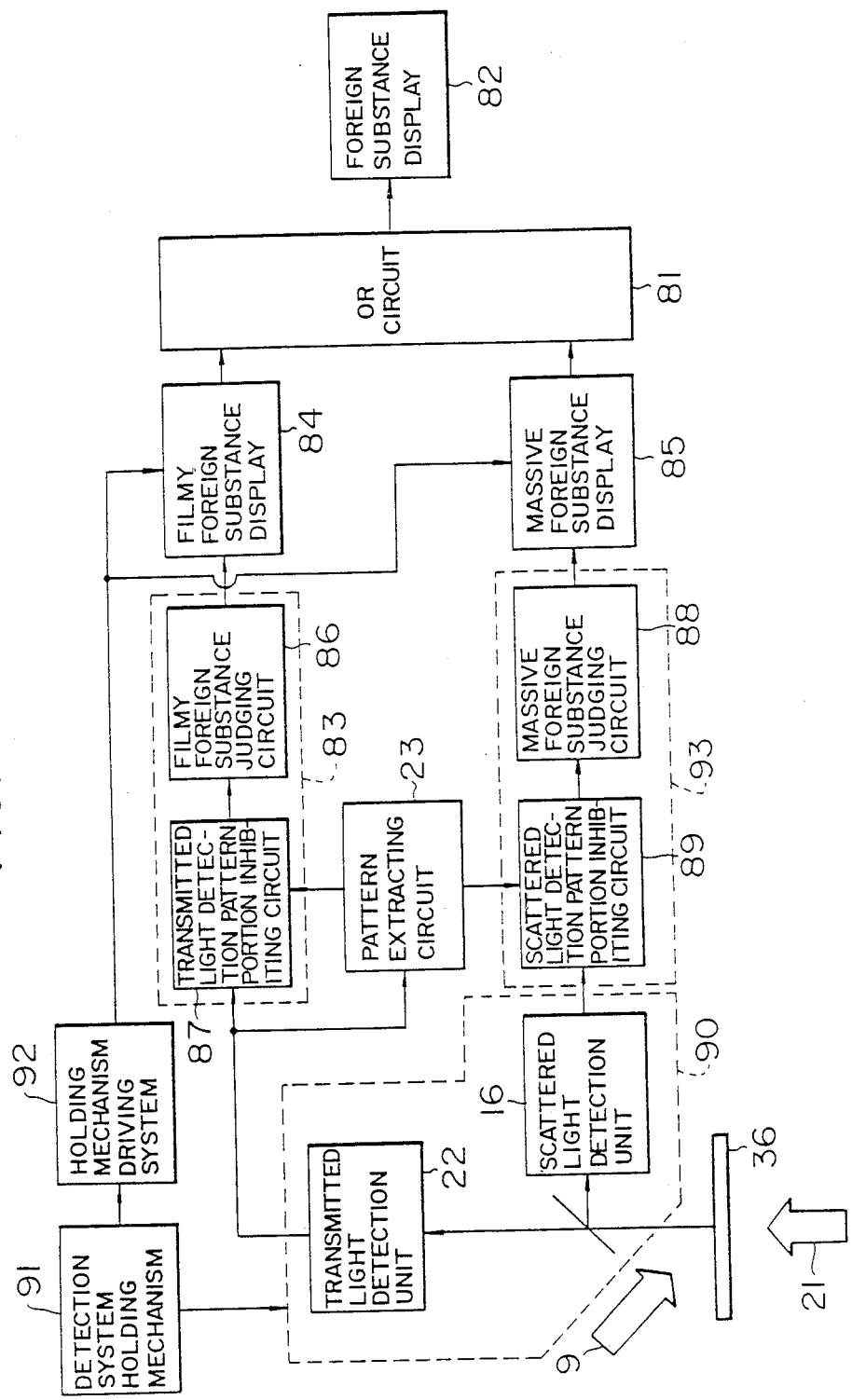
Figure 64:
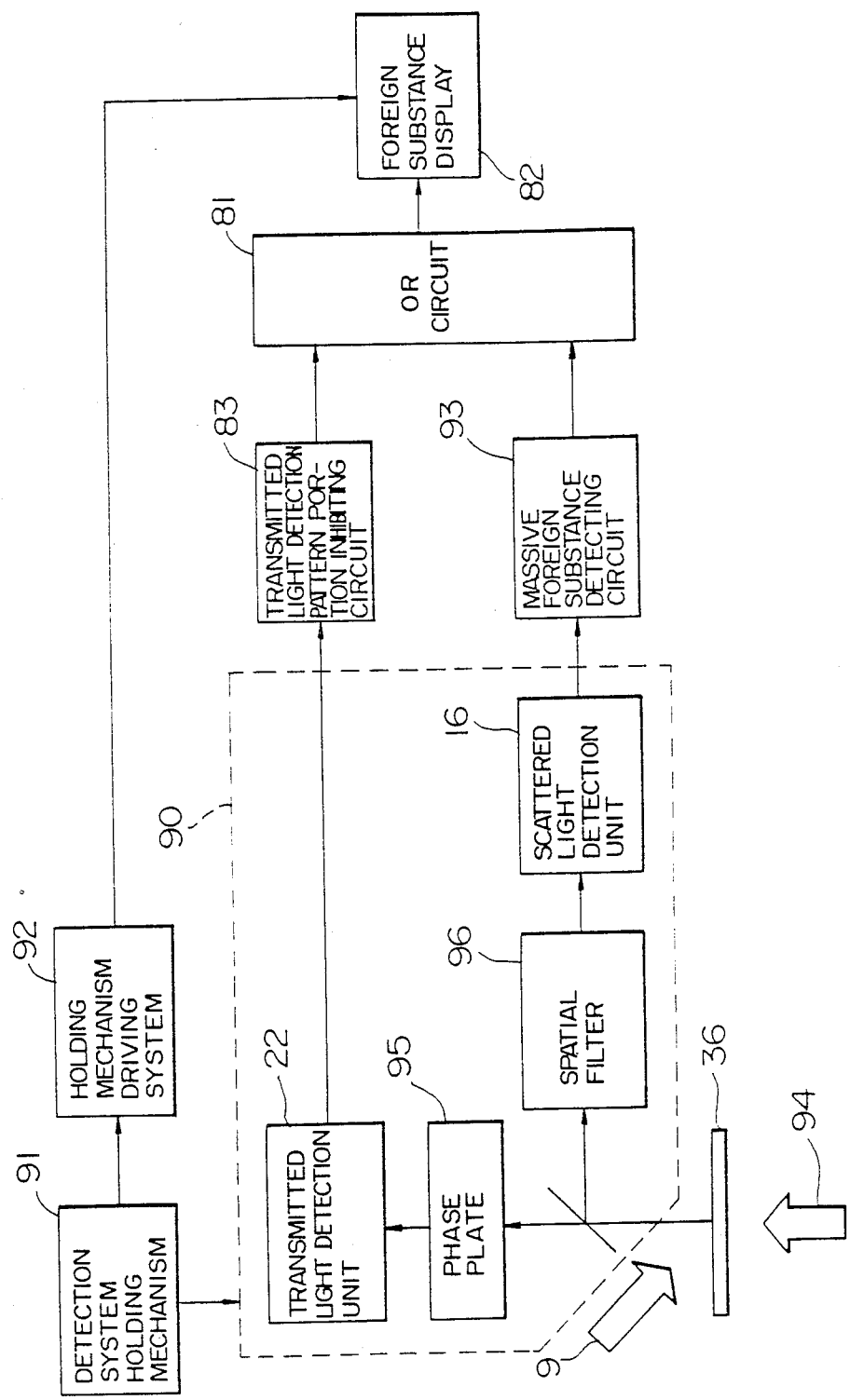
Figure 65:
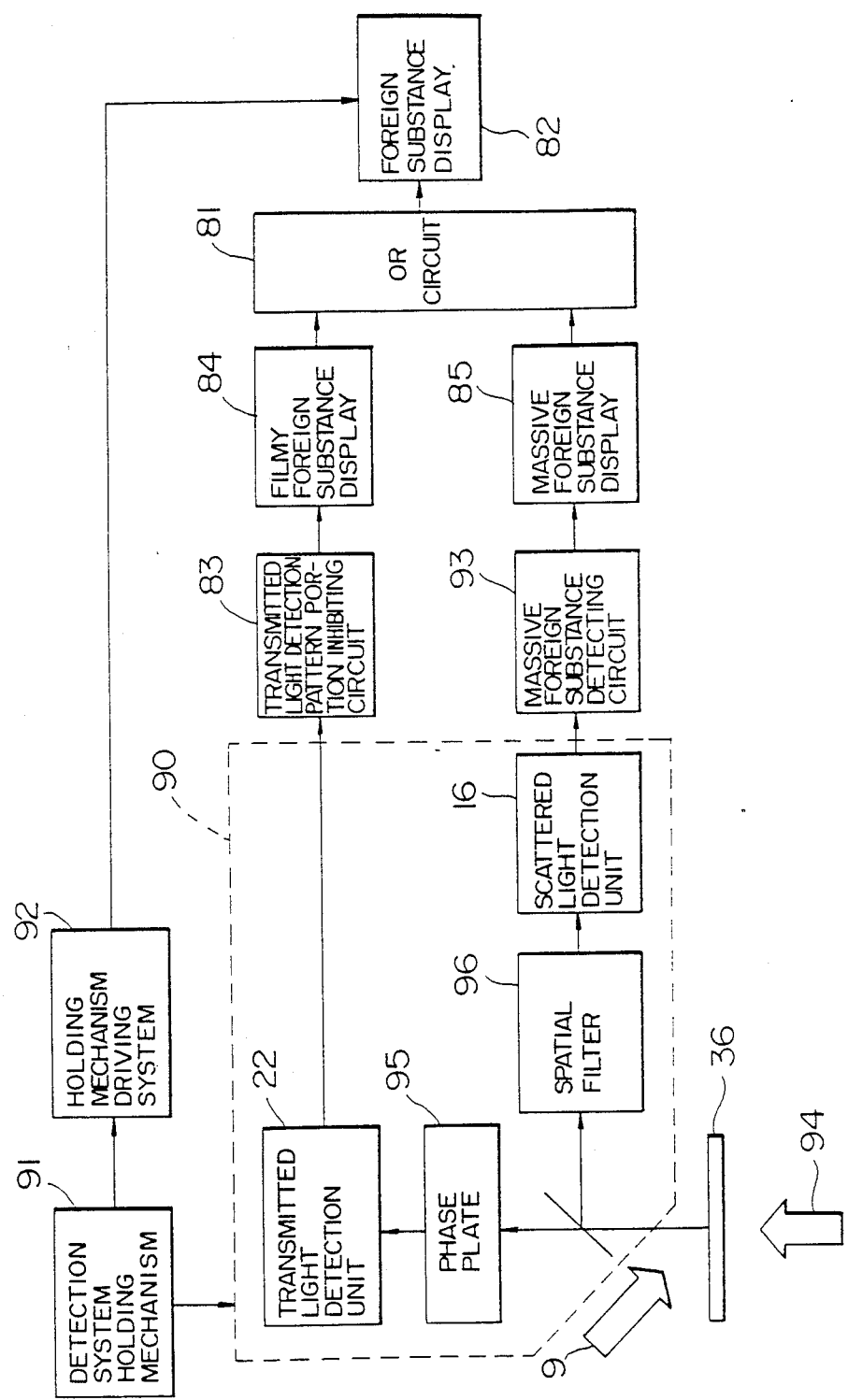
Figure 66:
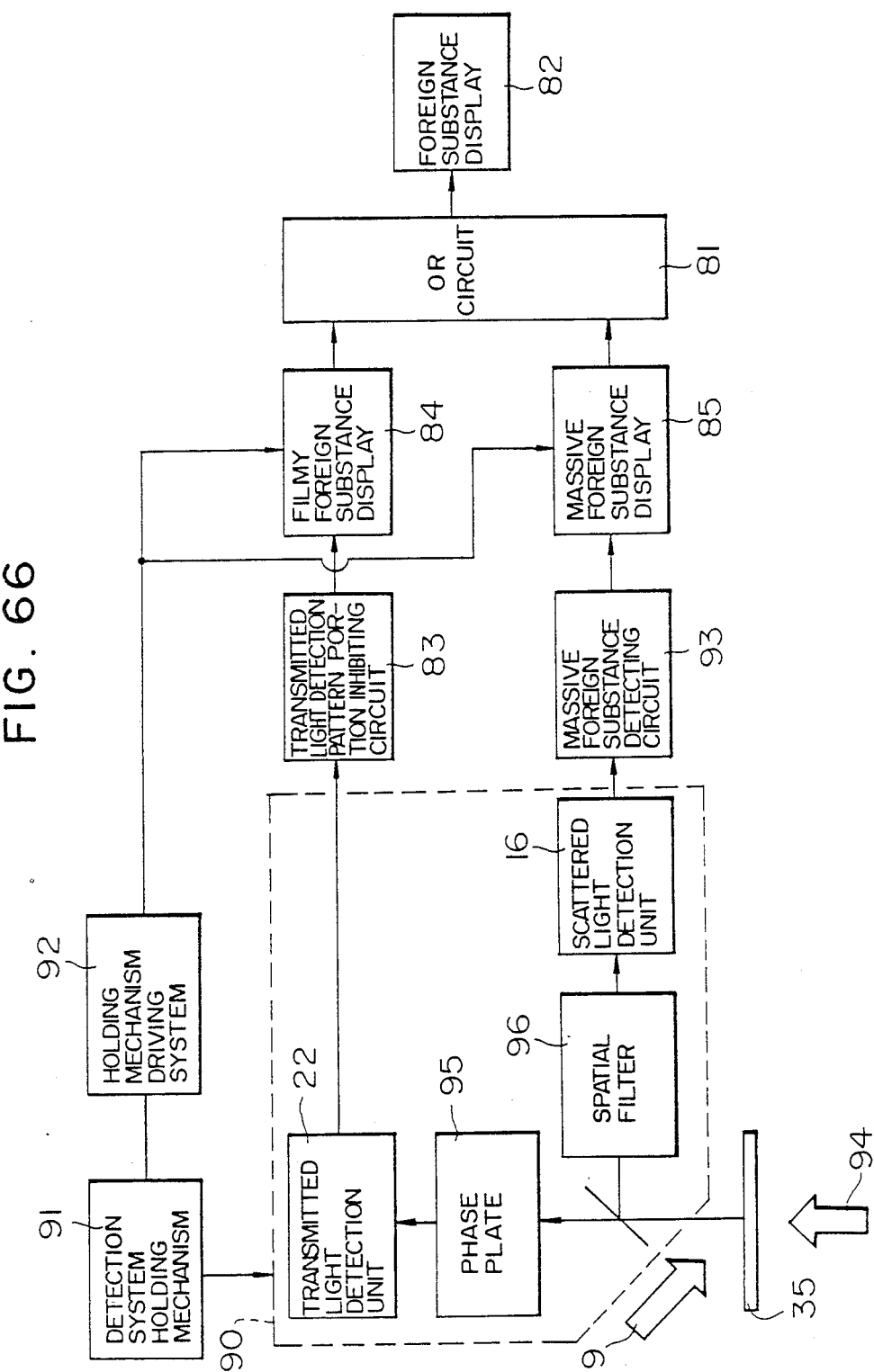
Figure 67:
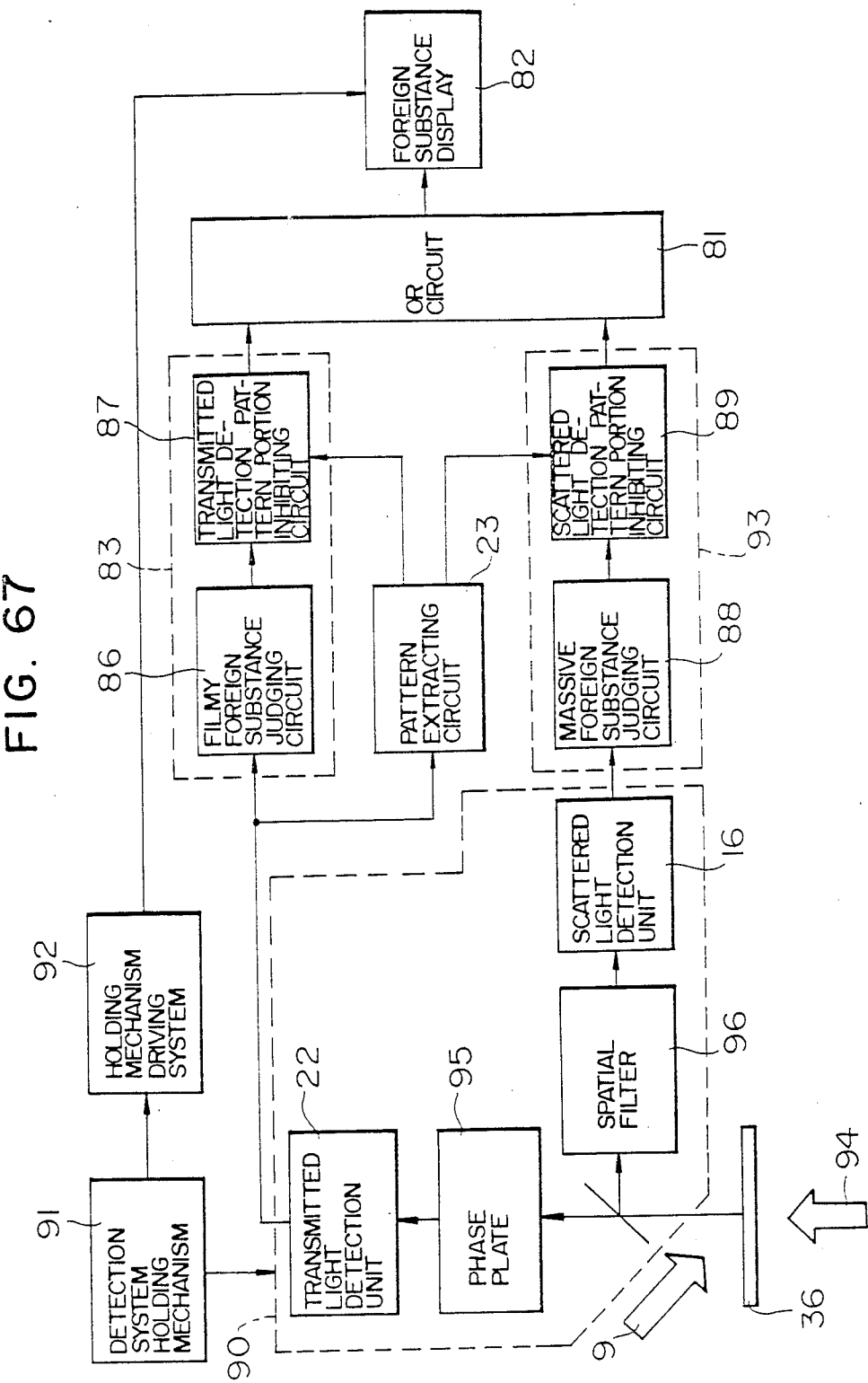
Figure 68:
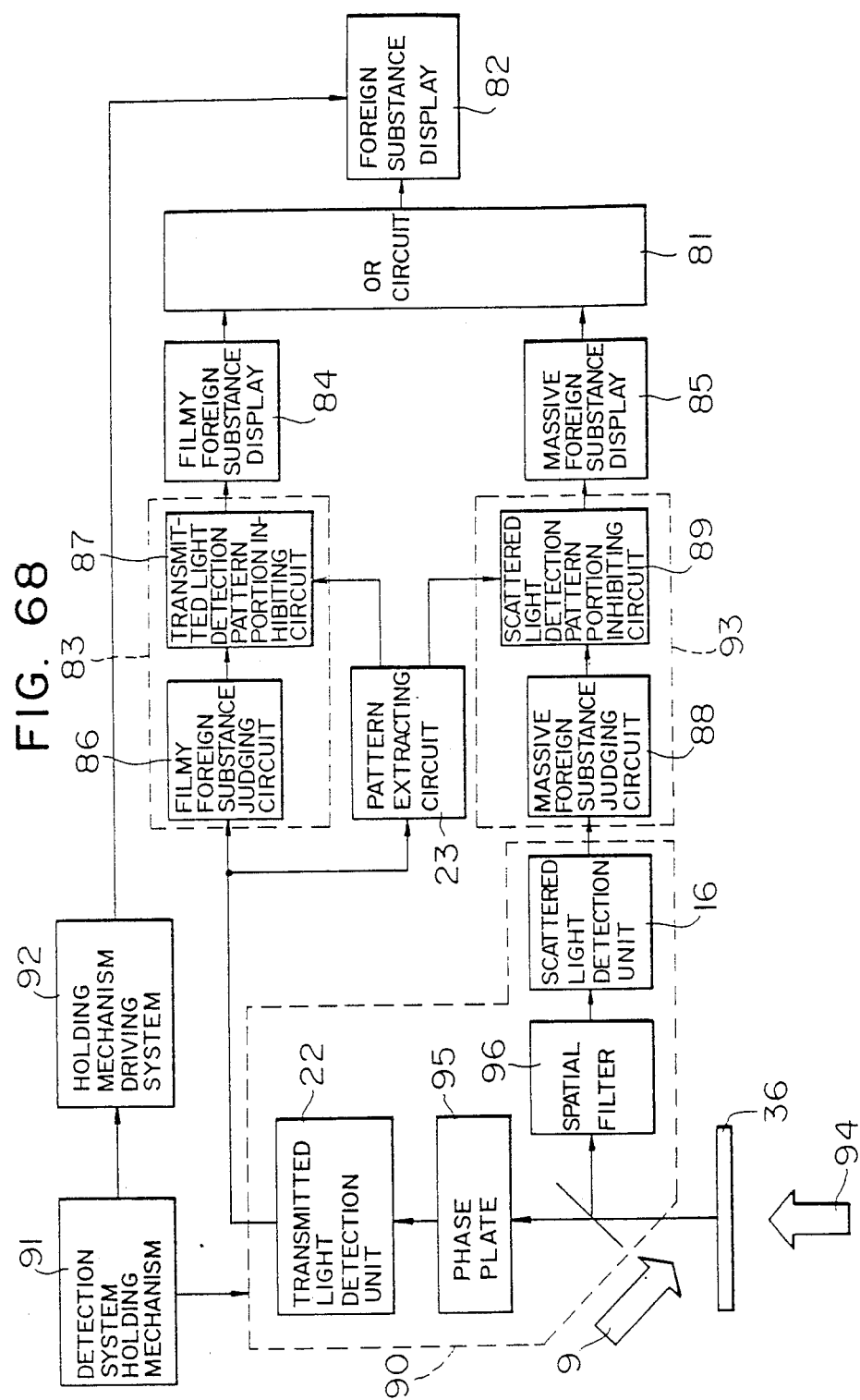
Figure 69:
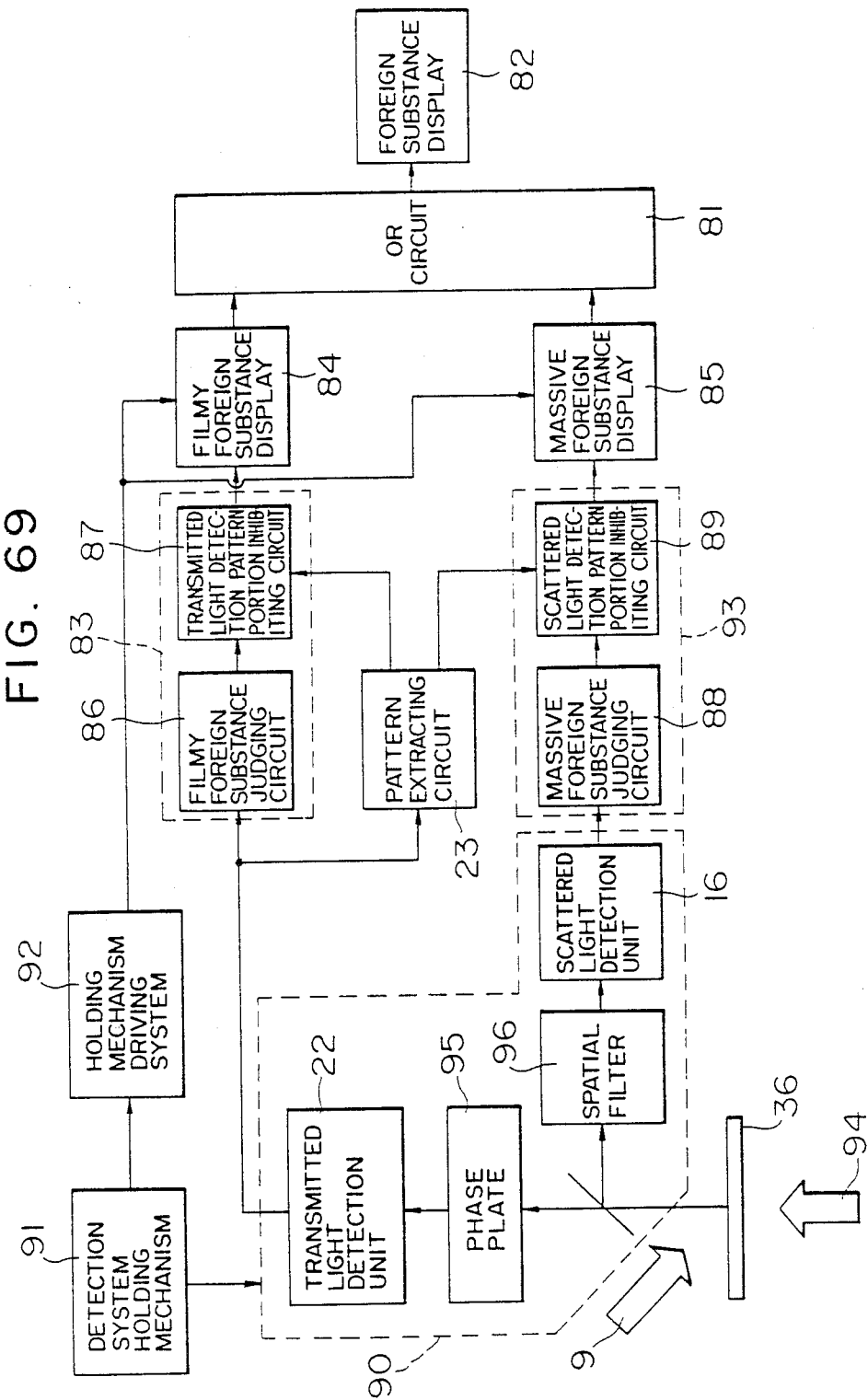
Figure 70:
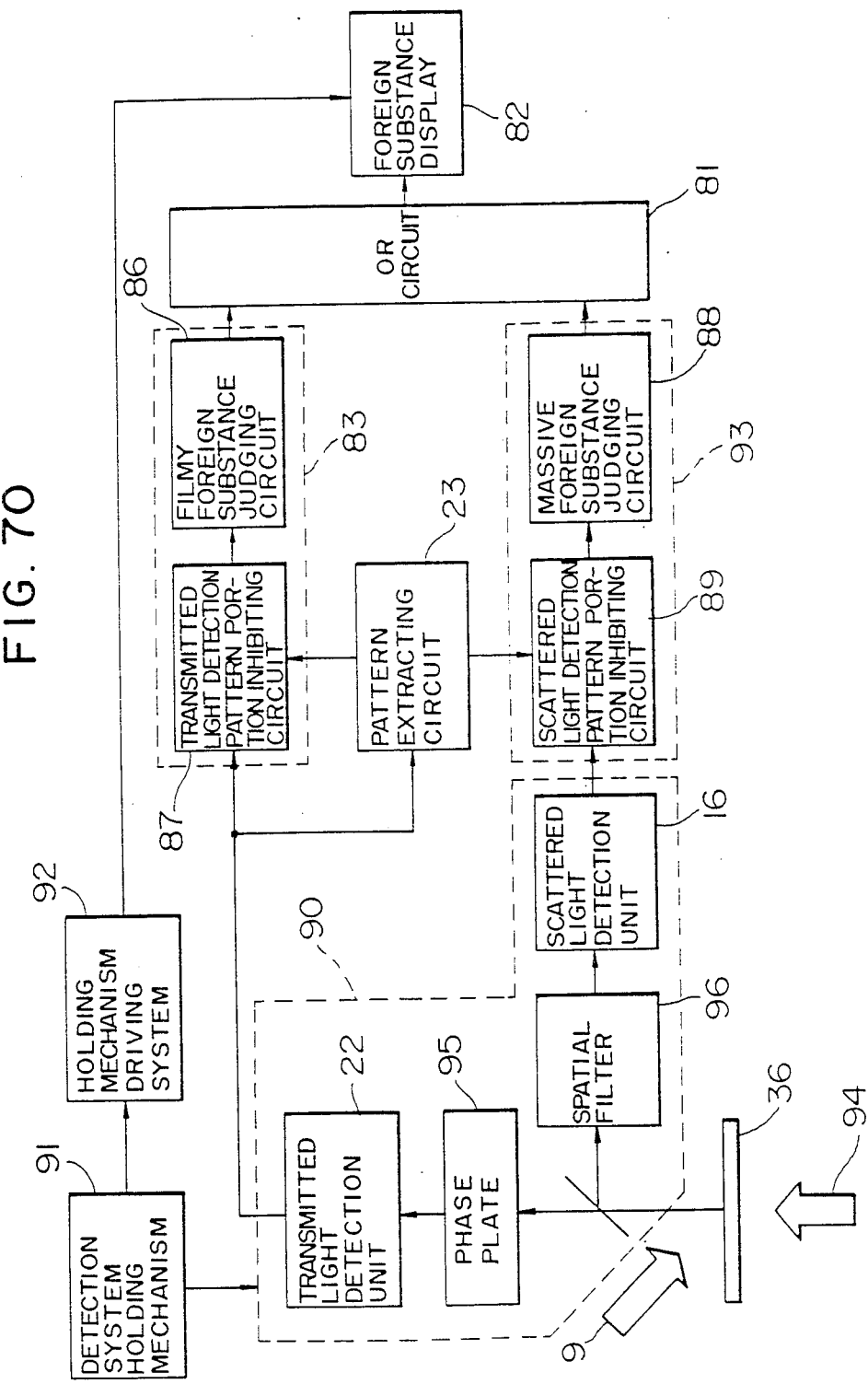
Figure 71:
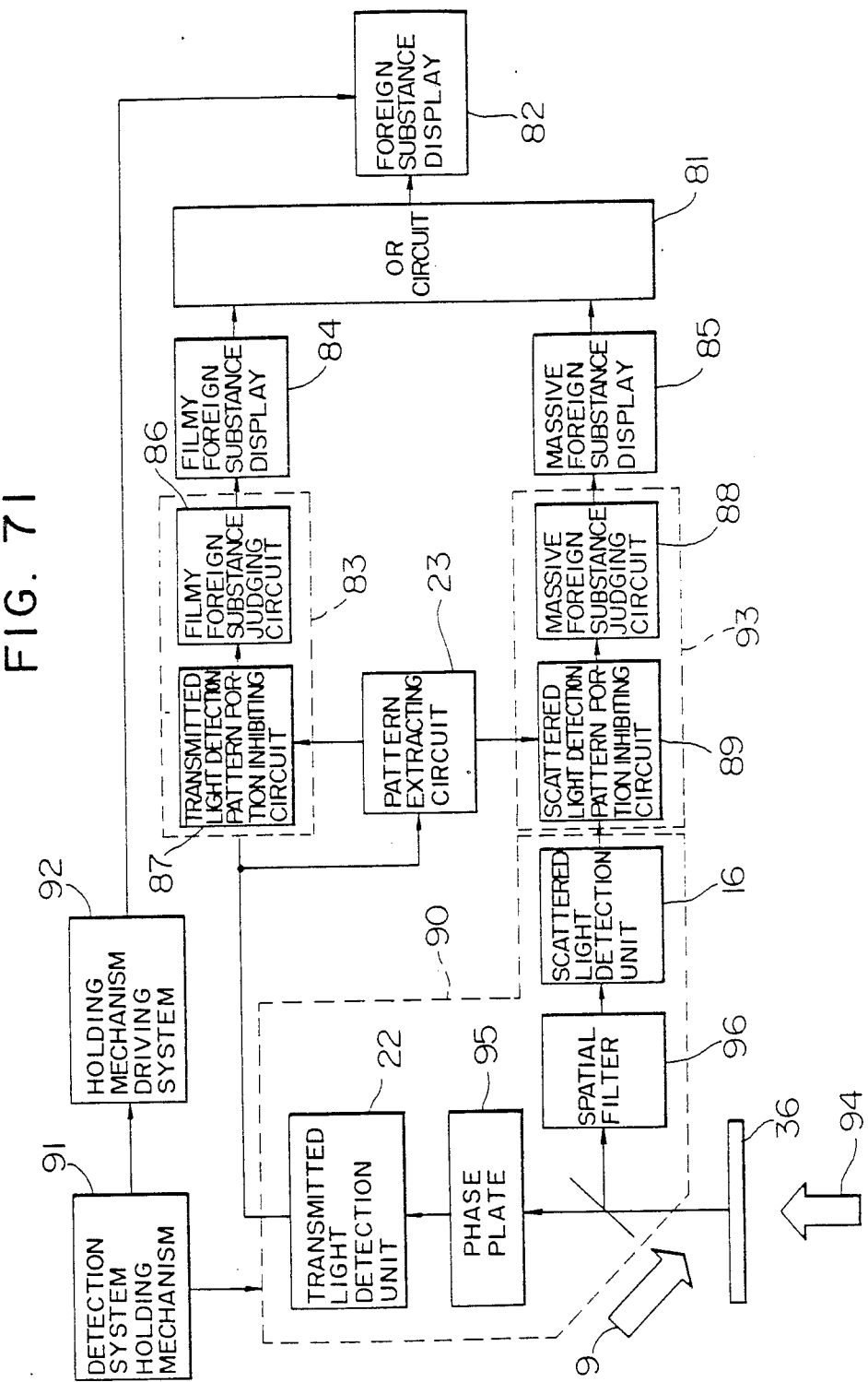
Figure 72:
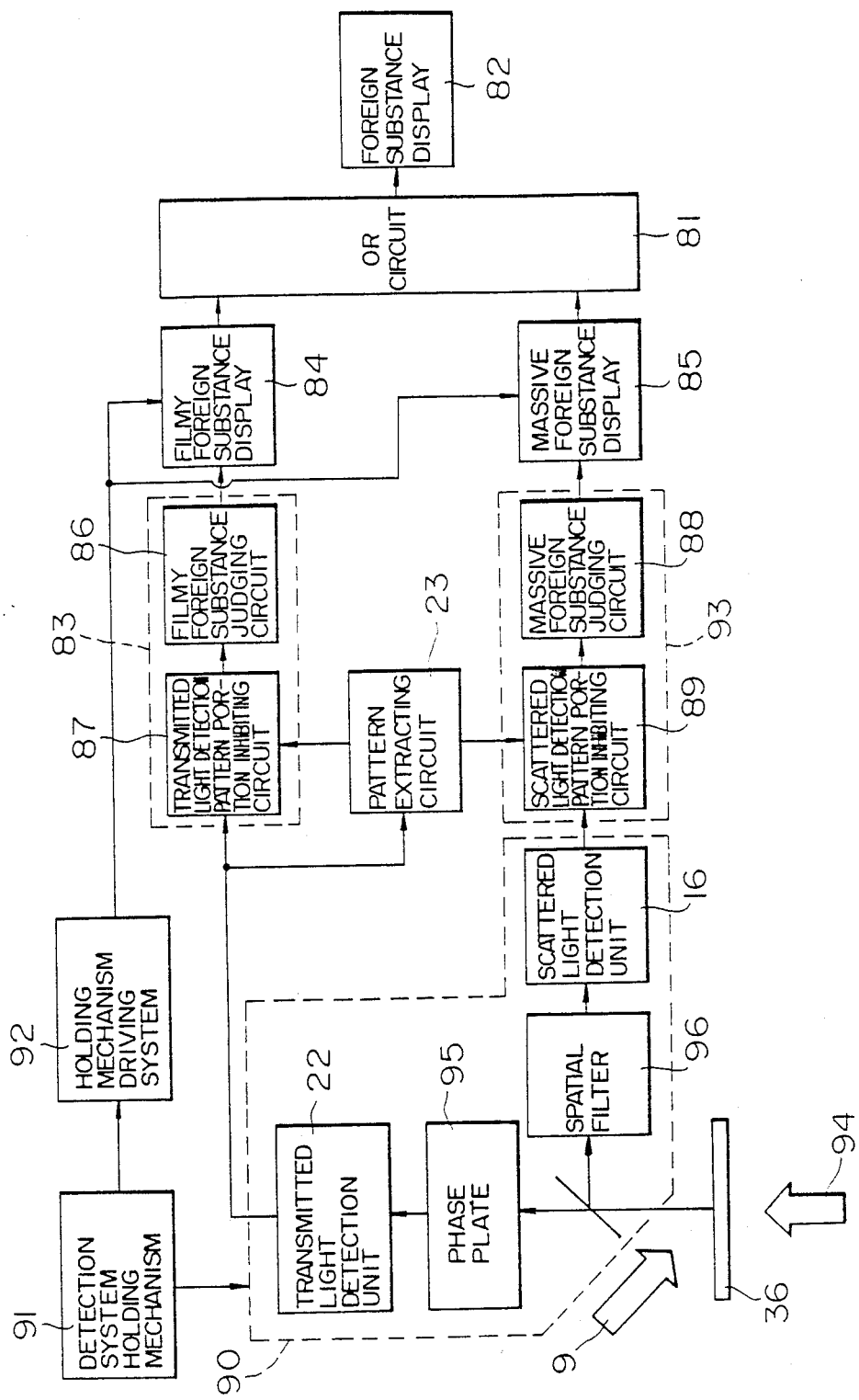

The circuit configurations of FIGS. 31 and 32 are different from the circuit configurations of FIGS. 25 and 26, respectively, in that an optical element (that is, a spatial filter, an analyzer, or the combination of a spatial filter and an analyzer) 96 for detecting scattered light, a light source 94 for phase contrast microscope and a phase plate 95 for phase contrast microscope are used to optically inhibit the image of a pattern portion.

The circuit configurations of FIGS. 33 to 36 are different from the circuit configurations of FIGS. 27 to 30 in that the optical element (that is, the spatial filter, the analyzer, or the combination of the spatial filter and the analyzer) 96 and the phase plate 95 are used together with the pattern extracting circuit 23 and the pattern portion inhibiting circuits 87 and 89, to inhibit a pattern portion optically and electrically.

The circuit configurations of FIGS. 37, 38, 40, 41, 43, 44, 46, 47, 49, 50, 52 and 53 are different from the circuit configurations of FIGS. 25 to 36 in that a movable stage (namely, X-Y-Z stage) 1 for causing the specimen 36 to perform a scanning operation and a driving system 2 for driving the stage 1 are provided. Thus, when a foreign substance is detected, the coordinates of the stage 1 at a time the foreign substance is detected, that is, the coordinates of the position of the foreign substance can be displayed by the display device 82 together with the result of detection of the foreign substance.

The curcuit configurations of FIGS. 39, 42, 45, 48, 51 and 54 are different from the circuit configurations of FIGS. 38, 41, 44, 47, 50 and 53, respectively, in that the result of detection of a filmy foreign substance and the position coordinates of the detected filmy foreign substance are displayed by the filmy foreign substance display device 84, and the result of detection of a massive foreign substance and the position coordinates of the detected massive foreign substance are displayed by the massive foreign substance display device 85.

The circuit configurations of FIGS. 55 to 72 are different from the circuit configurations of FIGS. 37 to 54 in that the movable stage 1 and the driving system 2 are not provided, but a movable detection system 90, holding mechanism 91 for causing the detection system 90 to perform a scanning operation and a driving system 92 for driving the holding mechanism 91 are provided.

Figure 89:
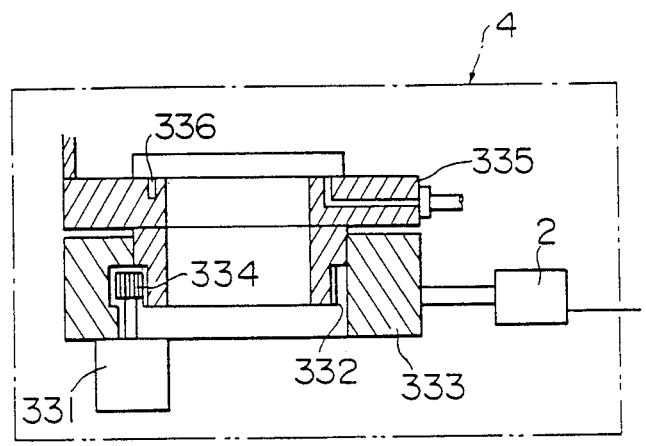
FIG. 89 is a sectional view showing a specimen holding stage different from the X-Y-Z stage of FIG. 1.

The X-Y-Z stage 1 of FIG. 1 may be replaced by an X-θ-Z stage shown in FIG. 89. Referring to FIG. 89, the X-θ-Z stage is made up of an X-stage 333, an X-stage driving system 2, a θ-stage (namely, rotatable stage) 335, a θ-stage gear 332, a θ-stage driving system 331, a mask 336, clamp means 3 for fixing a specimen 36, and a Z-stage (not shown) capable of moving in a Z-direction to place a focal point on the photo-mask 36. The θ-stage can rotate at a constant speed of four revolutions per sec, and the X-stage 333 can move at a constant speed of 0.6 mm/sec in a distance of about 70 mm. Accordingly, it takes about 120 seconds to scan an area of 100 mm × 100 mm with a light beam. Further, the light incident upon the remaining area on the specimen surface other than an area to be inspected, is intercepted by the mask 336 coupled with the θ-stage 335.

As has been explained in the foregoing, according to the present invention, there is provided a foreign substance detecting apparatus for detecting a foreign substance on a reticle or photo-mask having a desired circuit pattern and used for forming a large scale integration circuit, in which apparatus the reflected light from the circuit pattern is eliminated, and thus only a fine massive foreign substance and a filmy foreign substance can be detected without being disturbed by the circuit pattern.

Further, according to the present invention, the circuit pattern on the photo-mask is detected by transmitted light from the photo-mask, and thus the scattered light from a foreign substance can be discriminated from the scattered light from the circuit pattern. Accordingly, it is possible to detect a foreign substance of the order of submicrons which cannot be detected by the prior art.

Furthermore, according to the present invention, an edge portion of a filmy foreign substance can be emphasized by differentiating a detection signal due to transmitted light. Thus, it is possible to detect a filmy foreign substance which cannot be detected by the prior art.

We claim:

1. An apparatus for detecting foreign substances on a photo-mask having a circuit pattern comprising:

stage means for holding said photo-mask thereon;

first illuminating means for obliquely illuminating a position on a front surface of said photo-mask with a laser beam spot of a first predetermined light wavelength at an oblique angle with respect to the front surface of said photo-mask, said first illuminating means including a first light source;

second illuminating means for illuminating a position on a rear surface of said photo-mask with a light spot having a second predetermined light wavelength different from the first predetermined light wavelength of said laser beam spot, said second illuminating means including a second light source, a diaphragm having an aperture for converting light from said light source to the light spot, and focusing means for focusing the light spot onto the rear surface of said photo-mask;

light system means for condensing scattered light reflected from said photo-mask by said laser beam spot and transmitted light transmitted through said photo-mask by said light spot and for dividing said scattered reflected and transmitted light, said light system means including an objective lens for condensing said scattered light and said transmitted light, relay lens means for relaying an image of the objective lens, and dividing element means for dividing said scattered reflected light and transmitted light having different wavelengths;

first light detection means including shielding means for intercepting scattered reflected light generated from an edge of the circuit pattern and passing other scattered reflected light indicative of a massive foreign substance and relay lens means and image pick-up means for converting the passed scattered reflected light to a first signal;

massive foreign substance judging means for providing a massive foreign substance signal indicative of the presence of a massive foreign substance on said photo-mask in accordance with said first signal;

second light detection means including a phase plate for delaying scattered transmitted light scattered by a filmy foreign substance, relay lens means and image pick-up means for converting a phase contrast of the transmitted light to a second signal;

filmy foreign substance judging means for providing a filmy substance signal indicative of the presence of a filmy foreign substance on said photo-mask in accordance with said second signal; and output means for outputting massive foreign substance information determined by said massive foreign substance judging means and filmy foreign substance information determined by said filmy foreign substance judging means by effecting relative scanning of said photo-mask and the laser beam spot and said light spot.

2. An apparatus for detecting foreign substances according to claim 1, wherein said first illuminating means includes setting means for adjusting the oblique direction and position of the laser beam spot.

3. An apparatus for detecting foreign substances according to claim 1, wherein said shielding means of said first light detection means includes a spatial filter.

4. An apparatus for detecting foreign substances according to claim 1, wherein said light source of said first illuminating means provides a linearly-polarized laser beam.

5. An apparatus for detecting foreign substances according to claim 4, wherein said shielding means cf said first light detection means includes a spatial filter and an analyzer.

6. An apparatus for detecting foreign substances according to claim 5, wherein said massive foreign substance judging means includes a binary circuit.

7. An apparatus for detecting foreign substances according to claim 6, wherein said filmy foreign substance judging means includes a binary circuit.

8. An apparatus for detecting foreign substances according to claim 1, further comprising pattern extracting means for detecting a circuit pattern signal in accordance with said second signal and for providing an output to said massive foreign substance judging means so as to remove a noise signal due to said circuit pattern from said massive foreign substance signal.

9. An apparatus for detecting foreign substances according to claim 1, further comprising pattern extracting means for detecting a circuit pattern signal in accordance with said second signal and for providing; an output to said filmy foreign substance judging means so as to remove a noise signal due to said circuit pattern from said filmy foreign substance signal.

10. A apparatus for detecting foreign substances according to claim 8, wherein said pattern extracting means includes a binary circuit for converting said second signal to a binary circuit pattern signal and means for expanding said binary circuit pattern signal.

11. An apparatus for detecting foreign substances according to claim 9, wherein said pattern extracting means includes a binary circuit for converting said second signal to a binary circuit pattern signal and means for expanding said binary circuit pattern signal.

12. An apparatus for detecting foreign substances according to claim 8, wherein said massive foreign substance judging means included pattern angle detecting means for detecting a pattern edge angle by extracting a distribution of light and shade image on a portion of an edge of the circuit pattern, said means for judging a massive foreign substance signal according to a pattern edge signal determined by said pattern edge angle.

* * * * *